US010952995B2

(12) United States Patent
Heffron et al.

(10) Patent No.: US 10,952,995 B2
(45) Date of Patent: Mar. 23, 2021

(54) AZAINDOLES AS INHIBITORS OF HPK1

(71) Applicant: Genentech, Inc., South San Francisco, CA (US)

(72) Inventors: Timothy Heffron, Burlingame, CA (US); Sushant Malhotra, Burlingame, CA (US); BinQing Wei, Belmont, CA (US); Bryan Chan, Foster City, CA (US); Lewis Gazzard, Belmont, CA (US); Emanuela Gancia, Harlow (GB); Michael Lainchbury, Harlow (GB); Andrew Madin, Harlow (GB); Eileen Seward, Harlow (GB); Yonghan Hu, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/568,459

(22) Filed: Sep. 12, 2019

(65) Prior Publication Data
US 2020/0000780 A1 Jan. 2, 2020

Related U.S. Application Data

(63) Continuation of application No. PCT/EP2018/056390, filed on Mar. 14, 2018.

(30) Foreign Application Priority Data

Mar. 15, 2017 (WO) ................ PCT/CN2017/076713

(51) Int. Cl.
| | |
|---|---|
| *A61K 31/437* | (2006.01) |
| *A61K 31/444* | (2006.01) |
| *A61K 31/506* | (2006.01) |
| *A61K 31/513* | (2006.01) |
| *A61K 31/5377* | (2006.01) |
| *C07D 471/04* | (2006.01) |

(52) U.S. Cl.
CPC .......... *A61K 31/437* (2013.01); *A61K 31/444* (2013.01); *A61K 31/506* (2013.01); *A61K 31/513* (2013.01); *A61K 31/5377* (2013.01); *C07D 471/04* (2013.01)

(58) Field of Classification Search
None
See application file for complete search history.

(56) References Cited

FOREIGN PATENT DOCUMENTS

| WO | 03/082868 A1 | 10/2003 | |
|---|---|---|---|
| WO | WO-03082869 A1 * | 10/2003 | ............. A61P 17/00 |
| WO | 2012/003912 A1 | 1/2012 | |
| WO | WO-2015112854 A1 * | 7/2015 | ............. A61P 35/04 |
| WO | 2016/205942 A1 | 12/2016 | |

OTHER PUBLICATIONS

"International Preliminary Report on Patentability—PCT/EP2018/056390":pp. 1-7 (dated Sep. 26, 2019).
International Search Report—PCT/EP2018/056390:pp. 1-12 (dated May 17, 2018).

* cited by examiner

*Primary Examiner* — Zinna Northington Davis
(74) *Attorney, Agent, or Firm* — Zong-Qiang Bill Tian

(57) ABSTRACT

Azaindole compounds and their use as inhibitors of HPK1 are described. The compounds are useful in treating HPK1-dependent disorders and enhancing an immune response. Also described are methods of inhibiting HPK1, methods of treating HPK1-dependent disorders, methods for enhancing an immune response, and methods for preparing the azaindole compounds.

32 Claims, No Drawings
Specification includes a Sequence Listing.

SEQUENCE LISTING

```
<160> NUMBER OF SEQ ID NOS: 4

<210> SEQ ID NO 1
<211> LENGTH: 2502
<212> TYPE: DNA
<213> ORGANISM: Homo sapiens

<400> SEQUENCE: 1
atggacgtcg tggaccctga cattttcaat agagaccccc gggaccacta tgacctgcta      60
cagcggctgg gtggcggcac gtatggggaa gtctttaagg ctcgagacaa ggtgtcaggg     120
gacctggtgg cactgaagat ggtgaagatg gagcctgatg atgatgtctc cacccttcag     180
aaggaaatcc tcatattgaa aacttgccgg cacgccaaca tcgtggccta ccatgggagt     240
tatctctggt tgcagaaact ctggatctgc atggaattct gtggggctgg ttctctccag     300
gacatctacc aagtgacagg ctccctgtca gagctccaga ttagctatgt ctgccgggaa     360
gtgctccagg gactggccta tttgcactca cagaagaaga tacacaggga catcaaggga     420
gctaacatcc tcatcaatga tgctggggag gtcagattgg ctgactttgg catctcggcc     480
cagattgggg ctacactggc cagacgcctc tctttcattg gacaccccta ctggatggct     540
ccggaagtgg cagctgtggc cctgaaggga ggatacaatg agctgtgtga catctggtcc     600
ctgggcatca cggccatcga actggccgag ctacagccac cgctctttga tgtgcaccct     660
ctcagagttc tcttcctcat gaccaagagt ggctaccagc ctccccgact gaaggaaaaa     720
ggcaaatggt cggctgcctt ccacaacttc atcaaagtca ctctgactaa gagtcccaag     780
aaacgaccca gcgccaccaa gatgctcagt catcaactgg tatcccagcc tgggctgaat     840
cgaggcctga tcctggatct tcttgacaaa ctgaagaatc ccgggaaagg accctccatt     900
ggggacattg aggatgagga gcccgagcta cccctgcta tccctcggcg gatcagatcc      960
acccaccgct ccagctctct ggggatccca gatgcagact gctgtcggcg gcacatggag    1020
ttcaggaagc tccgaggaat ggagaccaga cccccagcca acaccgctcg cctacagcct    1080
cctcgagacc tcaggagcag cagcccccagg aagcaactgt cagagtcgtc tgacgatgac    1140
tatgacgacg tggacatccc cacccctgca gaggacacac ctcctccact tccccccaag    1200
```

```
cccaagttcc gttctccatc agacgagggt cctgggagca tggggggatga tgggcagctg    1260 agcccggggg tgctggtccg gtgtgccagt gggcccccac caaacagccc ccgtcctggg    1320
cctcccccat ccaccagcag cccccacctc accgcccatt cagaaccctc actctggaac    1380
ccaccctccc gggagcttga caagccccca cttctgcccc caagaagga aaagatgaag    1440 agaaagggat gtgcccttct cgtaaagttg ttcaatggct gcccctccg gatccacagc    1500 acggccgcct ggacacatcc ctccaccaag gaccagcacc tgctcctggg ggcagaggaa    1560
ggcatcttca tcctgaaccg gaatgaccag gaggccacgc tggaaatgct ctttcctagc    1620
cggactacgt gggtgtactc catcaacaac gttctcatgt ctctctcagg aaagaccccc    1680
cacctgtatt ctcatagcat ccttggcctg ctggaacgga aagagaccag agcaggaaac    1740
cccatcgctc acattagccc ccaccgccta ctggcaagga gaacatggt ttccaccaag    1800 atccaggaca ccaaaggctg ccgggcgtgc tgtgtggcgg agggtgcgag ctctgggggc    1860
ccgttcctgt gcggtgcatt ggagacgtcc gttgtcctgc ttcagtggta ccagcccatg    1920
aacaaattcc tgcttgtccg gcaggtgctg ttcccactgc cgacgcctct gtccgtgttc    1980
gcgctgctga ccgggccagg ctctgagctg cccgctgtgt gcatcggcgt gagccccggg    2040
cggccgggga agtcggtgct cttccacacg gtgcgctttg gcgcgctctc ttgctggctg    2100
ggcgagatga gcaccgagca caggggaccc gtgcaggtga cccaggtaga ggaagatatg    2160
gtgatggtgt tgatggatgg ctctgtgaag ctggtgaccc cggaggggtc cccagtccgg    2220
ggacttcgca cacctgagat ccccatgacc gaagcggtgg aggccgtggc tatggttgga    2280
ggtcagcttc aggcccttctg gaagcatgga gtgcaggtgt gggctctagg ctcggatcag    2340
ctgctacagg agctgagaga ccctacccte actttccgtc tgcttggctc ccccaggctg    2400
gagtgcagtg gcacgatctc gcctcactgc aacctcctcc tcccaggttc aagcaattct    2460
cctgcctcag cctcccgagt agctgggatt acaggcctgt ag                       2502
```

<210> SEQ ID NO 2
<211> LENGTH: 833
<212> TYPE: PRT
<213> ORGANISM: Homo sapiens

<400> SEQUENCE: 2

```
Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95

Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
        115                 120                 125

His Ser Gln Lys Lys Ile His Arg Asp Ile Lys Gly Ala Asn Ile Leu
    130                 135                 140
```

-continued

```
Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Ser Phe Ile Gly Thr Pro
                165                 170                 175

Tyr Trp Met Ala Pro Glu Val Ala Val Ala Leu Lys Gly Gly Tyr
            180                 185                 190

Asn Glu Leu Cys Asp Ile Trp Ser Leu Gly Ile Thr Ala Ile Glu Leu
            195                 200                 205

Ala Glu Leu Gln Pro Pro Leu Phe Asp Val His Pro Leu Arg Val Leu
        210                 215                 220

Phe Leu Met Thr Lys Ser Gly Tyr Gln Pro Arg Leu Lys Glu Lys
225                 230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
            260                 265                 270

Leu Val Ser Gln Pro Gly Leu Asn Arg Gly Leu Ile Leu Asp Leu Leu
        275                 280                 285

Asp Lys Leu Lys Asn Pro Gly Lys Gly Pro Ser Ile Gly Asp Ile Glu
290                 295                 300

Asp Glu Glu Pro Glu Leu Pro Pro Ala Ile Pro Arg Arg Ile Arg Ser
305                 310                 315                 320

Thr His Arg Ser Ser Ser Leu Gly Ile Pro Asp Ala Asp Cys Cys Arg
                325                 330                 335

Arg His Met Glu Phe Arg Lys Leu Arg Gly Met Glu Thr Arg Pro Pro
            340                 345                 350

Ala Asn Thr Ala Arg Leu Gln Pro Pro Arg Asp Leu Arg Ser Ser Ser
            355                 360                 365

Pro Arg Lys Gln Leu Ser Glu Ser Ser Asp Asp Tyr Asp Asp Val
        370                 375                 380

Asp Ile Pro Thr Pro Ala Glu Asp Thr Pro Pro Pro Leu Pro Pro Lys
385                 390                 395                 400

Pro Lys Phe Arg Ser Pro Ser Asp Glu Gly Pro Gly Ser Met Gly Asp
            405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Ser Thr Ser Ser Pro
            435                 440                 445

His Leu Thr Ala His Ser Glu Pro Ser Leu Trp Asn Pro Pro Ser Arg
        450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
            500                 505                 510

His Leu Leu Leu Gly Ala Glu Glu Gly Ile Phe Ile Leu Asn Arg Asn
            515                 520                 525

Asp Gln Glu Ala Thr Leu Glu Met Leu Phe Pro Ser Arg Thr Thr Trp
        530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
```

```
                    565                 570                 575
Arg Ala Gly Asn Pro Ile Ala His Ile Ser Pro His Arg Leu Leu Ala
            580                 585                 590
Arg Lys Asn Met Val Ser Thr Lys Ile Gln Asp Thr Lys Gly Cys Arg
        595                 600                 605
Ala Cys Cys Val Ala Glu Gly Ala Ser Ser Gly Gly Pro Phe Leu Cys
        610                 615                 620
Gly Ala Leu Glu Thr Ser Val Val Leu Leu Gln Trp Tyr Gln Pro Met
625                 630                 635                 640
Asn Lys Phe Leu Leu Val Arg Gln Val Leu Phe Pro Leu Pro Thr Pro
            645                 650                 655
Leu Ser Val Phe Ala Leu Leu Thr Gly Pro Gly Ser Glu Leu Pro Ala
            660                 665                 670
Val Cys Ile Gly Val Ser Pro Gly Arg Pro Gly Lys Ser Val Leu Phe
            675                 680                 685
His Thr Val Arg Phe Gly Ala Leu Ser Cys Trp Leu Gly Glu Met Ser
        690                 695                 700
Thr Glu His Arg Gly Pro Val Gln Val Thr Gln Val Glu Glu Asp Met
705                 710                 715                 720
Val Met Val Leu Met Asp Gly Ser Val Lys Leu Val Thr Pro Glu Gly
            725                 730                 735
Ser Pro Val Arg Gly Leu Arg Thr Pro Glu Ile Pro Met Thr Glu Ala
            740                 745                 750
Val Glu Ala Val Ala Met Val Gly Gly Gln Leu Gln Ala Phe Trp Lys
            755                 760                 765
His Gly Val Gln Val Trp Ala Leu Gly Ser Asp Gln Leu Leu Gln Glu
        770                 775                 780
Leu Arg Asp Pro Thr Leu Thr Phe Arg Leu Leu Gly Ser Pro Arg Leu
785                 790                 795                 800
Glu Cys Ser Gly Thr Ile Ser Pro His Cys Asn Leu Leu Leu Pro Gly
            805                 810                 815
Ser Ser Asn Ser Pro Ala Ser Ala Ser Arg Val Ala Gly Ile Thr Gly
            820                 825                 830
Leu

<210> SEQ ID NO 3
<211> LENGTH: 2466
<212> TYPE: DNA
<213> ORGANISM: Homo sapiens

<400> SEQUENCE: 3
atggacgtcg tggaccctga cattttcaat agagaccccc gggaccacta tgacctgcta      60
cagcggctgg gtggcggcac gtatggggaa gtctttaagg ctcgagacaa ggtgtcaggg     120
gacctggtgg cactgaagat ggtgaagatg gagcctgatg atgatgtctc cacccttcag     180
aaggaaatcc tcatattgaa aacttgccgg cacgccaaca tcgtggccta ccatgggagt     240
tatctctggt tgcagaaaact ctggatctgc atggaattct gtggggctgg ttctctccag     300
gacatctacc aagtgacagg ctccctgtca gagctccaga ttagctatgt ctgccgggaa     360
gtgctccagg gactggccta tttgcactca cagaagaaga tacacaggga catcaaggga     420
gctaacatcc tcatcaatga tgctggggag gtcagattgg ctgactttgg catctcggcc     480
cagattgggc tacactggca gacgcctc tctttcattg ggacacccta ctggatggct     540
ccggaagtgg cagctgtggc cctgaaggga ggatacaatg agctgtgtga catctggtcc     600
```

```
ctgggcatca cggccatcga actggccgag ctacagccac cgctctttga tgtgcaccct    660
ctcagagttc tcttcctcat gaccaagagt ggctaccagc ctccccgact gaaggaaaaa    720
ggcaaatggt cggctgcctt ccacaacttc atcaaagtca ctctgactaa gagtcccaag    780
aaacgaccca cgccaccaa gatgctcagt catcaactgg tatcccagcc tgggctgaat    840
cgaggcctga tcctggatct tcttgacaaa ctgaagaatc ccgggaaagg accctccatt    900
ggggacattg aggatgagga gcccgagcta ccccctgcta ccctcggcg atcagatcc    960 acccaccgct ccagctctct ggggatccca gatgcagact gctgtcggcg cacatggag    1020 ttcaggaagc tccgaggaat ggagaccaga ccccagcca caccgctcg cctacagcct    1080 cctcgagacc tcaggagcag cagccccagg aagcaactgt cagagtcgtc tgacgatgac    1140
tatgacgacg tggacatccc cacccctgca gaggacacac ctcctccact tcccccaag    1200 cccaagttcc gttctccatc agacgagggt cctgggagca tggggatga tgggcagctg    1260 agcccggggg tgctggtccg tgtgccagt gggccccac caaacagccc ccgtcctggg    1320
cctcccccat ccaccagcag ccccaccct accgcccatt cagaaccctc actctggaac    1380
ccaccctccc gggagcttga caagccccca cttctgcccc caagaagga aaagatgaag    1440 agaaagggat gtgcccttct cgtaaagttg ttcaatggct gcccctccg gatccacagc    1500 acggccgcct ggacacatcc ctccaccaag gaccagcacc tgctcctggg ggcagaggaa    1560
ggcatcttca tcctgaaccg gaatgaccag gaggccacgc tggaaatgct ctttcctagc    1620
cggactacgt gggtgtactc catcaacaac gttctcatgt ctctctcagg aaagacccc    1680 cacctgtatt ctcatagcat ccttggcctg ctggaacgga aagagaccag agcaggaaac    1740
cccatcgctc acattagccc ccaccgccta ctggcaagga gaacatggt ttccaccaag    1800 atccaggaca ccaaaggctg ccgggcgtgc tgtgtggcgg agggtgcgag ctctggggc    1860 ccgttcctgt gcggtgcatt ggagacgtcc gttgtcctgc ttcagtggta ccagcccatg    1920
aacaaattcc tgcttgtccg gcaggtgctg ttcccactgc cgacgcctct gtccgtgttc    1980
gcgctgctga ccgggccagg ctctgagctg cccgctgtgt gcatcggcgt gagccccggg    2040
cggccgggga agtcggtgct cttccacacg gtgcgctttg gcgcgctctc ttgctggctg    2100
ggcgagatga gcaccgagca caggggaccc gtgcaggtga cccaggtaga ggaagatatg    2160
gtgatggtgt tgatggatgg ctctgtgaag ctggtgaccc cggaggggtc cccagtccgg    2220
ggacttcgca cacctgagat ccccatgacc gaagcggtgg aggccgtggc tatggttgga    2280
ggtcagcttc aggccttctg gaagcatgga gtgcaggtgt gggctctagg ctcggatcag    2340
ctgctacagg agctgagaga ccctacccctc actttccgtc tgcttggctc ccccaggcct    2400
gtagtggtgg agacacgccc agtggatgat cctactgctc ccagcaacct ctacatccag    2460
gaatga                                                               2466
```

<210> SEQ ID NO 4
<211> LENGTH: 821
<212> TYPE: PRT
<213> ORGANISM: Homo sapiens

<400> SEQUENCE: 4

Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

```
Lys Ala Arg Asp Lys Val Ser Gly Asp Leu Val Ala Leu Lys Met Val
         35                  40                  45
Lys Met Glu Pro Asp Asp Val Ser Thr Leu Gln Lys Glu Ile Leu
 50                  55                  60
Ile Leu Lys Thr Cys Arg His Ala Asn Ile Val Ala Tyr His Gly Ser
 65                  70                  75                  80
Tyr Leu Trp Leu Gln Lys Leu Trp Ile Cys Met Glu Phe Cys Gly Ala
                 85                  90                  95
Gly Ser Leu Gln Asp Ile Tyr Gln Val Thr Gly Ser Leu Ser Glu Leu
                100                 105                 110
Gln Ile Ser Tyr Val Cys Arg Glu Val Leu Gln Gly Leu Ala Tyr Leu
            115                 120                 125
His Ser Gln Lys Lys Ile His Arg Asp Ile Lys Gly Ala Asn Ile Leu
    130                 135                 140
Ile Asn Asp Ala Gly Glu Val Arg Leu Ala Asp Phe Gly Ile Ser Ala
145                 150                 155                 160
Gln Ile Gly Ala Thr Leu Ala Arg Arg Leu Ser Phe Ile Gly Thr Pro
                165                 170                 175
Tyr Trp Met Ala Pro Glu Val Ala Ala Val Ala Leu Lys Gly Gly Tyr
            180                 185                 190
Asn Glu Leu Cys Asp Ile Trp Ser Leu Gly Ile Thr Ala Ile Glu Leu
        195                 200                 205
Ala Glu Leu Gln Pro Pro Leu Phe Asp Val His Pro Leu Arg Val Leu
    210                 215                 220
Phe Leu Met Thr Lys Ser Gly Tyr Gln Pro Pro Arg Leu Lys Glu Lys
225                 230                 235                 240
Gly Lys Trp Ser Ala Ala Phe His Asn Phe Ile Lys Val Thr Leu Thr
                245                 250                 255
Lys Ser Pro Lys Lys Arg Pro Ser Ala Thr Lys Met Leu Ser His Gln
            260                 265                 270
Leu Val Ser Gln Pro Gly Leu Asn Arg Gly Leu Ile Leu Asp Leu Leu
    275                 280                 285
Asp Lys Leu Lys Asn Pro Gly Lys Gly Pro Ser Ile Gly Asp Ile Glu
290                 295                 300
Asp Glu Glu Pro Glu Leu Pro Pro Ala Ile Pro Arg Arg Ile Arg Ser
305                 310                 315                 320
Thr His Arg Ser Ser Ser Leu Gly Ile Pro Asp Ala Asp Cys Cys Arg
                325                 330                 335
Arg His Met Glu Phe Arg Lys Leu Arg Gly Met Glu Thr Arg Pro Pro
            340                 345                 350
Ala Asn Thr Ala Arg Leu Gln Pro Pro Arg Asp Leu Arg Ser Ser Ser
        355                 360                 365
Pro Arg Lys Gln Leu Ser Glu Ser Ser Asp Asp Tyr Asp Asp Val
    370                 375                 380
Asp Ile Pro Thr Pro Ala Glu Asp Thr Pro Pro Leu Pro Pro Lys
385                 390                 395                 400
Pro Lys Phe Arg Ser Pro Ser Asp Glu Gly Pro Gly Ser Met Gly Asp
                405                 410                 415
Asp Gly Gln Leu Ser Pro Gly Val Leu Val Arg Cys Ala Ser Gly Pro
            420                 425                 430
Pro Pro Asn Ser Pro Arg Pro Gly Pro Pro Ser Thr Ser Ser Pro
    435                 440                 445
His Leu Thr Ala His Ser Glu Pro Ser Leu Trp Asn Pro Pro Ser Arg
```

-continued

```
            450                 455                 460
Glu Leu Asp Lys Pro Pro Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
                500                 505                 510

His Leu Leu Leu Gly Ala Glu Gly Ile Phe Ile Leu Asn Arg Asn
                515                 520                 525

Asp Gln Glu Ala Thr Leu Glu Met Leu Phe Pro Ser Arg Thr Thr Trp
530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                565                 570                 575

Arg Ala Gly Asn Pro Ile Ala His Ile Ser Pro His Arg Leu Leu Ala
                580                 585                 590

Arg Lys Asn Met Val Ser Thr Lys Ile Gln Asp Thr Lys Gly Cys Arg
                595                 600                 605

Ala Cys Cys Val Ala Glu Gly Ala Ser Ser Gly Gly Pro Phe Leu Cys
                610                 615                 620

Gly Ala Leu Glu Thr Ser Val Val Leu Leu Gln Trp Tyr Gln Pro Met
625                 630                 635                 640

Asn Lys Phe Leu Leu Val Arg Gln Val Leu Phe Pro Leu Pro Thr Pro
                645                 650                 655

Leu Ser Val Phe Ala Leu Leu Thr Gly Pro Gly Ser Glu Leu Pro Ala
                660                 665                 670

Val Cys Ile Gly Val Ser Pro Gly Arg Pro Gly Lys Ser Val Leu Phe
                675                 680                 685

His Thr Val Arg Phe Gly Ala Leu Ser Cys Trp Leu Gly Glu Met Ser
                690                 695                 700

Thr Glu His Arg Gly Pro Val Gln Val Thr Gln Val Glu Glu Asp Met
705                 710                 715                 720

Val Met Val Leu Met Asp Gly Ser Val Lys Leu Val Thr Pro Glu Gly
                725                 730                 735

Ser Pro Val Arg Gly Leu Arg Thr Pro Glu Ile Pro Met Thr Glu Ala
                740                 745                 750

Val Glu Ala Val Ala Met Val Gly Gly Gln Leu Gln Ala Phe Trp Lys
                755                 760                 765

His Gly Val Gln Val Trp Ala Leu Gly Ser Asp Gln Leu Leu Gln Glu
                770                 775                 780

Leu Arg Asp Pro Thr Leu Thr Phe Arg Leu Leu Gly Ser Pro Arg Pro
785                 790                 795                 800

Val Val Val Glu Thr Arg Pro Val Asp Asp Pro Thr Ala Pro Ser Asn
                805                 810                 815

Leu Tyr Ile Gln Glu
                820
```

AZAINDOLES AS INHIBITORS OF HPK1

CROSS-REFERENCE TO RELATED APPLICATIONS

This application is a continuation of International Patent Application No. PCT/EP2018/056390, filed on 14 Mar. 2018, which claims priority to International Patent Application No. PCT/CN2017/076713 filed on 15 Mar. 2017, the contents of which applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on 9 Sep. 2019, is named P34140-US_SeqListing.txt and is 21,188 bytes in size.

BACKGROUND

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells and therefore, end up damaging healthy cells. Therapeutics that more specifically target tumor cells are being developed by taking advantage of tumor-specific expression of antigens or inappropriate overexpression or activation of specific proteins within tumor cells, but tumor cells are prone to mutation and can become resistant to drugs that specifically target tumor cells.

A new cancer treatment paradigm has emerged that harnesses the patient's own immune system to overcome immunoevasive strategies utilized by many cancers and to enhance anti-tumor immunity. One such strategy is to inhibit negative regulators of immune responses that normally function to maintain peripheral tolerance, allowing tumor antigens to be recognized as non-self entities.

The hematopoietic progenitor kinase 1 (HPK1) is an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) *J Cell Biol* 195(5):839-853). HPK1 can also become activated in response to prostaglandin E2, which is often secreted by tumors, contributing to the escape of tumor cells from the immune system.

BRIEF SUMMARY

Antagonists of the enzyme HPK1 are provided herein. The compounds have a structure set forth in Formula I or Ia or are pharmaceutically acceptable salts, metabolites, prodrugs, or derivatives thereof. Further provided are methods of preparing the compounds of formulae I and Ia.

The compounds find use in inhibiting HPK1 kinase activity, enhancing an immune response, and in the treatment of HPK1-dependent disorders. Accordingly, pharmaceutical compositions comprising a compound of Formula I or Ia or a pharmaceutically acceptable salt, prodrug, metabolite, or derivative thereof and a pharmaceutically acceptable carrier are also provided. Methods of inhibiting HPK1 comprise contacting HPK1 with an effective amount of a compound of Formula I or Ia or a pharmaceutically acceptable salt, prodrug, metabolite, or derivative thereof. Methods of treating a HPK1-dependent disorder comprise administering to a subject in need thereof a compound of Formula I or Ia or a pharmaceutical formulation thereof.

DETAILED DESCRIPTION

Definitions

The term "substituent" refers to an atom or a group of atoms that replaces a hydrogen atom on a molecule. The term "substituted" denotes that a specified molecule bears one or more substituents. The term "a compound of the formula" or "a compound of formula" or "compounds of the formula" or "compounds of formula" refers to any compound selected from the genus of compounds as defined by Formula I or Ia.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

The term "haloalkoxy" refers to an —O-alkyl radical that is substituted by one or more halo substituents. Examples of haloalkoxy groups include trifluoromethoxy, and 2,2,2-trifluoroethoxy.

The term "haloalkyl" refers to an alkyl radical that is substituted by one or more halo substituents. Examples of haloalkyl groups include trifluoromethyl (—$CF_3$), and 2,2,2-trifluoroethyl.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include benzofuranyl, benzothiophenyl, furanyl, thienyl, imidazolyl, indolyl, indazolyl, azaindolyl, azabenzimidazolyl, benzoxazolyl, benzthiazolyl, benzothiadiazolyl, benzotriazolyl, benzoimidazolyl, tetrazinyl, tetrazolyl, isothiazolyl, oxazolyl, oxadiazolyl, isoxazolyl, pyrazinyl, pyrazolyl, pyridazinyl, pyridinyl, pyrimidinyl, pyrrolyl, quinolinyl, isoquinolinyl, quinazolinyl, quinoxalinyl, triazinyl, triazolyl, thiazolyl and thiophenyl. and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include tetrahydrofuranyl, thiomorpholinyl, pyranyl, 1,4-dioxanyl, 1,3-dioxanyl, oxolanyl, oxetanyl, 2-oxa-6-azaspiro[3.3]heptan-6-yl, piperidinyl, pyrrolidinyl, morpholinyl, azetidinyl, piperazinyl, pyrrolidinonyl, piperazinonyl, pyrazolidinyl, imidazolinyl, imidazolidinyl and tetrahydrothienyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not minor images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

Furthermore the compounds described herein may include olefins having either geometry: "Z" refers to what is referred to as a "cis" (same side) configuration whereas "E" refers to what is referred to as a "trans" (opposite side) configuration.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

With respect to the nomenclature of a chiral center, the terms "d" and "l" (or plus and minus) configuration are as defined by the IUPAC Recommendations.

A "metabolite" is a product produced through metabolism in the body of a specified compound or salt thereof. Metabolites of a compound may be identified using routine techniques known in the art and their activities determined using tests such as those described herein. Such products may result for example from the'oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the subject being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt, the salt can have multiple counter ions.

Hence, a pharmaceutically acceptable salt can have one or more charged atoms and/or one or more counter ion.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. In certain embodiments, the pharmaceutically acceptable carrier is a non-naturally occurring pharmaceutically acceptable carrier.

Use of the word "inhibitor" herein is meant to mean a molecule that inhibits activity of HPK1. By "inhibit" herein is meant to decrease the activity of the target enzyme, as compared to the activity of that enzyme in the absence of the inhibitor. In some embodiments, the term "inhibit" means a decrease in HPK1 activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in HPK1 activity of about 5% to about 25%, about 25% to about 50%, about 50% to about 75%, or about 75% to 100%. In some embodiments, inhibit means a decrease in HPK1 activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, blastomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

A "chemotherapeutic agent" is a chemical compound or protein molecule useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

In some embodiments, the chemotherapeutic agent is an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, such as cytokines, interleukins (e.g., IL-2, IL-7, IL-12, IL-15, IL-21), interferons (e.g., IFN-α, IFN-β, IFN-γ), GM-CSF, thalidomide, (THALOMID®, Celgene), lenalidomide (REVLIMID®, Celgene), pomalidomide (POMALYST®, Celgene), imiquimod (ZYCLARA®, Valeant). Non-limiting examples of monoclonal antibodies that are useful as a chemotherapeutic agent include trastuzumab (HERCEPTIN®, Genentech), bevacizumab (AVASTIN®, Genentech), cetuximab (ERBITUX®, Bristol-Myers Squibb), panitumumab (VECTIBIX®, Amgen), ipilimumab (YERVOY®, Bristol-Myers Squibb), rituximab (RITUXAN®, Genentech), alemtuzumab (CAMPATH®, Genzyme), ofatumumab (ARZERRA®, Genmab), gemtuzumab ozogamicin (MYLOTARG®, Wyeth), brentuximab vedotin (ADCETRIS®, Seattle Genetics), $^{90}$Y-labelled ibritumomab tiuxetan (ZEVALIN®, Biogen Idec), $^{131}$I-labelled tositumomab (BEXXAR®, GlaxoSmithKline), ado-trastuzumab emtansine (KADCYLA®, Genentech) blinatumomab (BLINCYTO®, Amgen), pertuzumab (PERJETA®, Genentech), obinutuzumab (GAZYVA®, Genentech), nivolumab (OPDIVO®,) Bristol-Myers Squibb), pembrolizumab (KEYTRUDA®, Merck), pidilizumab (CureTech), MPDL3280A (described in WO2010/077634, herein incorporated by reference in its entirety), MDX-1105 (described in WO2007/005874, herein incorporated by reference in its entirety), and MEDI4736 (described in WO2011/066389 and US2013/034559, each of which is herein incorporated by reference in its entirety). Another useful immunotherapeutic agent is AMP-224 (described in WO2010/027827 and WO2011/066342, each of which is incorporated herein in its entirety).

Compounds

The compounds of the invention are compounds of Formula I or Ia or pharmaceutically acceptable salts, prodrugs, metabolites, or derivatives thereof. In embodiments, the subject matter described herein is directed to compounds of Formula I. These compounds are useful inhibitors of HPK1.

In some of these embodiments, the compounds have the structure of Formula I:

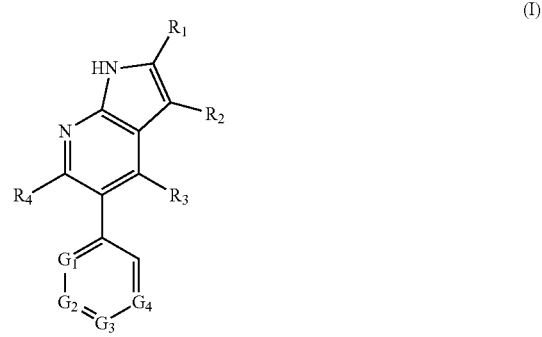

(I)

wherein:
G$_1$ is N or C—R$_{x1}$;
G$_2$ is N or C—R$_{x2}$;
G$_3$ is N or C—R$_{x3}$;
G$_4$ is N or C—R$_{x4}$;
wherein, 0, 1 or 2 of G$_1$, G$_2$, G$_3$, and G$_4$ is N;

$R_{x1}$, $R_{x2}$, $R_{x3}$ and $R_{x4}$, if present, in each instance, is independently selected from the group consisting of hydrogen, halo, $C_6$-$C_{20}$ aryl optionally substituted with one or two $R_{1a}$, $C_1$-$C_{20}$ heteroaryl optionally substituted with one or two $R_{1a}$, —$CONR_6R_7$, —$NR_6R_7$, and —$N(R_8)$—$CO(R_9)$, provided that at least one of $R_{x1}$, $R_{x2}$, $R_{x3}$ and $R_{x4}$ is other than hydrogen;

wherein, $R_6$ and $R_7$ taken together with the N to which each is bound form a 4-, 5-, 6- or 7-member cyclic or heterocyclic ring, wherein said heterocyclic ring may contain one or two additional heteroatoms selected from the group consisting of N, S and O, said ring may be optionally substituted with one or two $R_{1a}$; or $R_6$ and $R_7$ are independently hydrogen or alkyl;

wherein, $R_8$ and $R_9$ taken together with the N or the carbonyl to which each is bound form a 4-, 5-, 6- or 7-member cyclic or heterocyclic ring, wherein said heterocyclic ring may contain one or two additional heteroatoms selected from the group consisting of N, S and O, said ring may be optionally substituted with one or two $R_{1a}$; or $R_8$ and $R_9$ are independently hydrogen or alkyl;

wherein, in each instance, $R_{1a}$ is independently taken together with the carbon to which it is bound to form a carbonyl; or $R_{1a}$ is hydrogen, alkyl, hydroxyl, hydroxyalkyl, halo or haloalkyl;

$R_1$ is hydrogen, alkyl, hydroxyl, hydroxyalkyl, halo or haloalkyl;

$R_2$, $R_3$, and $R_4$, in each instance, is independently hydrogen, alkyl, alkoxy, halo, haloalkyl-, haloalkoxy-, —$R_5$—O—$R_5$, —$SO_2R_5$, —$SOR_5$, or cycloalkyl;

wherein $R_5$, in each instance, is independently an unsubstituted alkyl;

provided that $R_1$ and $R_4$ are not both hydrogen.

In some embodiments, the haloalkyl is —$CF_3$ or —$CF_2R_5$ where $R_5$ is an unsubstituted alkyl. In some embodiments, the haloalkoxy is —O—$CF_3$.

In some embodiments of the compound of Formula I, wherein the compound is other than a compound of Table 1X.

TABLE 1X

| No. | Compound Name |
|---|---|
| 1x | 5-(2'-chloro[3,4'-bipyridin]-5-yl)-2-(trifluoromethyl)-1H-pyrrolo[2,3-b]pyridine |
| 2x | 4-(2-chloro-1H-pyrrolo[2,3-b]pyridin-5-yl)-N,N-dimethylbenzenamine |
| 3x | 2-ethyl-5-(3-fluorophenyl)-1H-pyrrolo[2,3-b]pyridine |
| 4x | 2-chloro-5-(3-fluorophenyl)-1H-pyrrolo[2,3-b]pyridine |

In some embodiments of the method for inhibiting HPK1 comprising contacting HPK1 with a compound of Formula I, or a pharmaceutically acceptable salt thereof, the compound of Formula I excludes one or more of the compounds of Table 1X. In some embodiments, the compound of Formula I includes one or more of the compounds of Table 1X.

In some embodiments of the method for enhancing an immune response in a subject in need thereof comprising administering to the subject a compound of Formula I, or a pharmaceutically acceptable salt thereof, the compound of Formula I excludes one or more of the compounds of Table 1X. In some embodiments, the compound of Formula I includes one or more of the compounds of Table 1X.

In some embodiments of the method for treating a HPK1-dependent disorder (e.g., cancer) in a subject in need thereof comprising administering to the subject a compound of Formula I, or a pharmaceutically acceptable salt thereof, the compound of Formula I excludes one or more of the compounds of Table 1X. In some embodiments, the compound of Formula I includes one or more of the compounds of Table 1X.

In an embodiment, $R_1$ and $R_2$, in each instance, is independently alkyl, haloalkyl (e.g., —$CF_3$), hydroxyalkyl, or halo; and all other variables are as defined in Formula I or are as defined in any of the embodiments described herein.

In an embodiment, $R_1$ and $R_2$, in each instance, is independently halo or alkyl; and all other variables are as defined in Formula I or are as defined in any of the embodiments described herein.

In an embodiment, one or both of $G_1$ and $G_3$ are N; $G_2$ is C—$R_{x2}$; and $G_4$ is C—$R_{x4}$; and all other variables are as defined in Formula I or are as defined in any of the embodiments described herein.

In an embodiment, $G_1$ is N and $G_3$ is C—$R_{x3}$; and all other variables are as defined in Formula I or are as defined in any of the embodiments described herein.

In an embodiment, $G_1$ is C—$R_{x1}$; $G_2$ is C—$R_{x2}$ $G_3$ is C—$R_{x3}$; and $G_4$ is C—$R_{x4}$; and all other variables are as defined in Formula I or are as defined in any of the embodiments described herein.

In an embodiment, two of $R_{x1}$, $R_{x2}$, $R_{x3}$ and $R_{x4}$ are hydrogen; and all other variables are as defined in Formula I or are as defined in any of the embodiments described herein.

In an embodiment, $R_{x2}$ is selected from:

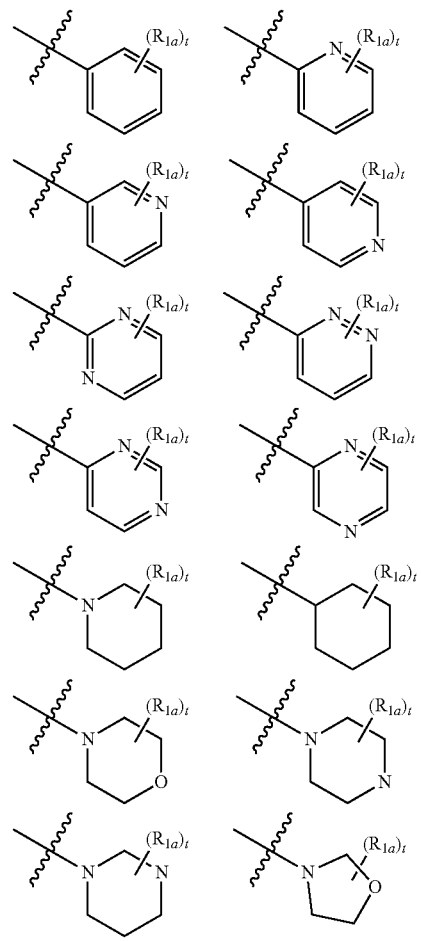

-continued

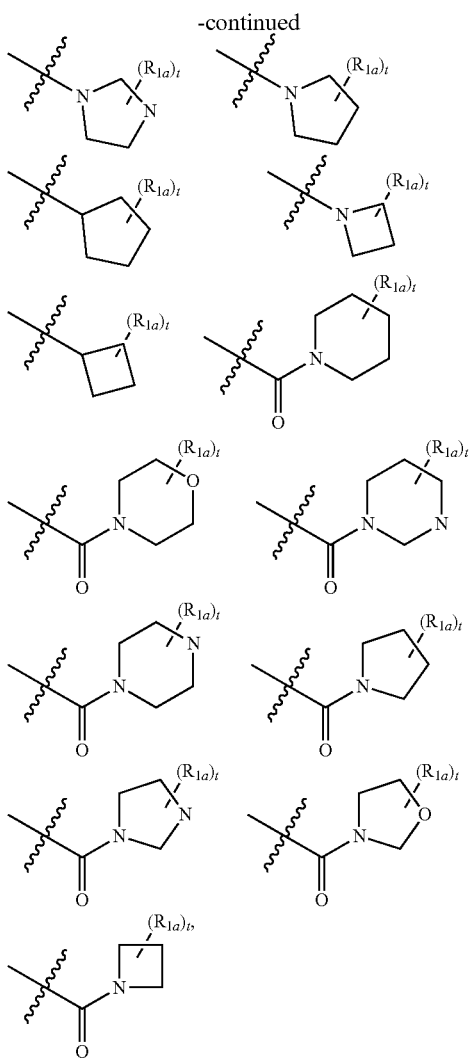

wherein, t is 1 or 2; and all other variables are as defined in Formula I or are as defined in any of the embodiments described herein.

In an embodiment, $R_{x1}$ is hydrogen or halo; $R_{x3}$ is hydrogen or —$NH_2$; $R_{x4}$ is hydrogen or —NH2, wherein at least one of $R_{x1}$, $R_{x2}$ and $R_{x3}$ is hydrogen; and all other variables are as defined in Formula I or are as defined in any of the embodiments described herein.

In an embodiment, $R^1$ is selected from halogen, alkyl and hydroxyalkyl.

In an embodiment, $R^1$ is selected from chloro, fluoro, methyl and hydroxymethyl.

In an embodiment, $R^2$ is selected from hydrogen, alkyl, haloalkyl and hydroxyalkyl.

In an embodiment, $R^2$ is selected from hydrogen, ethyl, trifluoromethyl ($CF_3$), 2-fluoroethyl and 2-hydroxyethyl.

In an embodiment, $R^3$ is hydrogen.

In an embodiment, $R^4$ is hydrogen.

In an embodiment, $G_1$ is N or C—$R_{x1}$, wherein $R_{x1}$ is selected from hydrogen and halogen.

In an embodiment, $G_1$ is N or C—$R_{x1}$, wherein $R_{x1}$ is selected from hydrogen and fluoro.

In an embodiment, $G_2$ is C—$R_{x2}$, wherein $R_{x2}$ is selected from $C_5$-heteroaryl optionally substituted with one $R_{1a}$, —$NR_6R_7$, —N($R_8$)—CO($R_9$) and —$CONR_6R_7$;

wherein, $R_8$ and $R_9$ taken together with the N or the carbonyl to which each is bound form a 5- or 6-membered heterocyclic ring, wherein said heterocyclic ring may contain one additional heteroatom selected from the group consisting of N and O;

wherein, $R_6$ and $R_7$ taken together with the N to which each is bound form a 4- or 6-membered heterocyclic ring, wherein said heterocyclic ring may contain one additional heteroatom being O, said ring may be optionally substituted with one $R_{1a}$; or $R_6$ and $R_7$ are independently alkyl; and wherein, in each instance, $R_{1a}$ is hydroxyl or hydroxyalkyl.

In an embodiment, $G_2$ is C—$R_{x2}$, wherein $R_{x2}$ is selected from 3-hydroxyazetidine-1-carbonyl, 3-(hydroxymethyl)-2-pyridyl, 3-oxomorpholin-4-yl, dimethylcarbamoyl, 2-oxo-hexahydropyrimidin-1-yl, 2-oxooxazolidin-3-yl and 3-(hydroxymethyl)morpholin-4-yl.

In an embodiment, $G_3$ is N or C—$R_{x3}$, wherein $R_{x3}$ is selected from hydrogen and —$NH_2$.

In an embodiment, $G_4$ is C—$R_{x4}$, wherein $R_{x4}$ is selected from hydrogen and —$NH_2$.

In an embodiment, the subject matter described herein is directed to a compound of Formula Ia:

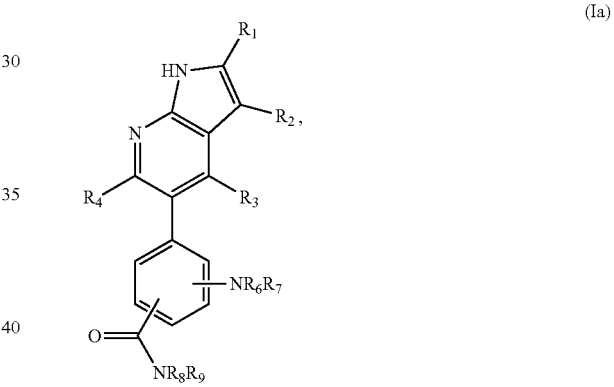

(Ia)

wherein all other variables are as defined in Formula I. In some embodiments, $R_8$ and $R_9$, in each instance, is independently a $C_{1-4}$ alkyl; and $R_6$ and $R_7$ are both hydrogen; and all other variables are as defined in Formula I or are as defined in any of the embodiments described herein.

In an embodiment, $R_8$ and $R_9$ are both methyl; and all other variables are as defined in Formula I or are as defined in any of the embodiments described herein.

In an embodiment, $R_1$ is alkyl, hydroxyl, hydroxyalkyl, halo or haloalkyl; and $R_3$ and $R_4$ are each hydrogen; and all other variables are as defined in Formula I or are as defined in any of the embodiments described herein.

In an embodiment, $R_1$ is alkyl, halo or haloalkyl; $R_2$ is hydrogen, alkyl, alkoxy, halo, haloalkyl or —$CF_3$; and all other variables are as defined in Formula I or are as defined in any of the embodiments described herein.

In an embodiment, $R_1$ is alkyl, hydroxyl, hydroxyalkyl, halo or haloalkyl; and $R_3$ and $R_4$ are each hydrogen; and all other variables are as defined in Formula I or are as defined in any of the embodiments described herein.

In an embodiment, $R_1$ is $C_{1-4}$ alkyl; and all other variables are as defined in Formula I or are as defined in any of the embodiments described herein.

In an embodiment, R₁ is chloro; and all other variables are as defined in Formula I or are as defined in any of the embodiments described herein.

In an embodiment, R₂ is hydrogen, $C_{1-4}$ alkyl or —$CF_3$; and all other variables are as defined in Formula I or are as defined in any of the embodiments described herein.

In embodiments, the subject matter described herein is directed to a compound having one of the structures in Table 1.

TABLE 1

| Structure | Compound |
|---|---|
| 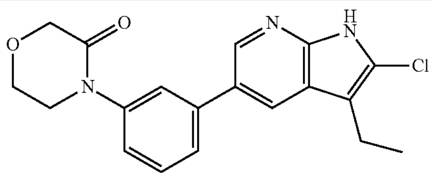 [SMILES: CCc1c(Cl)[nH]c2ncc(-c3cccc(N4CCOCC4=O)c3)cc12] | 1-1 |
| 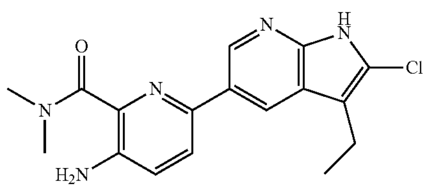 [SMILES: CCc1c(Cl)[nH]c2ncc(-c3ccc(N)c(C(=O)N(C)C)n3)cc12] | 1-2 |
| 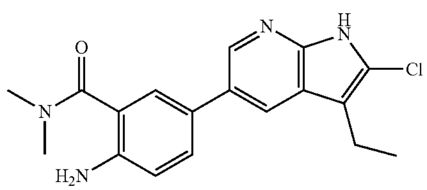 [SMILES: CCc1c(Cl)[nH]c2ncc(-c3ccc(N)c(C(=O)N(C)C)c3)cc12] | 1-3 |
| 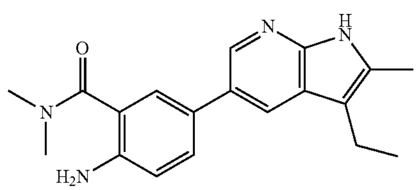 | 1-4 |
| 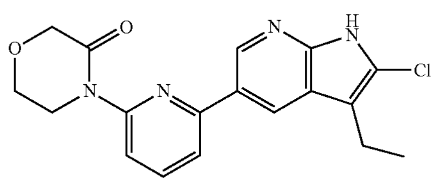 [SMILES: CCc1c(Cl)[nH]c2ncc(-c3cccc(N4CCOCC4=O)n3)cc12] | 1-5 |
| 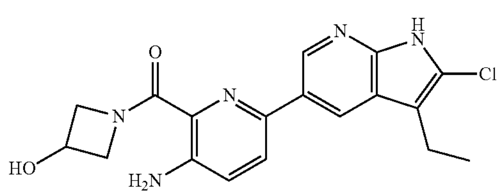 [SMILES: CCc1c(Cl)[nH]c2ncc(-c3ccc(N)c(C(=O)N4CC(O)C4)n3)cc12] | 1-6 |
| 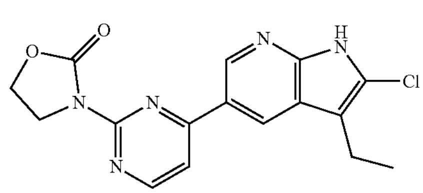 [SMILES: CCc1c(Cl)[nH]c2ncc(-c3ccnc(N4CCOC4=O)n3)cc12] | 1-7 |

TABLE 1-continued

| Structure | Compound |
|---|---|
| 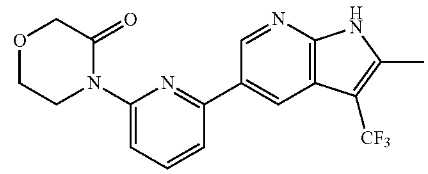 [SMILES: Cc1[nH]c2ncc(-c3cccc(N4CCOCC4=O)n3)cc2c1C(F)(F)F] | 1-8 |
| 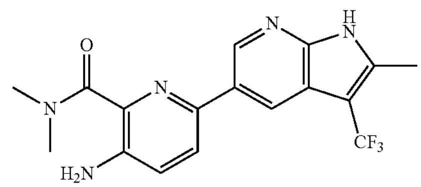 | 1-9 |
| 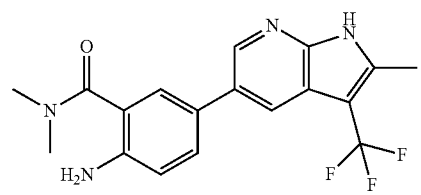 | 1-10 |
| 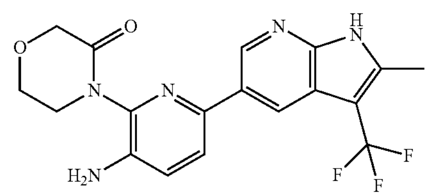 [SMILES: Cc1[nH]c2ncc(-c3ccc(N)c(N4CCOCC4=O)n3)cc2c1C(F)(F)F] | 1-11 |
| 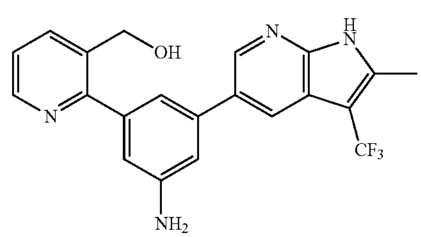 | 1-12 |
| 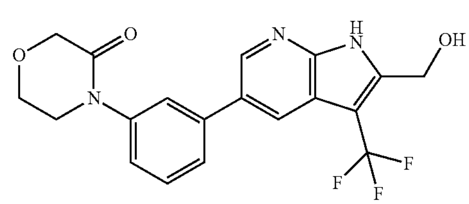 [SMILES: O=C1COCCN1c1cccc(-c2cnc3[nH]c(CO)c(C(F)(F)F)c3c2)c1] | 1-13 |
| 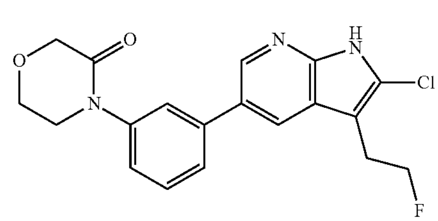 [SMILES: O=C1COCCN1c1cccc(-c2cnc3[nH]c(Cl)c(CCF)c3c2)c1] | 1-14 |

TABLE 1-continued

| Structure | Compound |
|---|---|
| 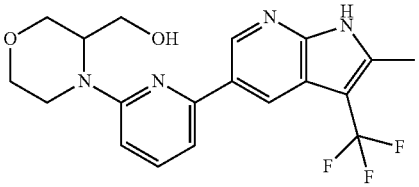 [SMILES: Cc1[nH]c2ncc(-c3cccc(N4CCOCC4CO)n3)cc2c1C(F)(F)F] | 1-15 |
| 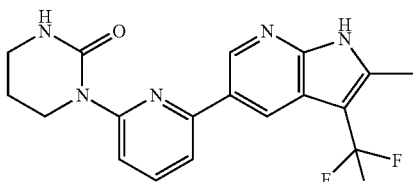 | 1-16 |
| 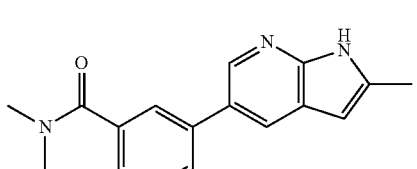 | 1-17 |
| 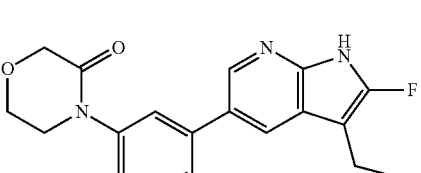 | 1-18 |
| 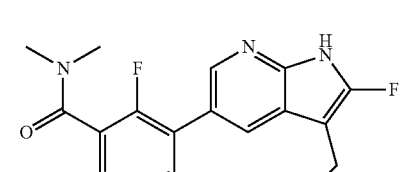 | 1-19 |
| 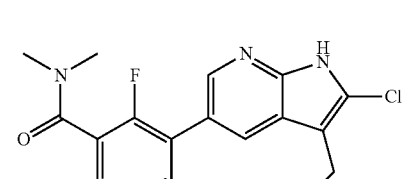 | 1-20 |
| 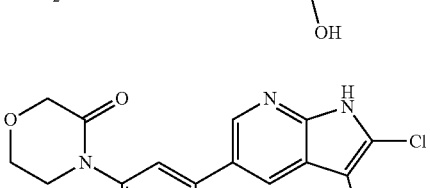 | 1-21 |
| 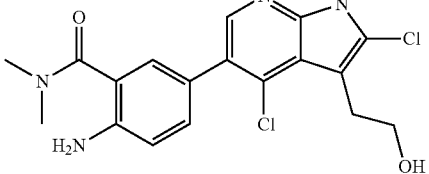 | 1-22 |
| 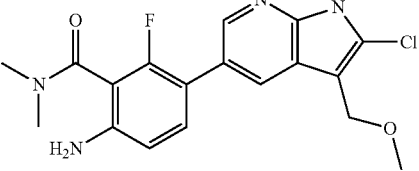 | 1-23 |
| 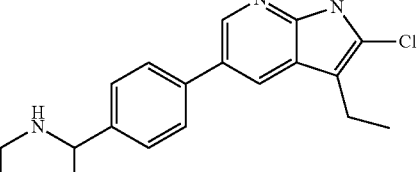 | 1-24 |
| 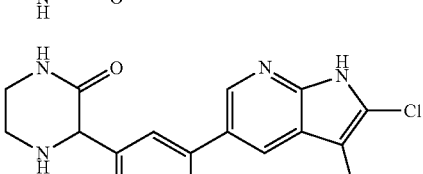 | 1-25 |
| 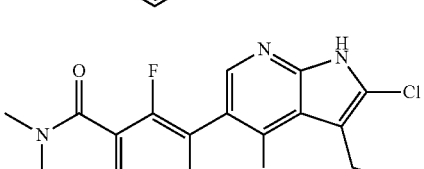 | 1-26 |
| 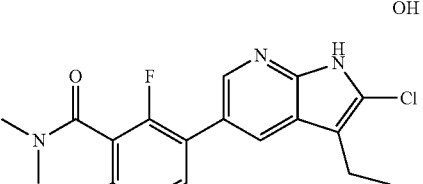 | 1-27 |

The invention also includes prodrugs, metabolites, derivatives, and pharmaceutically acceptable salts of compounds of Formula I or Ia. Metabolites of the compounds of Formula I or Ia include compounds produced by a process comprising contacting a compound of Formula I or Ia with a mammal for a period of time sufficient to yield a metabolic product thereof.

If the compound of Formula I or Ia is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula I or Ia is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of Formula I or Ia can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The presently disclosed compounds can be formulated into pharmaceutical compositions along with a pharmaceutically acceptable carrier.

A pharmaceutical composition is formulated to be compatible with its intended route of administration. In some embodiments, the active compound(s) are delivered in a vesicle, such as liposomes (see, e.g., Langer (1990) *Science* 249:1527-33; and Treat et al., in *Liposomes in the Therapy of Infectious Disease and Cancer*, Lopez Berestein and Fidler (eds.), Liss, N.Y., pp. 353-65, 1989).

In yet another embodiment, the active compound(s) can be delivered in a controlled release system. In one example, a pump can be used (see, e.g., Langer (1990) *Science* 249:1527-33; Sefton (1987) *Crit. Rev. Biomed. Eng.* 14:201-40; Buchwald et al. (1980) *Surgery* 88:507-16; Saudek et al. (1989) *N. Engl. J. Med.* 321:574-79). In another example, polymeric materials can be used (see, e.g., Levy et al. (1985) *Science* 228:190-92; During et al. (1989) *Ann. Neurol.* 25:351-56; Howard et al. (1989) *J. Neurosurg.* 71:105-12). Other controlled release systems, such as those discussed by Langer (1990) *Science* 249:1527-33, can also be used.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor® EL (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound(s) into a sterile vehicle that contains a basic dispersion medium and the required other ingredients from those enumerated above. In the case of sterile powders for the preparation of sterile injectable solutions, the methods of preparation can include vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound(s) can be incorporated with excipients and used in the form of tablets, troches, or capsules. Oral compositions can also be prepared using a fluid carrier for use as a mouthwash, wherein the compound(s) in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compound(s) are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound(s) are formulated into ointments, salves, gels, or creams as generally known in the art. The compound(s) can also be prepared in the form of suppositories (e.g., with conventional suppository bases such as cocoa butter and other glycerides) or retention enemas for rectal delivery.

In one embodiment, the active compound(s) are prepared with carriers that will protect the compound(s) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the compounds are dictated by and directly dependent on the unique characteristics of the active compound and the particular therapeutic effect to be achieved, and the limitations inherent in the art of compounding such an active compound for the treatment of subjects.

In particular embodiments the pharmaceutical composition comprising the presently disclosed compounds further comprise a chemotherapeutic agent. In some of these embodiments, the chemotherapeutic agent is an immunotherapeutic agent.

Methods

The presently disclosed compounds find use in inhibiting the activity of the enzyme HPK1. HPK1, also referred to as mitogen activated protein kinase kinase kinase kinase 1 or MAP4K1, is a member of the germinal center kinase subfamily of Ste20-related serine/threnonine kinases. HPK1 functions as a MAP4K by phosphorylating and activating MAP3K proteins, including MEKK1, MLK3 and TAK1, leading to the activation of the MAPK Jnk.

HPK1 polynucleotides and polypeptides are known in the art (Hu et al. (1996) *Genes Dev.* 10: 2251-2264, which is herein incorporated by reference in its entirety). Non-limiting examples of HPK1 polynucleotides and polypeptides comprise the human HPK1 polynucleotide as set forth in SEQ ID NO: 1 (nucleotides 141-2642 of GenBank Accession No. NM_007181.5) and the encoded human HPK1 polypeptide (Accession No. NP_009112.1) as set forth in SEQ ID NO: 2. A shorter 821 amino acid isoform of HPK1 exists in humans, the coding sequence and amino acid sequence of which is set forth in SEQ ID NOs: 3 and 4, respectively (nucleotides 141-2606 of GenBank Accession No. NM_001042600.2 and GenBank Accession No. NP_001036065.1, respectively).

HPK1 polypeptides comprise a variety of conserved structural motifs. For ease of reference, such motifs will be discussed as they relate to the longer human HPK1 isoform, which is set forth in SEQ ID NO:2, comprises 833 amino acid residues. HPK1 polypeptides comprise an amino-terminal Ste20-like kinase domain that spans amino acid residues 17-293, which includes the ATP-binding site from amino acid residues 23-46. The kinase domain is followed by four proline-rich (PR) motifs that serve as binding sites for SH3-containing proteins, such as CrkL, Grb2, HIP-55, Gads, Nck, and Crk. The four PR motifs span amino acid residues 308-407, 394-402, 432-443, and 468-477, respectively. HPK1 becomes phosphorylated and activated in response to TCR or BCR stimulation. TCR- and BCR-induced phosphorylation of the tyrosine at position 381, located between PR1 and PR2, mediates binding to SLP-76 in T cells or BLNK in B cells via a SLP-76 or BLNK SH2 domain, and is required for activation of the kinase. A citron homology domain found in the C-terminus of HPK1, approximately spanning residues 495-800, may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a presently disclosed compound (i.e., compound of Formula I or Ia or a pharmaceutically acceptable salt, prodrug, metabolite, or derivative thereof).

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of Formula I or Ia or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of $\gamma$-IFN$^+$ CD8 T cells. In some embodiments, the CD8 T cell is an antigen-specific T-cell.

In some embodiments, the antigen presenting cells in the subject have enhanced maturation and activation relative to prior to the administration of the compound of Formula I or Ia or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I or Ia or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) *J Cell Biol* 195(5):839-853).

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, $\gamma$-IFN) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

In some embodiments, administration of a compound of Formula I or Ia or a pharmaceutically acceptable salt, prodrug, metabolite, or derivative thereof to a subject results in an enhancement of T cell function.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., $\gamma$-interferon, IL-2, IL-12, and TNF$\alpha$), increased proliferation, increased antigen responsiveness (e.g., viral, pathogen, or tumor clearance) relative to such levels before the intervention, and increased effector granule production by CD8 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

Accordingly, the presently disclosed compounds of Formula I or Ia or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

"Immunogenecity" refers to the ability of a particular substance to provoke an immune response. Tumors are immunogenic and enhancing tumor immunogenicity aids in the clearance of the tumor cells by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula I or Ia or a pharmaceutically acceptable salt, prodrug, metabolite, or derivative thereof. In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

The presently disclosed compounds may be administered in any suitable manner known in the art. In some embodiments, the compound of Formula I or Ia or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula I or Ia or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In some embodiments, provided is a method for treating a cancer in a subject in need thereof comprising administering to the subject an effective amount of a compound of Formula I or Ia or a pharmaceutically acceptable salt, prodrug, metabolite, or derivative thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting the PI3K/AKT/mTOR pathway, HSP90 inhibitor, tubulin inhibitor, apoptosis inhibitor, and/or chemopreventative agent.

The additional therapy may be one or more of a chemotherapeutic agent. Thus, the method of treating cancer can comprise administering the presently disclosed HPK1 antagonists in conjunction with at least one chemotherapeutic agent.

As used herein, "in conjunction with" refers to administration of one treatment modality in addition to another treatment modality. As such, "in conjunction with" refers to administration of one treatment modality before, during, or after administration of the other treatment modality to the subject.

For example, the HPK1 antagonist and chemotherapeutic agent may be administered sequentially (at different times) or concurrently (at the same time). The HPK1 antagonist and chemotherapeutic agent may be administered by the same route of administration or by different routes of administration.

In certain embodiments, the HPK1 antagonist is administered in conjunction with another immunotherapy. For example, the HPK1 antagonist can be combined with a chemotherapeutic agent or biologic that targets the PDL1/PD1 pathway. A known inhibitory checkpoint pathway involves signaling through PD-1 receptors. The programmed-death 1 (PD-1) receptor and its ligands PD-L1 and PD-L2 are part of the same family of coregulatory molecules as CTLA-4.—See more at: http://www.onclive.com/web-exclusives/the-role-of-anti-pd-11-immunotherapy-in-cancer/2#sthash.cGfYa1T1.dpuf Chemotherapeutic agents or biologics that block PD-L1 binding to PD-1 and CD80 can prevent PD-L1-mediated inhibition/suppression of T-cell activation. Programmed cell death ligand-1 (PD-L1) is widely expressed on antigen-presenting cells (APC) and other immune cells. It is upregulated on tumor cells from a broad range of human cancers, and has been implicated with inhibition of antitumor T-cell immunity. PD-L1 is a cell surface protein that binds to the receptors PD-1 and CD80 on activated T cells, B cells, and other myeloid cells. PD-L1 binding to PD-1 on activated T-cells has been found to interfere with T-cell proliferation and inhibit immune responses. Overexpression of PD-L1 on cancer cells may allow these cells to avoid immune detection and elimination. High levels of PD-L1 expression on tumor cells have been associated with increased tumor aggressiveness and a poor prognosis. Chemotherapeutic agents or biologics that block PD-L1 binding to PD-1 include anti-PD-L1 antibodies, such as durvalumab, nivolumab, pidlizumab, MPDL3280A, MK-3475 and BMS-936559, among others.

In another example, the HPK1 antagonist can be combined with a chemotherapeutic agent or biologic that targets OX40 and its ligand, OX40L, are members of the TNF superfamily. OX40 is expressed on activated CD4(+) and CD8(+) T cells as well as on a number of other lymphoid and non-lymphoid cells. Costimulatory signals from OX40 to a conventional T cell promote division and survival, augmenting the clonal expansion of effector and memory populations as they are being generated to antigen. OX40 additionally suppresses the differentiation and activity of T-regulatory cells, further amplifying this process. OX40 and OX40L also regulate cytokine production from T cells, antigen-presenting cells, natural killer cells, and natural killer T cells, and modulate cytokine receptor signaling. As one of the most prominent costimulatory molecules known to control T cells, stimulating OX40 has been shown be a target for therapeutic immunization strategies for cancer. Certain OX40 agonists include GBR 830, and those disclosed in Linch, et al., Frontiers in Oncology, v. 5, pp. 1-10 (2015), herein incorporated by reference in its entirety.

In some embodiments, the invention also provides compounds of Formula I or Ia described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of Formula I or Ia described herein or pharmaceutical compositions described herein for use in a method for inhibiting HPK1 as described herein.

In some embodiments, the invention also provides compounds of Formula I or Ia described herein or pharmaceutical compositions described herein for use in a method for enhancing an immune response in a subject in need thereof as described herein.

In some embodiments, the invention also provides compounds of Formula I or Ia described herein or pharmaceutical compositions described herein for use in a method for treating a HPK1-dependent disorder as described herein.

In some embodiments, the invention also provides the use of a compound of Formula I or Ia described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of Formula I or Ia described herein or a pharmaceutical composition described herein for the manufacture of a medicament for inhibiting HPK1.

In some embodiments, the invention also provides the use of a compound of Formula I or Ia described herein or a pharmaceutical composition described herein for the manufacture of a medicament for enhancing an immune response in a subject in need thereof.

In some embodiments, the invention also provides the use of a compound of Formula I or Ia described herein or a pharmaceutical composition described herein for the manufacture of a medicament treating a HPK1-dependent disorder.

In some embodiments, the invention also provides the use of compounds of Formula I or Ia described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of Formula I or Ia described herein or pharmaceutical compositions described herein in a method for inhibiting HPK1 as described herein.

In some embodiments, the invention also provides the use of compounds of Formula I or Ia described herein or pharmaceutical compositions described herein in a method for enhancing an immune response in a subject in need thereof as described herein.

In some embodiments, the invention also provides the use of compounds of Formula I or Ia described herein or pharmaceutical compositions described herein in a method for treating a HPK1-dependent disorder as described herein.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPK1 antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered a HPK1 antagonist is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for cancer may be a person demonstrating symptoms of cancer, one that has been diagnosed with cancer, a subject that is in remission from cancer, or a subject having an increased risk for developing cancer (e.g., a genetic predisposition, certain dietary or environmental exposures).

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The following examples are offered by way of illustration and not by way of limitation.

EXAMPLES

Method A: Experiments performed on an Agilent 1100 HPLC with Agilent MSD mass spectrometer using ESI as ionization source using an Agilent ZORBAX SB—C18 100×3.0 mm column and a 0.7 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 25.5 minutes. The final solvent system was held constant for a further 2.5 minutes.

Method B: Experiments performed on an Agilent 1100 HPLC with Agilent MSD mass spectrometer using ESI as ionization source using an Agilent ZORBAX SB—C18 30×2.1 mm column and a 0.4 ml/minute flow rate. The solvent system was a gradient starting with 97% water with 0.05% TFA (solvent A) and 3% acetonitrile with 0.05% TFA (solvent B), ramping up to 5% solvent A and 95% solvent B over 7 minutes. The final solvent system was held constant for a further 1.5 minute.

Method C: Experiments performed on a Waters Acquity UHPLC with Waters—LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 2.5 minutes. The final solvent system was held constant for a further 0.5 minute.

Method D: Experiments performed on a HP1100 (quaternary pump/PDA detector)+ZQ Mass Spectrometer. Column: Phenomenex Luna C18(2) 3μ, 30×4.6 mm column with a 2 mL/minute flow rate. The solvent system was a gradient starting with 95% water with 0.1% $HCO_2H$ (solvent A) and 5% acetonitrile with 0.1% $HCO_2H$ (solvent B), ramping up to 5% solvent A and 95% solvent B over 4 minutes. The final solvent system was held constant for a further 1 minute. Detectors: UV, diode array 190-450 nm; MS, mass 160-1000 (or 100-800, or 160-1300) in ES+& ES− (200 μl/min split to MS).

Method E: Experiments performed on an Acquity UPLC (binary pump/PDA detector)+ZQ Mass Spectrometer: Column: ACQUITY UPLC BEH C18 1.7 μm, 100×2.1 mm, maintained at 40° C. with a 0.4 mL/min flow rate. The solvent system was a gradient starting with 95% water with 0.1% $HCO_2H$ (solvent A) and 5% acetonitrile with 0.1% $HCO_2H$ (solvent B), ramping up to 5% solvent A and 95% solvent B over 5.6 minutes. The final solvent system was held constant for a further 0.8 minute. Detectors: UV, diode array 200-500 nm; MS, mass 100-800 (or −1500) in ES+& ES− (no split to MS).

Methods for Biological evaluation to assess compound inhibition of HPK-1:

Materials:

| Reagent | Vender-Cat# |
| --- | --- |
| white ProxiPlate 384 F (assay plate) | PerkinElmer-6008289 |
| 384-well Microplate (compound plate) | Labcyte-LP-0200 |
| HPK1 enzyme | Signalchem-M23-11G |
| Tracer-222 | Invitrogen-PV6121 |
| Eu-Anti-GST Ab | Invitrogen-PV5594 |

-continued

| Reagent | Vender-Cat# |
|---|---|
| Assay Buffer | 2 mM DTT (Sigma-43815), 0.01% BRIJ-35 (Sigma-B4184), 10 mM MgCl2, 50 mM HEPES (Invitrogen-15630130) |

Procedure:
I. Compound Dilution:
1. Prepare 12.5 uL/well of 5 mM of compounds (100×) to column 2 and column 13 & 10 ul/well DMSO in column 3-12, 14-23 and well A1-H1, I24-P24 of compound plate with Bravo. For reference compound, the top concentration is 1 mM
2. Add 10 ul 2 mM staurosporine in well J1-P1 and A24-H24
3. Perform 11 point 5-fold compound serial dilution with Bravo
   a. transfer 2.5 ul compounds from column 2 and column 13 to 10 ul of DMSO in column 3 and column 14 & so on
4. Centrifuge the compound plate at 2500 rpm for 1 min
5. Transfer 80 nl compounds into assay plate using Echo. One compound plate makes two assay plates
6. Seal the assay plate and store in N2 cabinet.
II. Assay Condition:
2 nM HPK1, 2 nM Eu-Anti-GST Ab, 15 nM Tracer222, 60 min incubation
III. HPK Lantha Binding Assay:
1. Add 4 ul 2×HPK1 and Eu-anti-GST antibody into each well of assay plate using Multidrop
2. Incubate at 23 C incubator for 1 h
3. Add 4 ul 2× Tracer-222 into each well of assay plate using Multidrop
4. Incubate at 23 C incubator for 1 h
5. Read the assay plate in Envision
   a. TR_FRET, 340 ex/615 and 665 em
   b. 100 usec Delay, 200 usec integration
IV. Analysis:
1. Compound Ki was analyzed using Morrison ki fit model in XL-fit
   a. fit=(1−((((E+x)+(Ki*(1±(S/Kd))))−(((((E+x)+(Ki*(1+(S/Kd))))^2)−((4*E)*x))^0.5))/(2*E)))
      res=(y-fit)
   b. Parameters:
      E=enzyme concentration
      S=Tracer222 concentration, Kd=Tracer222 Kd
      All in the same units (uM)
V. Automation:
Compound dilution: Bravo
Compound transfer: Echo
Assay buffer: Multidrop
I. Preparation of Compounds Intermediate 1: 4-(3-bromophenyl)morpholin-3-one

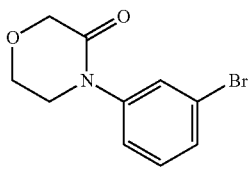

To a solution of morpholin-3-one (500 mg, 4.95 mmol) in 1,4-dioxane (50 ml) was added 1,3-dibromobenzene (1.28 g, 5.44 mmol), palladium(II) acetate (106 mg, 0.47 mmol), Xantphos (407 mg, 0.71 mmol) and $Cs_2CO_3$ (3.1 g, 9.53 mmol). The reaction mixture was stirred at 100° C. for 16 hours under $N_2$. After 16 h, the reaction mixture was cooled to room temperature, concentrated in vacuo and the crude product was purified via flash chromatography on silica gel (0-30% ethyl acetate in petroleum ether) to provide 4-(3-bromophenyl)morpholin-3-one (820 mg, 65% yield) as a pale-yellow solid. LCMS (ESI) $[M+H]^+$=256.0.

Intermediate 2: 4-(3-(4,4,5,5-tetramethyl-1,3,2-dioxaborolan-2-yl)phenyl)morpholin-3-one

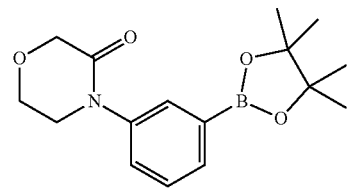 [SMILES: CC1(C)OB(c2cccc(N3CCOCC3=O)c2)OC1(C)C]

To a solution of 4-(3-bromophenyl)morpholin-3-one (820 mg, 3.2 mmol) in 1,4-dioxane (50 ml) was added bis(pinacolato)diboron (1.2 g, 4.80 mmol), potassium acetate (0.9 g, 9.61 mmol) and $Pd(dppf)Cl_2$ (260 mg, 0.32 mmol). The mixture was stirred at 100° C. for 4 h under $N_2$. After 4 h, the reaction mixture was concentrated in vacuo and the crude product was purified via flash chromatography on silica gel (10-80% ethyl acetate in petroleum ether) to provide 4-[3-(4,4,5,5-tetramethyl-1,3,2-dioxaborolan-2-yl)phenyl]morpholin-3-one as pale-yellow solid (1.0 g, 86% yield). LCMS (ESI) $[M+H]^+$=304.2.

Intermediate 3: 3-amino-N,N-dimethylpicolinamide

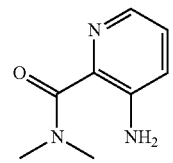

To a solution of 3-aminopicolinic acid (1.8 g, 13.03 mmol) in dichloromethane (40 ml) was added N,N-dimethylamine (760.0 mg, 16.94 mmol), HATU (6.2 g, 16.29 mmol) and $Et_3N$ (5.3 ml, 39.10 mmol). The mixture was stirred at room temperature for 2 h. After 2 h, the reaction mixture was concentrated in vacuo and the crude was then purified via flash chromatography on silica gel (100% ethyl acetate) to afford 3-amino-N,N-dimethylpicolinamide (1.5 g, 69% yield). LCMS (ESI) $[M+H]^+$=166.1.

Intermediate 4: 3-amino-6-iodo-N,N-dimethylpicolinamide

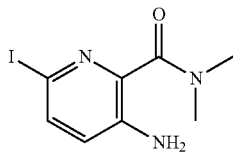

To a solution of 3-amino-N,N-dimethylpicolinamide (1.2 g, 7.26 mmol) in 1,2-dichloroethane (10 ml) was added N-iodosuccinimide (1.9 g, 8.72 mmol). The mixture was stirred at room temperature for 3 h. After 3 h, the reaction mixture was concentrated in vacuo and the crude was then purified via flash chromatography on silica gel (0-20% ethyl acetate in petroleum ether) to afford 3-amino-6-iodo-N,N-dimethylpicolinamide (0.9 g, 42.0% yield). LCMS (ESI) [M+H]$^+$=292.0.

Intermediate 5: 4-(6-bromopyridin-2-yl)morpholin-3-one

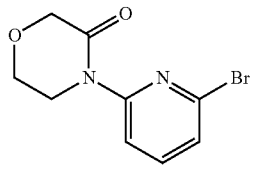 [SMILES: O=C1COCCN1c1cccc(Br)n1]

To a solution of morpholin-3-one (500 mg, 4.95 mmol) in 1,4-dioxane (50 ml) was added 2,6-dibromopyridine (1.52 g, 6.43 mmol), palladium(II) acetate (105 mg, 0.47 mmol), Xantphos (407 mg, 0.71 mmol) and Cs$_2$CO$_3$ (3.1 g, 9.42 mmol). The reaction mixture was stirred at 100° C. for 16 h under N$_2$. After 16 h, the reaction mixture was cooled to temperature, concentrated in vacuo and the crude product was purified via flash chromatography on silica gel (0-30% ethyl acetate in petroleum ether) to provide 4-(6-bromopyridin-2-yl)morpholin-3-one (350 mg, 27% yield) as a pale-yellow solid. LCMS (ESI) [M+H]$^+$=257.0.

Intermediate 6: (3-amino-6-chloropyridin-2-yl)(3-hydroxyazetidin-1-yl)methanone

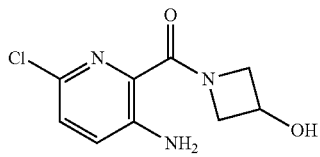

To a solution of 3-amino-6-chloropicolinic acid (860 mg, 4.98 mmol) in dichloromethane (50 ml) was added azetidin-3-ol hydrochloride (580 mg, 5.29 mmol), HATU (2.27 g, 5.98 mmol) and Et$_3$N (1.5 g, 14.95 mmol). The reaction mixture was stirred at 20° C. for 2 h. After 2 h, the reaction mixture was concentrated in vacuo and the crude product was purified via flash chromatography on silica gel (0-50% ethyl acetate in petroleum ether) to provide (3-amino-6-chloropyridin-2-yl)(3-hydroxyazetidin-1-yl)methanone (1.1 g, 73% yield) as a yellow solid. LCMS (ESI) [M+H]$^+$=228.0.

Intermediate 7: 1,1,1-trifluoro-2-(2-fluoropyridin-3-yl)-3-nitrobutan-2-ol

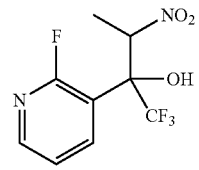

To cooled solution (0° C.) of diisopropylamine (42.5 mL, 302.4 mmol) in tetrahydrofuran (450 mL) was added n-BuLi (112.mL, 280 mmol) dropwise. The reaction mixture was stirred at this temperature for 30 min, then cooled to −75° C. 2-Fluoropyridine (20 mL, 231 mmol) was added dropwise and stirred at this temperature for 4 h. To the resulting suspension was added ethyl trifluoroacetate (39 mL, 326 mmol) while ensuring the temperature did not rise above −45° C. The reaction mixture was warmed to room temperature, nitroethane (33 mL, 461 mmol) was added, and the reaction was stirred overnight. The solution was poured into 2N aqueous hydrochloric acid (1.5 L), and the mixture was extracted with ethyl acetate (2×500 mL). The combined organic layers were washed with brine (200 mL), dried over sodium sulfate and concentrated to dryness in vacuo. The resulting residue was purified by column chromatography (silica gel, petroleum ether/ethyl acetate=20/1 to 10/1, TLC: petroleum ether/ethyl acetate=3/1, Rf=0.5) to afford the crude product as a yellow solid, which was washed with petroleum ether (100 mL×3) to afford 1,1,1-trifluoro-2-(2-fluoro-3-pyridyl)-3-nitrobutan-2-ol (14.6 g, 47.365 mmol, 20% yield) as a white solid. LCMS: m/z=269.1 [M+1]. $^1$H NMR (400 MHz, DMSO-d$_6$): δ 8.39-8.17 (m, 3H), 7.60-7.56 (m, 1H), 5.74 (q, J=6.8 Hz, 1H), 1.31 (d, J=7.2 Hz, 3H).

Intermediate 8: 3-amino-1,1,1-trifluoro-2-(2-fluoro-pyridin-3-yl)butan-2-ol

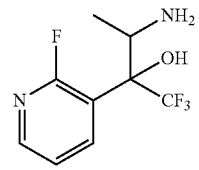 [SMILES: CC(N)C(O)(c1cccnc1F)C(F)(F)F]

To a solution of 1,1,1-trifluoro-2-(2-fluoro-3-pyridyl)-3-nitrobutan-2-ol (1.0 g, 3.73 mmol) in acetic acid (20 mL) was added iron powder (1.05 g, 18.75 mmol) at 60° C. The reaction was stirred at 60° C. for 0.5 h. The reaction was diluted with ethyl acetate (100 mL), filtered and concentrated to afford crude 3-amino-1,1,1-trifluoro-2-(2-fluoro-3-pyridyl)butan-2-01 (0.88 g, 3.69 mmol, 99.1% yield) as a brown solid, which was used in next step directly. LCMS: m/z=239.1 [M+1].

Intermediate 9: 2-methyl-3-(trifluoromethyl)-2,3-dihydro-1H-pyrrolo[2,3-b]pyridin-3-ol

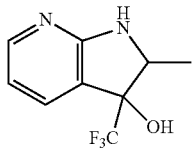

A mixture of 3-amino-1,1,1-trifluoro-2-(2-fluoro-3-pyridyl)butan-2-ol (0.88 g, 3.69 mmol) and triethylamine (6.mL, 42.69 mmol) in ethanol (30 mL) was stirred at 90° C. for 2 day. The reaction was concentrated and directly purified by column chromatography (silica gel, dichloromethane/methanol=30/1 to 10/1, TLC: dichloromethane/methanol=10/1, Rf=0.5) to afford 2-methyl-3-(trifluoromethyl)-2,3-dihydro-1H-pyrrolo[2,3-b]pyridin-3-ol (450 mg, 2.06 mmol, 55.8% yield) as a brown oil. LCMS: m/z=219.1 [M+1]

Intermediate 10: 5-bromo-2-methyl-3-(trifluoromethyl)-2,3-dihydro-1H-pyrrolo[2,3-b]pyridin-3-ol

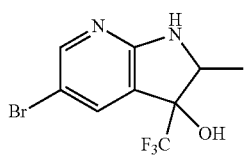

To a solution of 2-methyl-3-(trifluoromethyl)-1,2-dihydropyrrolo[2,3-b]pyridin-3-ol (425.0 mg, 1.95 mmol) in acetonitrile (20 mL) was added N-bromosuccinimide (22.0 mg, 0.12 mmol) at 15° C. The reaction mixture was stirred at 15° C. for 1 h. The reaction was quenched by adding a saturated solution of $Na_2S_2O_3$. The reaction was purified directly by column chromatography (silica gel, dichloromethane/methanol=20/1, TLC: dichloromethane/methanol=10/1, Rf=0.5) to afford 55-bromo-2-methyl-3-(trifluoromethyl)-2,3-dihydro-1H-pyrrolo[2,3-b]pyridin-3-ol (460 mg, 1.54 mmol, 79.5% yield) as a white solid. LCMS: m/z=299.0 [M+1].

Intermediate 11: 5-bromo-2-methyl-3-(trifluoromethyl)-1H-pyrrolo[2,3-b]pyridine

To a solution of 5-bromo-2-methyl-3-(trifluoromethyl)-1,2-dihydropyrrolo[2,3-b]pyridin-3-ol (200 mg, 0.67 mmol) and pyridine (0.11 mL, 1.36 mmol) in dichloromethane (10 mL) was added thionyl chloride (0.1 mL, 1.38 mmol) and stirred for 1 h. The reaction mixture was poured into sat. $NaHCO_3$(aq.) (50 mL), extracted with dichloromethane (30 mL×2), dried over $Na_2SO_4$ and purified by column chromatography (silica gel, petroleum ether/ethyl acetate=5/1 to 3/1, TLC:petroleum ether/ethyl acetate=3/1, Rf=0.5) to afford 5-bromo-2-methyl-3-(trifluoromethyl)-1H-pyrrolo[2,3-b]pyridine (80 mg, 0.29 mmol, 42.6% yield) as a white solid. LCMS: m/z=281.0 [M+1]. $^1$H NMR (400 MHz, DMSO-$d_6$): δ 12.64 (s, 1H), 8.35 (d, J=2 Hz, 1H), 8.06 (s, 1H), 2.53 (d, J=1.2 Hz, 3H).

Intermediate 12: 2-methyl-5-(4,4,5,5-tetramethyl-1,3,2-dioxaborolan-2-yl)-3-(trifluoromethyl)-1H-pyrrolo[2,3-b]pyridine

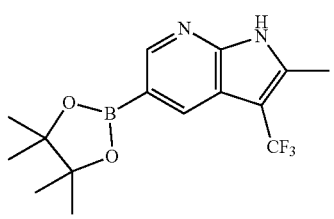

A mixture of 5-bromo-2-methyl-3-(trifluoromethyl)-1H-pyrrolo[2,3-b]pyridine (65 mg, 0.23 mmol), bis(pinacolato)diboron (91 mg, 0.36 mmol), potassium acetate (71 mg, 0.72 mmol) and Pd(dppf)$_2$Cl$_2$ (19 mg, 0.02 mmol) in 1,4-dioxane (6 mL) was stirred under nitrogen at 80° C. for 6 h. The reaction mixture was purified by column chromatography (silica gel, petroleum ether/ethyl acetate=10/1/0 to 3/1, petroleum ether/ethyl acetate=5/1, Rf=0.1) to afford 2-methyl-5-(4,4,5,5-tetramethyl-1,3,2-dioxaborolan-2-yl)-3-(trifluoromethyl)-1H-pyrrolo[2,3-b]pyridine (18 mg, 0.04 mmol, 19% yield) as a yellow solid. LCMS: m/z=327.1 [M+1].

Intermediate 13: 3-bromo-5-(4,4,5,5-tetramethyl-1,3,2-dioxaborolan-2-yl)aniline

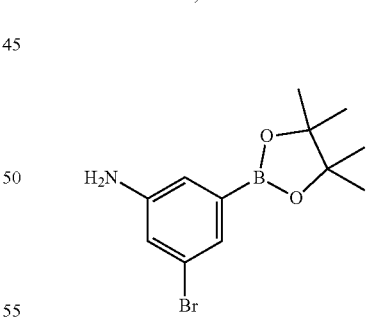

A mixture of 3,5-dibromoaniline (3.0 g, 12 mmol), bis(pinacolato)diboron (2.7 g, 11 mmol), potassium acetate (3.6 g, 36.68 mmol) and Pd(dppf)$_2$Cl$_2$ (540 mg, 0.66 mmol) in 1,4-dioxane (100 mL) was stirred under $N_2$ at 80° C. for 4 h. The reaction mixture was purified by column chromatography (silica gel, petroleum ether/ethyl acetate=8/1, petroleum ether/ethyl acetate=4/1, Rf=0.4) to afford 3-bromo-5-(4,4,5,5-tetramethyl-1,3,2-dioxaborolan-2-yl)aniline (1.57 g, 4.4 mmol, 37% yield) as a yellow oil. LCMS (ESI): [M+H]$^+$=342.1

Intermediate 14: (2-(3-amino-5-bromophenyl)pyridin-3-yl)methanol

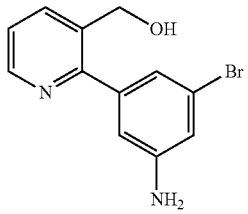 [SMILES: Nc1cc(Br)cc(-c2ncccc2CO)c1]

A mixture of (2-bromo-3-pyridinyl)methanol (2.2 g, 11.7 mmol), Pd(PPh$_3$)$_4$ (0.4 g, 0.35 mmol), K$_2$CO$_3$ (2.2 g, 16 mmol) and 3-bromo-5-(4,4,5,5-tetramethyl-1,3,2-dioxaborolan-2-yl)aniline (1.57 g, 4.37 mmol) in 1,4-dioxane (40 mL) and water (8 mL) was stirred under argon at 100° C. for 2 h. The reaction mixture was concentrated and purified directly by silica gel chromatography (petroleum ether/ethyl acetate=1/1 to 1/3) to afford (2-(3-amino-5-bromophenyl)pyridin-3-yl)methanol (1.0 g, 3.6 mmol, 82% yield) as a yellow solid. LCMS (ESI): [M+H]$^+$=281.0

Intermediate 15: (2-(3-amino-5-(4,4,5,5-tetramethyl-1,3,2-dioxaborolan-2-yl)phenyl)pyridin-3-yl)methanol

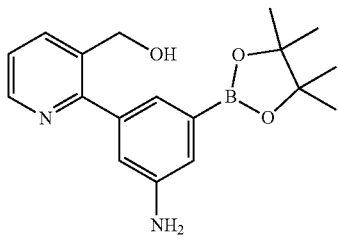 [SMILES: CC1(C)OB(c2cc(N)cc(-c3ncccc3CO)c2)OC1(C)C]

A mixture of [2-(3-amino-5-bromo-phenyl)-3-pyridyl]methanol (1.0 g, 3.08 mmol), bis(pinacolato)diboron (2.4 g, 9.45 mmol), potassium acetate (1.0 g, 10 mmol) and Pd(dppf)$_2$Cl$_2$ (250 mg, 0.31 mmol) in 1,4-dioxane (30 mL) was stirred under N$_2$ at 80° C. for 16 h. The reaction mixture was concentrated and purified by column chromatography (silica gel, petroleum ether/ethyl acetate=10/1/0 to 1/3, petroleum ether/ethyl acetate=1/3, Rf=0.2) to afford (2-(3-amino-5-(4,4,5,5-tetramethyl-1,3,2-dioxaborolan-2-yl)phenyl)pyridin-3-yl)methanol (0.8 g, 2.4 mmol, 80% yield) as a brown solid. LCMS (ESI): [M+H]$^+$=327.2 [M+1].

Intermediate 16: 5-bromo-3-iodo-1H-pyrrolo[2,3-b]pyridine

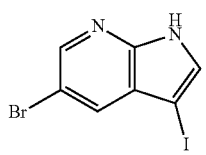 [SMILES: Brc1cnc2[nH]cc(I)c2c1]

To a solution of 5-bromo-1H-pyrrolo[2,3-b]pyridine (5.0 g, 25.38 mmol) in dichloromethane (400 mL) was added N-iodosuccinimide (6.28 g, 27.91 mmol). The mixture was stirred at 25° C. for 1 h. The product precipitated as a white solid. The solid was isolated by filtration and washed with acetone (50 mL) to give 5-bromo-3-iodo-1H-pyrrolo[2,3-b]pyridine (7.3 g, 22.61 mmol, 89% yield) as a white solid. LCMS (ESI) [M+H]$^+$=322.9.

Intermediate 17: 5-bromo-3-iodo-1-(p-tolylsulfonyl)pyrrolo[2,3-b]pyridine

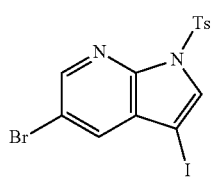 [SMILES: Cc1ccc(S(=O)(=O)n2cc(I)c3cc(Br)cnc32)cc1]

To a solution of 5-bromo-3-iodo-1H-pyrrolo[2,3-b]pyridine (7.3 g, 22.61 mmol) in tetrahydrofuran (140 mL) was added NaH (1.36 g, 33.91 mmol) at 25° C., the mixture was stirred at 25° C. for 0.5 h. Then, p-toluenesulfonyl chloride (4.74 g, 24.87 mmol) was added and stirred at 25° C. overnight. The mixture was diluted with sat.NaHCO$_3$ (100 mL) and extracted with ethyl acetate (3×250 mL). The combined extracts were washed with brine (3×100 mL), dried with Na$_2$SO$_4$, filtered and concentrated under reduced pressure to give crude 5-bromo-3-iodo-1-(p-tolylsulfonyl)pyrrolo[2,3-b]pyridine (10.3 g, 19.37 mmol, 86% yield) as a yellow solid. LCMS (ESI) [M+H]$^+$=478.9.

Intermediate 18: 5-bromo-1-(p-tolylsulfonyl)-3-vinylpyrrolo[2,3-b]pyridine

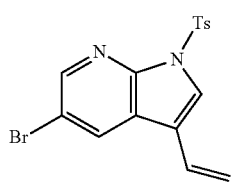 [SMILES: C=Cc1cn(S(=O)(=O)c2ccc(C)cc2)c2ncc(Br)cc12]

A mixture of 5-bromo-3-iodo-1-(p-tolylsulfonyl)pyrrolo[2,3-b]pyridine (7.0 g, 14.67 mmol), 4,4,5,5-tetramethyl-2-vinyl-1,3,2-dioxaborolane (4.52 g, 29.34 mmol), potassium carbonate (4.06 g, 29.34 mmol) and tetrakis(triphenylphosphine)palladium(0) (0.85 g, 0.73 mmol) in 1,4-dioxane (210 mL) and water (20 mL) was stirred overnight under argon at 60° C. The mixture was concentrated and purified by column chromatography eluting with ethyl acetate/hexane=1:6 to afford 5-bromo-1-(p-tolylsulfonyl)-3-vinylpyrrolo[2,3-b]pyridine (5.1 g, 9.7 mmol, 66% yield) as a white solid. LCMS (ESI) [M+H]$^+$=378.9.

Intermediate 19: 2-[5-bromo-1-(p-tolylsulfonyl) pyrrolo[2,3-b]pyridin-3-yl]ethanol

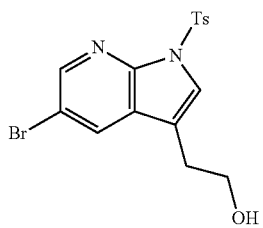 [SMILES: Cc1ccc(S(=O)(=O)n2cc(CCO)c3cc(Br)cnc32)cc1]

To a solution of 5-bromo-1-(p-tolylsulfonyl)-3-vinyl-pyrrolo[2,3-b]pyridine (5.1 g, 9.73 mmol) in tetrahydrofuran (100 mL) was added borane-dimethyl sulfide complex (3.7 g, 48.67 mmol) and hydrogen peroxide (10 mL, 30 wt % in water) at 0° C. The mixture was stirred at 0° C. for 1.5 h. A solution of NaOH (0.78 g, 19.47 mmol) in water (20 mL) was added and the resulting reaction mixture was stirred at room temperature for 2 h. The mixture was extracted with ethyl acetate (3×200 mL). The combined extracts were washed with brine (100 mL), dried with $Na_2SO_4$, filtered and evaporated under reduced pressure. The residue was purified by column chromatography eluting with ethyl acetate/hexane=1:2 to afford 2-[5-bromo-1-(p-tolylsulfonyl) pyrrolo[2,3-b]pyridin-3-yl]ethanol (2.5 g, 5.99 mmol, 61% yield) as a white solid. LCMS (ESI) $[M+H]^+$=397.0.

Intermediate 20: 5-Bromo-2-chloro-1-(toluene-4-sulfonyl)-3-vinyl-1H-pyrrolo[2,3-b]pyridine

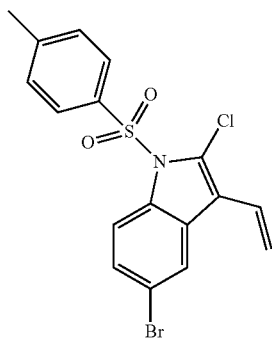 [SMILES: C=Cc1c(Cl)n(S(=O)(=O)c2ccc(C)cc2)c2ccc(Br)cc12]

Lithium diisopropylamide (2.0 M in tetrahydrofuran/heptane/ethylbenzene, 0.88 mL, 1.77 mmol) was added dropwise to a stirred solution of 5-bromo-1-(toluene-4-sulfonyl)-3-vinyl-1H-pyrrolo[2,3-b]pyridine (555 mg, 1.47 mmol) in anhydrous tetrahydrofuran (7 mL), under nitrogen, at −78° C. After 45 min, a solution of benzenesulfonyl chloride (0.226 mL, 1.77 mmol) in anhydrous tetrahydrofuran (3 mL) was added dropwise. Once the addition was complete, the solution was allowed to warm to RT and stirred for 18 h. The resulting suspension was partitioned between ethyl acetate and saturated $NaHCO_{3(aq)}$, the organic layer separated, washed with brine, dried ($Na_2SO_4$) and evaporated to give a yellow solid. Trituration with DCM gave the title compound as pale yellow solid (203 mg). Evaporation of the mother liquors and column chromatography (0-20% ethyl acetate/cyclohexane) gave further product as a pale yellow solid (360 mg-93% overall yield). LCMS (ESI) $[M+H]^+$=411.2. 5-Bromo-1-(toluene-4-sulfonyl)-3-vinyl-1H-pyrrolo[2,3-b]pyridine was present as a 20-30% impurity.

Intermediate 21: 2-[5-Bromo-2-chloro-1-(toluene-4-sulfonyl)-1H-pyrrolo[2,3-b]pyridin-3-yl]ethanol

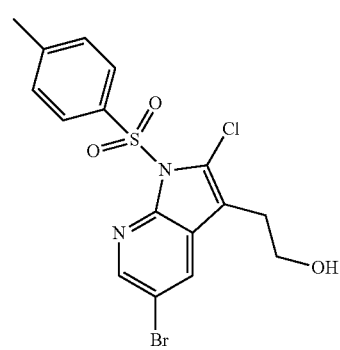 [SMILES: Cc1ccc(S(=O)(=O)n2c(Cl)c(CCO)c3cc(Br)cnc32)cc1]

Borane (1M tetrahydrofuran complex, 1.03 mL, 1.03 mmol) was added dropwise to a stirred solution of 5-bromo-2-chloro-1-(toluene-4-sulfonyl)-3-vinyl-1H-pyrrolo[2,3-b]pyridine (355 mg, 0.862 mmol) in anhydrous tetrahydrofuran (10 mL), under nitrogen, at 0° C. The solution was allowed to warm to room temperature after 1 h and stirred for a further 1 h. The mixture was cooled to 0° C., $NaOH_{(aq)}$ (1 M. 1.29 mL, 1.29 mmol) and hydrogen peroxide (30% in water, 0.262 mL, 2.59 mmol) added. The mixture was allowed to warm to RT after 15 min and stirred for a further 1 h. The resulting mixture was partitioned between ethyl acetate and saturated $NH_4Cl_{(aq)}$, the organic layer separated, dried ($Na_2SO_4$) and evaporated to give a yellow oil. Purification by column chromatography (0-50% ethyl acetate/cyclohexane) gave the title compound (103 mg, 28% yield) as a white solid. LCMS (ESI) $[M+H]^+$=429.2

Intermediate 22: 6-Amino-2-fluoro-N,N-dimethyl-3-(4,4,5,5-tetramethyl-[1,3,2]dioxaborolan-2-yl)benzamide

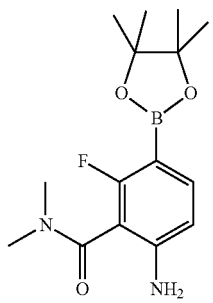

Step 1. 6-Amino-3-bromo-2-fluorobenzoic acid

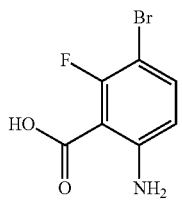

A suspension of 2-amino-6-fluorobenzoic acid (6 g, 38.7 mmol) in chloroform (80 mL) was cooled in ice. Bromine (2.19 mL, 42.6 mmol) was added dropwise and the mixture was stirred at 0° C. for 0.5 h, then at room temperature for 16 h. The solid was filtered, washed with a little dichloromethane and dried under vacuum at 40° C. to give the title compound (12.29 g). Analysis by LCMS (Method D) showed some residual starting material ($R_T$ 2.12 min), dibromo product ($R_T$ 3.34 min, [MH–CO$_2$]$^-$ 268) and a minor bromo isomer ($R_T$ 2.88 min) in addition to the desired product ($R_T$ 2.80 min, [MH–H$_2$O]$^+$ 216/218). The material was used without further purification.

Step 2. 6-Amino-3-bromo-2-fluoro-N,N-dimethylbenzamide

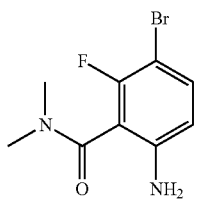

N,N-diisopropylethylamine (16.4 mL, 96 mmol) was added to a suspension of crude product from step 1 (10.28 g) in dry dichloromethane (100 mL) to give a solution. HATU (18.2 g, 48 mmol) was added and the mixture was stirred for 5 min before addition of dimethylamine (2M in tetrahydrofuran, 24.0 mL, 48 mmol) with cooling in a cold water-bath. The mixture was stirred at room temperature for 3 h, and then washed with 1M sodium hydroxide and brine. The aqueous phases were re-extracted twice with dichloromethane. The combined organic phases were dried (Na$_2$SO$_4$) and evaporated. The residue was chromatographed on 300 g silica eluting with 0-50% ethyl acetate/cyclohexane to give a mixture of the title compound (4.79 g) containing some unbrominated analogue. This material was further purified by chromatography (200 g silica, 0-50% ethyl acetate/cyclohexane) to give a 1.5:1 mixture of title compound and unbrominated analogue (3.55 g). LCMS (Method D): $R_T$: 2.64 min, (ESI) [M+H]$^+$=261; unbrominated $R_T$: 2.11 min, (ESI) [M+H]$^+$=183.

Step 3. 6-Amino-2-fluoro-N,N-dimethyl-3-(4,4,5,5-tetramethyl-[1,3,2]dioxaborolan-2-yl)benzamide

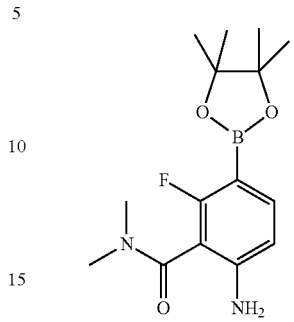

A mixture of the product mixture from Step 2 (3.47 g), bis(pinacolato)diboron (6.76 g, 26.6 mmol), [1,1'-bis(diphenylphosphino)ferrocene]dichloropalladium (II) chloride (dichloromethane complex, 1.09 g, 1.33 mmol) and potassium acetate (3.86 g, 39.9 mmol) in DMF (25 mL) was purged with argon and heated at 100° C. for 3 h. The cooled mixture was filtered through Celite, washing thoroughly with ethyl acetate, and the filtrate was evaporated to a small volume. The residue was dissolved in ethyl acetate and water, passed through Celite again and the phases were separated. The aqueous phase was extracted with ethyl acetate 3 times. Organic fractions were dried (Na$_2$SO$_4$) and evaporated. The residue was chromatographed on 200 g silica eluting with 50-100% ethyl acetate/cyclohexane to give a 2.8:1 mixture of the title compound and unbrominated material (as seen in Step 2) (2.12 g). LCMS (Method D): title compound $R_T$: 2.91 min, (ESI) [M+H]$^+$=309; unbrominated $R_T$: 2.09 min, (ESI) [M+H]$^+$=183. $^1$H NMR (400 MHz, CDCl$_3$) δ 1.32 (12H, s), 2.99 (3H, s), 2.10 (3H, s), 4.52 (2H, broad s), 6.47 (1H, d, J=8 Hz), 7.51 (1H, dd, J=8 & 7 Hz).

Example 1: Compound 1-1

4-(3-(2-chloro-3-ethyl-1H-pyrrolo[2,3]pyridin-5-yl)phenyl)morpholin-3-one

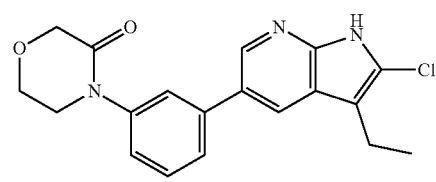 [SMILES: CCc1c(Cl)[nH]c2ncc(-c3cccc(N4CCOCC4=O)c3)cc12]

Step 1: 5-bromo-3-ethyl-1H-pyrrolo[2,3-b]pyridin-2(3H)-one

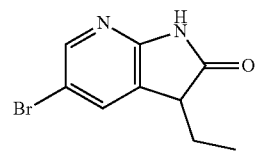

To a solution of 5-bromo-3-ethyl-1H-pyrrolo[2,3-b]pyridine (500 mg, 2.22 mmol) in acetonitrile (25 mL) was added NCS (325 mg, 2.44 mmol). The mixture was stirred at 40° C. for 6 h. After 6 h, the reaction mixture was washed with water (30 ml) and extracted with ethyl acetate (3×100 ml). The combined organic extracts were dried over Na$_2$SO$_4$, filtered and concentrated in vacuo. The crude product was then purified via flash chromatography on silica gel (0-50% ethyl acetate in petroleum ether) to provide 5-bromo-3-ethyl-1H-pyrrolo[2,3-b]pyridin-2(3H)-one (350 mg, 1.21 mmol, 54% yield) as a white solid. LCMS (ESI) [M+H]$^+$= 241.1.

Step 2: 5-bromo-2-chloro-3-ethyl-1H-pyrrolo[2,3-b]pyridine

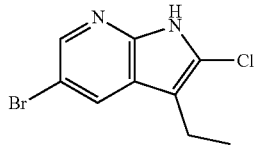

A solution of 5-bromo-3-ethyl-1H-pyrrolo[2,3-b]pyridin-2(3H)-one (200 mg, 0.83 mmol) in phosphorus oxychloride (4.0 mL, 43.57 mmol) was stirred at 100° C. for 16 h. The reaction mixture was slowly poured into 200 ml of water, and then neutralized to pH 8.0 with saturated Na$_2$CO$_3$ aqueous solution. The resultant mixture was extracted with dichloromethane (3×100 ml). The combined organic extracts were dried over Na$_2$SO$_4$, filtered and concentrated in vacuo. The crude product was then purified via flash chromatography on silica gel (0-30% ethyl acetate in petroleum ether) to provide 5-bromo-2-chloro-3-ethyl-1H-pyrrolo[2,3-b]pyridine (200 mg, 0.74 mmol, 89% yield) as a white solid. LCMS (ESI) [M+H]$^+$=259.0; $^1$H NMR (400 MHz, CD$_3$OD) δ 8.21 (d, J=2.0 Hz, 1H), 8.09 (d, J=2.0 Hz, 1H), 2.74 (q, J=7.2 Hz, 2H), 1.24 (t, J=7.2 Hz, 3H).

Step 3: 4-(3-(2-chloro-3-ethyl-1H-pyrrolo[2,3-b]pyridin-5-yl)phenyl)morpholin-3-one

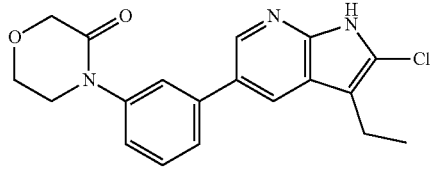 [SMILES: CCc1c(Cl)[nH]c2ncc(-c3cccc(N4CCOCC4=O)c3)cc12]

To a sealed tube was added 5-bromo-2-chloro-3-ethyl-1H-pyrrolo[2,3-b]pyridine (50 mg, 0.19 mmol), 4-[3-(4,4,5,5-tetramethyl-1,3,2-dioxaborolan-2-yl)phenyl]morpholin-3-one (58 mg, 0.19 mmol), Pd(dppf)Cl$_2$.CH$_2$Cl$_2$ (15 mg, 0.02 mmol), Cs$_2$CO$_3$ (188 mg, 0.58 mmol), 1,4-dioxane (1 ml) and water (0.5 ml). The reaction mixture was stirred at 100° C. for 4 h. The reaction mixture was then filtered and the filtrate was concentrated in vacuo. The crude product was purified via flash chromatography on silica gel (dichloromethane/methanol 50:1-10:1) to afford a yellow solid, which was further purified by preparative reverse phase HPLC to provide 4-[3-(2-chloro-3-ethyl-1H-pyrrolo[2,3-b]pyridin-5-yl)phenyl]morpholin-3-one (35.0 mg, 51% yield) as a white solid. LCMS (ESI): R$_T$ (min)=1.463, [M+H]$^+$ =356.1, method=C; $^1$H NMR (400 MHz, CD$_3$OD) δ 8.44 (s, 1H), 8.10 (s, 1H), 7.70 (s, 1H), 7.65 (d, J=7.2 Hz, 1H), 7.58 (t, J=7.2 Hz, 1H), 7.38 (d, J=7.2 Hz, 1H), 4.34 (s, 2H), 4.11-4.08 (m, 2H), 3.89-3.87 (m, 2H), 2.82 (q, J=6.0 Hz, 2H), 1.29 (t, J=6.0 Hz, 3H).

Example 2: Compound 1-2

3-amino-6-(2-chloro-3-ethyl-1H-pyrrolo[2,3-b]pyridin-5-yl)-N,N-dimethylpicolinamide

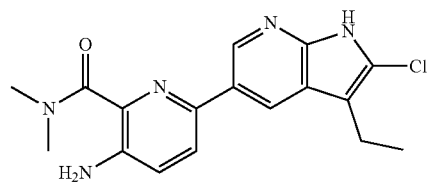

Step 1: 2-chloro-3-ethyl-5-(4,4,5,5-tetramethyl-1,3,2-dioxaborolan-2-yl)-1H-pyrrolo[2,3-b]pyridine

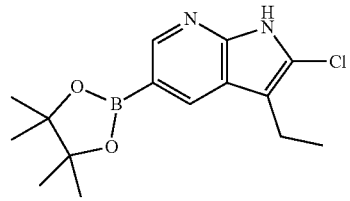 [SMILES: CCc1c(Cl)[nH]c2ncc(B3OC(C)(C)C(C)(C)O3)cc12]

To a sealed tube was added 5-bromo-2-chloro-3-ethyl-1H-pyrrolo[2,3-b]pyridine (50.0 mg, 0.19 mmol), bis(pinacolato)diboron (73 mg, 0.29 mmol), Pd(dppf)Cl$_2$.CH$_2$Cl$_2$ (15 mg, 0.02 mmol), potassium acetate (56 mg, 0.58 mmol) and 1,4-dioxane (1 ml). The reaction mixture was stirred at 100° C. for 4 h. The reaction mixture was cooled to room temperature and taken on directly into the next step.

Step 2: 3-amino-6-(2-chloro-3-ethyl-1H-pyrrolo[2,3-b]pyridin-5-yl)-N,N-dimethylpicolinamide

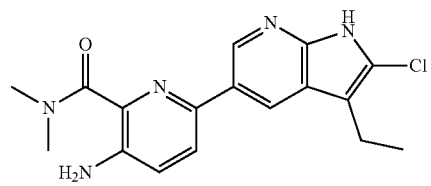 [SMILES: CCc1c(Cl)[nH]c2ncc(-c3ccc(N)c(C(=O)N(C)C)c3)cc12]

To a sealed tube containing the reaction mixture of 2-chloro-3-ethyl-5-(4,4,5,5-tetramethyl-1,3,2-dioxaborolan-2-yl)-1H-pyrrolo[2,3-b]pyridine (50.0 mg, 0.16 mmol) was added 3-amino-6-iodo-N,N-dimethylpicolinamide (58 mg, 0.20 mmol), Pd(dppf)Cl$_2$ (12 mg, 0.02 mmol), Cs$_2$CO$_3$ (128.0 mg, 0.39 mmol), 1,4-dioxane (1 mL) and water (0.5 mL). The mixture was sealed and stirred at 100° C. for 4 h.

The reaction mixture was filtered and the filtrate was concentrated in vacuo. The crude product was purified via flash chromatography on silica gel (dichloromethane/methanol 20:1-10:1) to afford 3-amino-6-(2-chloro-3-ethyl-1H-pyrrolo[2,3-b]pyridin-5-yl)-N,N-dimethylpicolinamide (30.0 mg, 76% yield) as a yellow solid. LCMS (ESI): $R_T$ (min) =1.378, [M+H]$^+$=344.1, method=C; $^1$H NMR (400 MHz, CD$_3$OD) δ 8.72 (d, J=2.0 Hz, 1H), 8.39 (d, J=2.0 Hz, 1H), 7.75 (d, J=8.0 Hz, 1H), 7.32 (d, J=8.0 Hz, 1H), 3.19 (s, 3H), 3.16 (s, 3H), 2.82 (q, J=7.2 Hz, 2H), 1.30 (t, J=7.2 Hz, 3H).

Example 3: Compound 1-3

2-amino-5-(2-chloro-3-ethyl-1H-pyrrolo[2,3-b]pyridin-5-yl)-N,N-dimethylbenzamide

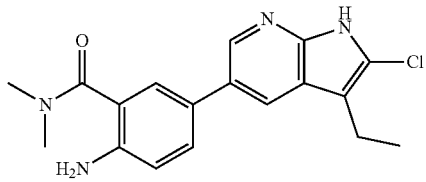

Step 1: 2-amino-5-(2-chloro-3-ethyl-1H-pyrrolo[2,3-b]pyridin-5-yl)-N,N-dimethylbenzamide

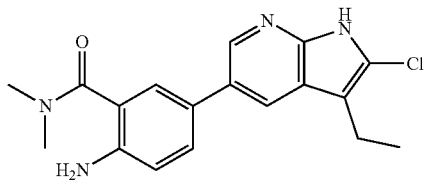 [SMILES: CCc1c(Cl)[nH]c2ncc(-c3ccc(N)c(C(=O)N(C)C)c3)cc12]

A mixture of 5-bromo-2-chloro-3-ethyl-1H-pyrrolo[2,3-b]pyridine (13 mg, 0.05 mmol), 2-amino-N,N-dimethyl-5-(4,4,5,5-tetramethyl-1,3,2-dioxaborolan-2-yl)benzamide (15 mg, 0.05 mmol), 1,1'-bis(diphenylphosphino)ferrocenepalladium(II)dichloride. dichloromethane complex (4 mg, 0.01 mmol), cesium carbonate (49 mg, 0.15 mmol), 1,4-dioxane (1.5 mL) and water (0.5 mL) was stirred at 100° C. for 1.5 h. The reaction was then diluted with water (10 mL), extracted with ethyl acetate (3×10 mL), dried over Na$_2$SO$_4$, filtered and concentrated. The crude product was purified by preparative reverse phase HPLC (C-18, eluting with acetonitrile/water+0.05% HCOOH) to give 2-amino-5-(2-chloro-3-ethyl-1H-pyrrolo[2,3-b]pyridin-5-yl)-N,N-dimethylbenzamide (4 mg, 23%) as an off white solid. LCMS (ESI): $R_T$ (min)=1.43, [M+H]$^+$=343.1, method=A; $^1$H NMR (400 MHz, CD$_3$OD) δ 8.35 (s, 1H), 8.04 (s, 1H), 7.50 (dd, J=2.0, 8.0 Hz, 1H), 7.39 (d, J=2.0 Hz, 1H), 6.93 (d, J=8.4 Hz, 1H), 3.12 (br, 6H), 2.80 (q, J=8.0 Hz, 2H), 1.28 (t, J=7.6 Hz, 3H).

Example 4: Compound 1-4

2-amino-5-(3-ethyl-2-methyl-1H-pyrrolo[2,3-b]pyridin-5-yl)-N,N-dimethylbenzamide

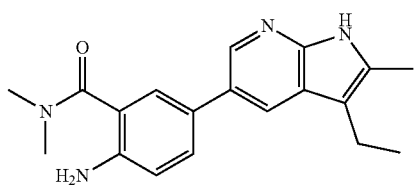

Step 1: 5-bromo-3-(prop-1-ynyl)pyridin-2-amine

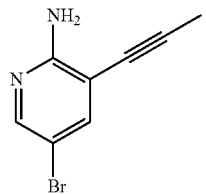

1-Propyne (600 mg, 15 mmol) was condensed into a pre-weighed flask cooled to −40° C. containing tetrahydrofuran (5 mL). The solution was added to a cooled (0-5° C.), degassed mixture of 5-bromo-3-iodo-2-pyridinylamine (1.39 g, 4.65 mmol), bis(triphenylphosphine)palladium(II) chloride (163 mg, 0.23 mmol), copper(I) iodide (53 mg, 0.28 mmol) and triethylamine (1.41 g, 13.93 mmol) in tetrahydrofuran (15 mL). The mixture was stirred at 0-5° C. for 30 min, then for an additional 2.5 h at 20° C. The reaction was then diluted with water (50 mL), extracted with ethyl acetate (3×50 mL), dried over Na$_2$SO$_4$, filtered and concentrated. The crude product was purified by flash chromatography (silica gel, 20 g) eluting with 10% ethyl acetate in petroleum ether to give 5-bromo-3-prop-1-ynyl-pyridin-2-amine (646 mg, 66%). LCMS (ESI) [M+H]$^+$=211.0.

Step 2: 5-bromo-2-methyl-1H-pyrrolo[2,3-b]pyridine

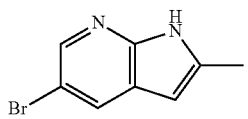

A mixture of 5-bromo-3-prop-1-ynyl-pyridin-2-amine (646 mg, 3.06 mmol), potassium tert-butoxide (558 mg, 4.97 mmol) and 2-methyl-2-propanol (10 mL) was stirred at 85° C. for 20 h. The reaction was diluted with water (30 mL), extracted with ethyl acetate (50 mL×3), dried over Na$_2$SO$_4$, filtered and concentrated to give 5-bromo-2-methyl-1H-pyrrolo[2,3-b]pyridine (584 mg, 90%). LCMS (ESI) [M+H]$^+$=211.0.

Step 3: tert-butyl N-[2-(dimethylcarbamoyl)-4-(2-methyl-1H-pyrrolo[2,3-b]pyridin-5-yl)phenyl]carbamate

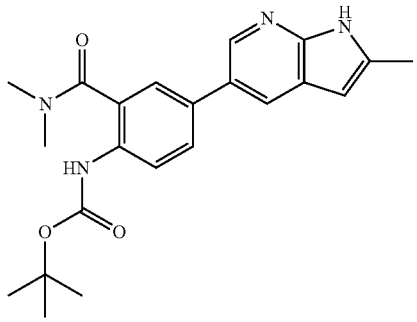

A mixture of 5-bromo-2-methyl-1H-pyrrolo[2,3-b]pyridine (315 mg, 1.49 mmol), tetrakis(triphenylphosphine)palladium(0) (172 mg, 0.15 mmol), potassium carbonate (619 mg, 4.48 mmol), tert-butyl N-[2-(dimethylcarbamoyl)-4-(4,4,5,5-tetramethyl-1,3,2-dioxaborolan-2-yl)phenyl]carbamate (582 mg, 1.49 mmol), 1,4-dioxane (10 mL) and water (2 mL) was stirred at 100° C. for 18 h. The reaction was then diluted with water (30 mL), extracted with ethyl acetate (50 mL×3), dried over $Na_2SO_4$, filtered and concentrated. The reaction was purified by flash chromatography (silica gel, 20 g) eluting with 70-85% ethyl acetate in petroleum ether to give tert-butyl N-[2-(dimethylcarbamoyl)-4-(2-methyl-1H-pyrrolo[2,3-b]pyridin-5-yl)phenyl]carbamate (348 mg, 59%). LCMS (ESI) $[M+H]^+$=395.2.

Step 4: tert-butyl 2-(dimethylcarbamoyl)-4-(3-iodo-2-methyl-1H-pyrrolo[2,3-b]pyridin-5-yl)phenylcarbamate

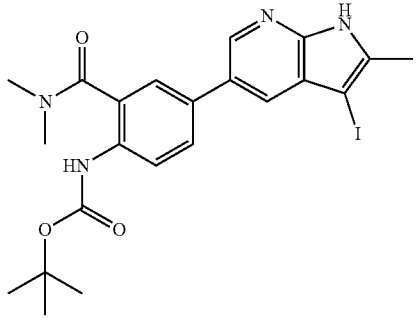

A mixture of tert-butyl N-[2-(dimethylcarbamoyl)-4-(2-methyl-1H-pyrrolo[2,3-b]pyridin-5-yl)phenyl]carbamate (248 mg, 0.48 mmol) and N-iodosuccinimide (130 mg, 0.58 mmol) in acetone (8 mL) was stirred at 20° C. for 1 h. The mixture was then diluted with water (30 mL), extracted with ethyl acetate (30 mL×3), dried over $Na_2SO_4$, filtered and concentrated to give tert-butyl N-[2-(dimethylcarbamoyl)-4-(3-iodo-2-methyl-1H-pyrrolo[2,3-b]pyridin-5-yl)phenyl]carbamate (296 mg, 95%). LCMS (ESI) $[M+H]^+$=521.1.

Step 5: tert-butyl 2-(dimethylcarbamoyl)-4-(2-methyl-3-vinyl-1H-pyrrolo[2,3-b]pyridin-5-yl)phenylcarbamate

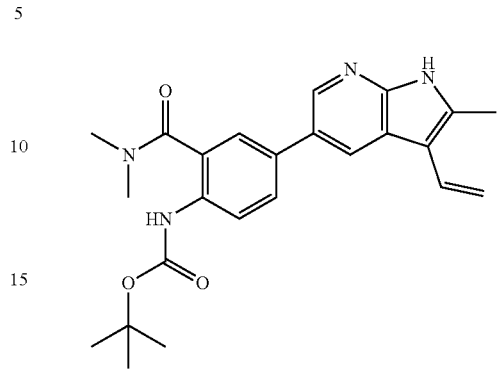

A mixture of tert-butyl N-[2-(dimethylcarbamoyl)-4-(3-iodo-2-methyl-1H-pyrrolo[2,3-b]pyridin-5-yl)phenyl]carbamate (52 mg, 0.10 mmol), potassium carbonate (41 mg, 0.30 mmol), tetrakis(triphenylphosphine)palladium(0) (12 mg, 0.01 mmol), vinylboronic acid pinacol ester (46 mg, 0.30 mmol), 1,4-dioxane (2 mL) and water (0.2 mL) was stirred in sealed tube at 90° C. for 4 h. The reaction was diluted with water (10 mL), extracted with ethyl acetate (3×30 mL), dried over $Na_2SO_4$, filtered and concentrated to give the tert-butyl N-[2-(dimethylcarbamoyl)-4-(2-methyl-3-vinyl-1H-pyrrolo[2,3-b]pyridin-5-yl)phenyl]carbamate (89 mg, 71%). LCMS (ESI) $[M+H]^+$=458.3.

Step 6: tert-butyl 2-(dimethylcarbamoyl)-4-(3-ethyl-2-methyl-1H-pyrrolo[2,3-b]pyridin-5-yl)phenylcarbamate

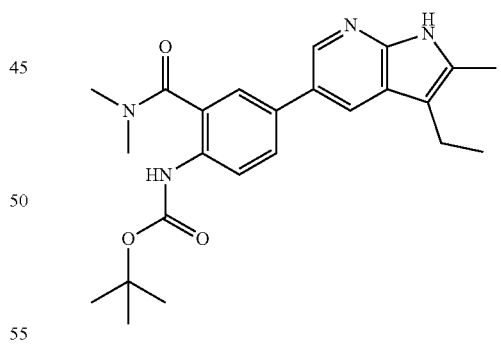

A mixture of tert-butyl N-[2-(dimethylcarbamoyl)-4-(2-methyl-3-vinyl-1H-pyrrolo[2,3-b]pyridin-5-yl)phenyl]carbamate (89 mg, 0.21 mmol) and palladium on activated carbon (10 wt %, 45 mg, 0.21 mmol) in methanol (30 mL) was stirred under $H_2$ at 20° C. for 5 h. The reaction mixture was filtered and concentrated to give tert-butyl N-[2-(dimethylcarbamoyl)-4-(3-ethyl-2-methyl-1H-pyrrolo[2,3-b]pyridin-5-yl)phenyl]carbamate (80 mg, 39%). LCMS (ESI) $[M+H]^+$=423.3.

Step 7: 2-amino-5-(3-ethyl-2-methyl-1H-pyrrolo[2,3-b]pyridin-5-yl)-N,N-dimethylbenzamide

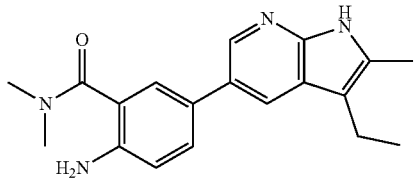

A mixture of tert-butyl N-[2-(dimethylcarbamoyl)-4-(3-ethyl-2-methyl-1H-pyrrolo[2,3-b]pyridin-5-yl)phenyl]carbamate (80 mg, 0.08 mmol) and trifluoroacetic acid (0.5 mL, 6.73 mmol) in dichloromethane (5 mL) was stirred at 20° C. for 18 h. The reaction mixture was diluted with dichloromethane (30 mL), washed with saturated NaHCO$_3$(30 mL), dried over Na$_2$SO$_4$, filtered and concentrated. The crude was purified by flash chromatography (silica gel, 12 g) eluting with 70% ethyl acetate in petroleum ether-dichloromethane:methanol=25:1 to give 2-amino-5-(3-ethyl-2-methyl-1H-pyrrolo[2,3-b]pyridin-5-yl)-N,N-dimethylbenzamide (7.4 mg, 28%). LCMS (ESI): R$_T$=1.21, [M+H]$^+$=323.2, method=A; $^1$H NMR (400 MHz, CDCl$_3$) δ 9.78 (s, 1H), 8.32 (s, 1H), 7.87 (d, J=1.6 Hz, 1H), 7.45 (dd, J=2.0, 8.0 Hz, 1H), 7.37 (d, J=2.0 Hz, 1H), 6.83 (d, J=8.0 Hz, 1H), 3.12 (s, 6H), 2.72 (q, J=7.6 Hz, 2H), 2.45 (s, 3H), 1.24 (t, J=7.6 Hz, 3H).

Example 5: Compound 1-5

4-(6-(2-chloro-3-ethyl-1H-pyrrolo[2,3-b]pyridin-5-yl)pyridin-2-yl)morpholin-3-one

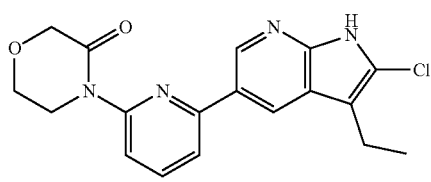 [SMILES: CCc1c(Cl)[nH]c2ncc(-c3cccc(N4CCOCC4=O)n3)cc12]

To a sealed tube containing 2-chloro-3-ethyl-5-(4,4,5,5-tetramethyl-1,3,2-dioxaborolan-2-yl)-1H-pyrrolo[2,3-b]pyridine (80.0 mg, 0.26 mmol) was added 4-(6-bromopyridin-2-yl)morpholin-3-one (80 mg, 0.31 mmol), Pd(dppf)Cl$_2$ (19 mg, 0.03 mmol), K$_2$CO$_3$ (108 mg, 0.78 mmol), 1,4-dioxane (1 ml) and water (1 ml). The mixture was stirred at 100° C. for 2 h. The reaction mixture was filtered and the filtrate was concentrated in vacuo. The crude product was purified via flash chromatography on silica gel (dichloromethane/methanol 20:1-10:1) to afford 4-(6-(2-chloro-3-ethyl-1H-pyrrolo[2,3-b]pyridin-5-yl)pyridin-2-yl)morpholin-3-one (43.0 mg, 43% yield) as a yellow solid. LCMS (ESI): R$_T$ (min)=1.546, [M+H]$^+$=357.1, method=C; $^1$H NMR (400 MHz, CD$_3$OD) δ 8.90 (d, J=2.0 Hz, 1H), 8.56 (d, J=2.0 Hz, 1H), 7.94-7.88 (m, 2H), 7.82 (dd, J=1.6, 6.4 Hz, 1H), 4.36 (s, 2H), 4.23-4.20 (m, 2H), 4.13-4.11 (m, 2H), 2.84 (q, J=7.6 Hz, 2H), 1.31 (t, J=7.6 Hz, 3H).

Example 6: Compound 1-6

(3-amino-6-(2-chloro-3-ethyl-1H-pyrrolo[2,3-b]pyridin-5-yl)pyridin-2-yl)(3-hydroxyazetidin-1-yl)methanone formate

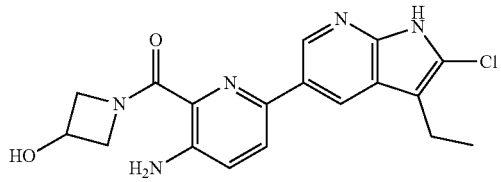 [SMILES: CCc1c(Cl)[nH]c2ncc(-c3ccc(N)c(C(=O)N4CC(O)C4)n3)cc12]

To a sealed tube containing 2-chloro-3-ethyl-5-(4,4,5,5-tetramethyl-1,3,2-dioxaborolan-2-yl)-1H-pyrrolo[2,3-b]pyridine (150.0 mg, 0.49 mmol) was added (3-amino-6-chloropyridin-2-yl)(3-hydroxyazetidin-1-yl)methanone (133 mg, 0.59 mmol), Pd(dppf)Cl$_2$ (35 mg, 0.05 mmol), K$_2$CO$_3$ (202 mg, 1.47 mmol), 1,4-dioxane (1 ml) and water (1 mL). The mixture was stirred at 100° C. for 2 h. The reaction mixture was filtered and the filtrate was concentrated in vacuo. The crude product was purified via C$_{18}$ reverse phase flash chromatography (acetonitrile/water (+0.5% HCOOH) 0-50%) to afford (3-amino-6-(2-chloro-3-ethyl-1H-pyrrolo[2,3-b]pyridin-5-yl)pyridin-2-yl)(3-hydroxyazetidin-1-yl)methanone formate (60.0 mg, 28% yield) as a yellow solid. LCMS (ESI): R$_T$ (min)=1.391, [M+H]$^+$=372.1, method=C; $^1$H NMR (400 MHz, DMSO-d$_6$) δ 12.15 (brs, 1H), 8.79 (s, 1H), 8.46 (s, 1H), 8.39 (s, 1H), 7.89 (d, J=9.2 Hz, 1H), 7.25 (d, J=7.2 Hz, 1H), 6.86 (s, 2H), 5.73 (brs, 1H), 4.91 (q, J=5.2 Hz, 1H), 4.51-4.46 (m, 2H), 4.27 (dd, J=6.0, 10.4 Hz, 1H), 3.79 (dd, J=2.8, 10.4 Hz, 1H), 2.73 (q, J=7.2 Hz, 2H), 1.22 (t, J=7.2 Hz, 3H).

Example 7: Compound 1-7

3-(4-(2-chloro-3-ethyl-1H-pyrrolo[2,3-b]pyridin-5-yl)pyrimidin-2-yl)oxazolidin-2-one formate

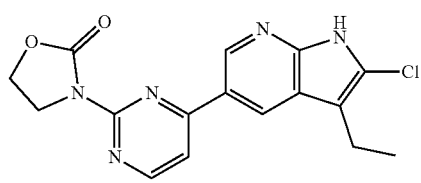 [SMILES: CCc1c(Cl)[nH]c2ncc(-c3ccnc(N4CCOC4=O)n3)cc12]

Step 1: 3-(4-chloropyrimidin-2-yl)oxazolidin-2-one

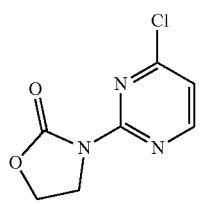 [SMILES: O=C1OCCN1c1nccc(Cl)n1]

To a solution of 2,4-dichloropyrimidine (1.5 g, 10.07 mmol) in tetrahydrofuran (10 ml) was added NaH (440 mg, 11.07 mmol) and oxazolidin-2-one (880 mg, 10.07 mmol). The reaction mixture was stirred at 20° C. for 2 h. The reaction mixture was then concentrated in vacuo. The crude product was purified via flash chromatography on silica gel (0-50% ethyl acetate in petroleum ether) to provide 3-(4-chloropyrimidin-2-yl)oxazolidin-2-one (370 mg, 13% yield) as a white solid. LCMS (ESI) [M+H]$^+$=200.1.

Step 2: 3-(4-(2-chloro-3-ethyl-1H-pyrrolo[2,3-b]pyridin-5-yl)pyrimidin-2-yl)oxazolidin-2-one formate

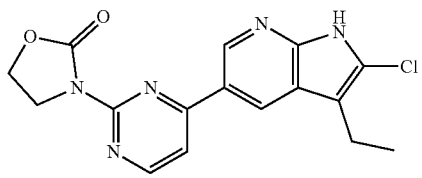 [SMILES: CCc1c(Cl)[nH]c2ncc(-c3ccnc(N4CCOC4=O)n3)cc12]

To a sealed tube containing 2-chloro-3-ethyl-5-(4,4,5,5-tetramethyl-1,3,2-dioxaborolan-2-yl)-1H-pyrrolo[2,3-b]pyridine (50.0 mg, 0.16 mmol) was added 3-(4-chloropyrimidin-2-yl)oxazolidin-2-one (39 mg, 0.20 mmol), Pd(dppf)Cl$_2$ (11 mg, 0.02 mmol), K$_2$CO$_3$ (67 mg, 0.49 mmol), 1,4-dioxane (1 ml) and water (0.5 ml). The mixture was stirred at 90° C. for 2 hr. The reaction mixture was filtered and the filtrate was concentrated in vacuo. The crude product was purified by preparative reverse-phase HPLC to provide 3-(4-(2-chloro-3-ethyl-1H-pyrrolo[2,3-b]pyridin-5-yl)pyrimidin-2-yl)oxazolidin-2-one formate (7.0 mg, 11% yield) as a white solid. LCMS (ESI): R$_T$ (min)=1.424, [M+H]$^+$=344.1, method=C; $^1$H NMR (400 MHz, CD$_3$OD) δ 9.07 (d, J=2.0 Hz, 1H), 8.75 (d, J=2.0 Hz, 1H), 8.69 (d, J=5.2 Hz, 1H), 8.54 (s, 1H), 7.82 (d, J=5.6 Hz, 1H), 4.59-4.55 (m, 2H), 4.46-4.42 (m, 2H), 2.86 (q, J=7.6 Hz, 2H), 1.31 (t, J=7.6 Hz, 3H).

Example 8: Compound 1-8

4-(6-(2-methyl-3-(trifluoromethyl)-1H-pyrrolo[2,3-b]pyridin-5-yl)pyridin-2-yl)morpholin-3-one

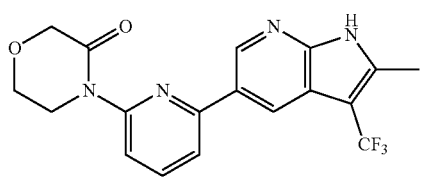 [SMILES: Cc1[nH]c2ncc(-c3cccc(N4CCOCC4=O)n3)cc2c1C(F)(F)F]

A mixture of 2-methyl-5-(4,4,5,5-tetramethyl-1,3,2-dioxaborolan-2-yl)-3-(trifluoromethyl)-1H-pyrrolo[2,3-b]pyridine (18 mg, 0.04 mmol), 4-(6-bromo-2-pyridyl)morpholin-3-one (11 mg, 0.04 mmol), XPhos Pd G2 (4 mg, 0.01 mmol), XPhos (4 mg, 0.01 mmol) and potassium acetate (13 mg, 0.13 mmol) in 1,4-dioxane (2 mL) and water (0.5 mL) in a sealed microwave vessel was stirred under argon at 100° C. for 1.5 h. The reaction mixture was concentrated and was purified directly by silica chromatography (petroleum ether/ethyl acetate=1/1 to 0/1, Rf=0.4 in ethyl acetate 100%) to afford 4-[6-[2-methyl-3-(trifluoromethyl)-1H-pyrrolo[2,3-b]pyridin-5-yl]-2-pyridyl]morpholin-3-one (7 mg, 39% yield) as a white solid. LCMS (ESI): R$_T$ (min)=1.810, [M+H]$^+$=377.1, method=C. $^1$H NMR (400 MHz, DMSO-d$_6$): 12.58 (s, 1H), 9.03 (s, 1H), 8.50 (s, 1H), 7.99-7.92 (m, 3H), 4.30 (s, 2H), 4.12-4.11 (m, 2H), 4.06-4.05 (m, 2H), 2.55 (s, 3H).

Example 9: Compound 1-9

3-amino-N,N-dimethyl-6-(2-methyl-3-(trifluoromethyl)-1H-pyrrolo[2,3-b]pyridin-5-yl)picolinamide

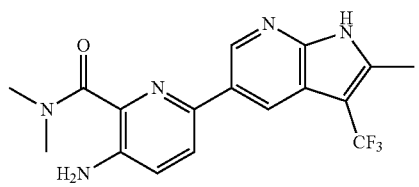

A mixture of 2-methyl-5-(4,4,5,5-tetramethyl-1,3,2-dioxaborolan-2-yl)-3-(trifluoromethyl)-1H-pyrrolo[2,3-b]pyridine (28 mg, 0.09 mmol), 3-amino-6-iodo-N,N-dimethylpyridine-2-carboxamide (25 mg, 0.09 mmol), XPhos Pd G2 (7 mg, 0.01 mmol), XPhos (8 mg, 0.02 mmol) and potassium acetate (26 mg, 0.26 mmol) in 1,4-dioxane (2 mL) and water (0.5 mL) in sealed microwave vessel was stirred under argon at 100° C. for 4 h. The reaction mixture was concentrated and purified directly by silica chromatography (petroleum ether/ethyl acetate=1/1 to 0/1, Rf=0.4 in ethyl acetate 100%) to afford 3-amino-N,N-dimethyl-6-[2-methyl-3-(trifluoromethyl)-1H-pyrrolo[2,3-b]pyridin-5-yl]pyridine-2-carboxamide (3 mg, 9.6% yield) as a yellow solid. LCMS (ESI): R$_T$ (min)=1.697, [M+H]$^+$=364.2, method=C. $^1$H NMR (400 MHz, CD$_3$OD): 8.77 (d, J=2 Hz, 1H), 8.41 (s, 1H), 7.73 (d, J=8.8 Hz, 1H), 7.30 (d, J=8.4 Hz, 1H), 3.18 (s, 3H), 3.15 (s, 3H), 2.59 (d, J=1.2 Hz, 3H).

Example 10: Compound 1-10

2-amino-N,N-dimethyl-5-(2-methyl-3-(trifluoromethyl)-1H-pyrrolo[2,3-b]pyridin-5-yl)benzamide

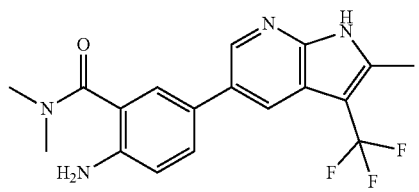

Step 1: tert-butyl 2-(dimethylcarbamoyl)-4-(2-methyl-3-(trifluoromethyl)-1H-pyrrolo[2,3-b]pyridin-5-yl)phenylcarbamate

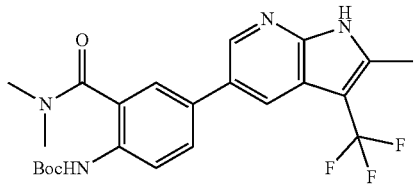

A mixture of 5-bromo-2-methyl-3-(trifluoromethyl)-1H-pyrrolo[2,3-b]pyridine (100 mg, 0.36 mmol), tert-butyl N-[2-(dimethylcarbamoyl)-4-(4,4,5,5-tetramethyl-1,3,2-dioxaborolan-2-yl)phenyl]carbamate (154 mg, 0.39 mmol), XPhos Pd G2 (29 mg, 0.04 mmol), XPhos (34 mg, 0.07 mmol), potassium acetate (108 mg, 1.1 mmol) in 1,4-dioxane (6 mL) and water (1 mL) in a sealed microwave vessel was stirred at 100° C. for 4 h. The reaction mixture was concentrated and directly purified by silica chromatography (petroleum ether/ethyl acetate=1/1 to 1/3, Rf=0.6 in ethyl acetate 100%) to afford tert-butyl N-[2-(dimethylcarbamoyl)-4-[2-methyl-3-(trifluoromethyl)-1H-pyrrolo[2,3-b]pyridin-5-yl]phenyl]carbamate (120 mg, 72.4% yield) as a white solid. LCMS: m/z=463.2 [M+1]

Step 2: 2-amino-N,N-dimethyl-5-(2-methyl-3-(trifluoromethyl)-1H-pyrrolo[2,3-b]pyridin-5-yl)benzamide

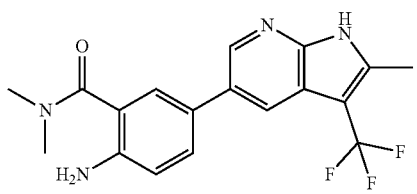

A mixture of tert-butyl N-[2-(dimethylcarbamoyl)-4-[2-methyl-3-(trifluoromethyl)-1H-pyrrolo[2,3-b]pyridin-5-yl]phenyl]carbamate (120 mg, 0.26 mmol) in HCl/dioxane (8.mL, 32 mmol) was stirred at 15° C. for 3 h. The reaction mixture was then concentrated. The residue was washed with Et$_2$O (5 mL×2) to afford 2-amino-N,N-dimethyl-5-[2-methyl-3-(trifluoromethyl)-1H-pyrrolo[2,3-b]pyridin-5-yl]benzamide hydrochloride (87 mg, 0.22 mmol, 84.1% yield) as a yellow solid. LCMS (ESI): R$_T$ (min)=1.725, [M+H]$^+$= 363.1, method=C. $^1$H NMR (400 MHz, CD$_3$OD): δ 8.59 (s, 1H), 8.36 (s, 1H), 7.85 (d, J=8.4 Hz, 1H), 7.82 (s, 1H), 7.48 (d, J=8.4 Hz, 1H), 3.18 (s, 3H), 3.12 (s, 3H), 2.64 (d, J=0.8 Hz, 3H).

Example 11: Compound 1-11

4-(3-amino-6-(2-methyl-3-(trifluoromethyl)-1H-pyrrolo[2,3-b]pyridin-5-yl)pyridin-2-yl)morpholin-3-one

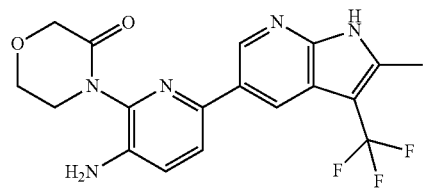 [SMILES: Cc1[nH]c2ncc(-c3ccc(N)c(N4CCOCC4=O)n3)cc2c1C(F)(F)F]

Step 1: 4-(6-methoxy-3-nitropyridin-2-yl)morpholin-3-one

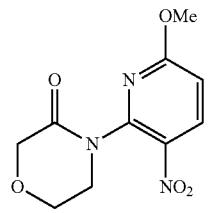 [SMILES: COc1ccc([N+](=O)[O-])c(N2CCOCC2=O)n1]

A mixture of 2-chloro-6-methoxy-3-nitropyridine (1.89 g, 10 mmol), morpholin-3-one (1.01 g, 10 mmol), Xantphos (578 mg, 1.0 mmol), Pd$_2$(dba)$_3$ (457 mg, 0.5 mmol), Cs$_2$CO$_3$ (6.5 g, 20 mmol), in 1,4-dioxane (50 mL) was stirred under nitrogen at 100° C. for 2 h. The mixture was then cooled to room temperature and filtered through Celite. The filtrate was concentrated and purified by flash chromatography (3:1 petroleum ether:ethyl acetate) to afford 4-(6-methoxy-3-nitropyridin-2-yl)morpholin-3-one (1.2 g, yield 47%) as a yellow solid. LCMS (ESI) [M+H]$^+$=254.2.

Step 2: 4-(6-hydroxy-3-nitropyridin-2-yl)morpholin-3-one

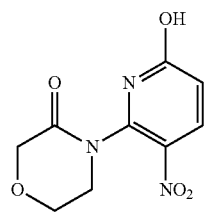 [SMILES: O=C1COCCN1c1nc(O)ccc1[N+](=O)[O-]]

A mixture of 4-(6-methoxy-3-nitro-2-pyridyl)morpholin-3-one (800 mg, 3.1 mmol) and TMSI (1.26 g, 6.32 mmol) in acetonitrile (10 mL) was stirred at 80° C. for 2 h. The mixture was cooled to room temperature and concentrated under reduced pressure. The residue was purified by column chromatography (20:1 dichloromethane: methanol) to afford 4-(6-hydroxy-3-nitropyridin-2-yl)morpholin-3-one (600 mg, 79%) as a brown solid. LCMS (ESI) [M+H]$^+$=240.1

Step 3: 5-nitro-6-(3-oxomorpholino)pyridin-2-yl trifluoromethanesulfonate

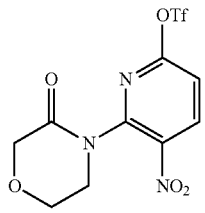 [SMILES: O=C1COCCN1c1nc(OS(=O)(=O)C(F)(F)F)ccc1[N+](=O)[O-]]

To a mixture of 4-(6-hydroxy-3-nitro-2-pyridyl)morpholin-3-one (600 mg, 2.51 mmol) and N,N-diisopropylethylamine (810 mg, 6.27 mmol) in dichloromethane (50 mL) was added trifluoromethanesulfonic anhydride (1.41 g, 5.02 mmol) at −78° C. The mixture was allowed to warm to room temperature and stirred for 2 h. To the mixture was added saturated NaHCO₃ solution (100 mL) and extracted with dichloromethane (3×50 mL). The combined organic extracts were concentrated under reduced pressure. The residue was purified by column chromatography (3:1 petroleum ether: ethyl acetate) to afford 5-nitro-6-(3-oxomorpholino)pyridin-2-yltrifluoromethanesulfonate (800 mg, 86%) as a yellow solid. LCMS (ESI) [M+H]⁺=372.0.

Step 4: 5-amino-6-(3-oxomorpholino)pyridin-2-yl trifluoromethanesulfonate

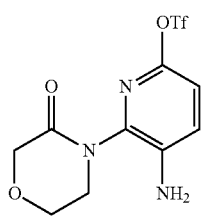 [SMILES: Nc1ccc(OS(=O)(=O)C(F)(F)F)nc1N1CCOCC1=O]

A mixture of [5-nitro-6-(3-oxomorpholin-4-yl)-2-pyridyl]trifluoromethanesulfonate (500 mg, 1.35 mmol) and iron powder (226 mg, 4.04 mmol) in ethanol (20 mL) was stirred at 50° C. for 1 h. The mixture was cooled to room temp and filtered through Celite. The filtrate was concentrated under reduced pressure. The residue was purified by column chromatography (20:1 dichloromethane: methanol) and further purified by reverse phase HPLC (H₂O (0.3% NH₄HCO₃) and CH₃CN) to afford 5-amino-6-(3-oxomorpholino)pyridin-2-yl trifluoromethanesulfonate (60 mg, 13%) as a white solid. LCMS (ESI) [M+H]⁺=342.1.

Step 5: 4-(3-amino-6-(2-methyl-3-(trifluoromethyl)-1H-pyrrolo[2,3-b]pyridin-5-yl)pyridin-2-yl)morpholin-3-one

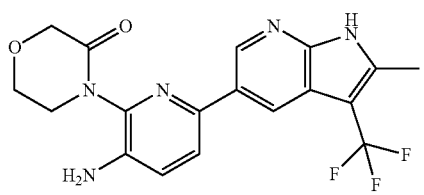 [SMILES: Cc1[nH]c2ncc(-c3ccc(N)c(N4CCOCC4=O)n3)cc2c1C(F)(F)F]

A mixture of 2-methyl-5-(4,4,5,5-tetramethyl-1,3,2-dioxaborolan-2-yl)-3-(trifluoromethyl)-1H-pyrrolo[2,3-b]pyridine (60 mg, 0.18 mmol), [5-amino-6-(3-oxomorpholin-4-yl)-2-pyridyl]trifluoromethanesulfonate (40 mg, 0.12 mmol), XPhos Pd G2 (15 mg, 0.02 mmol), XPhos (20 mg, 0.04 mmol), potassium acetate (60 mg, 0.61 mmol) in 1,4-dioxane (6 mL) and water (1 mL) was stirred under argon in a sealed microwave vessel at 100° C. for 1.5 h. The reaction was concentrated and directly purified by column chromatography (silica gel, petroleum ether/ethyl acetate=3/1 to 1/1 to 100% ethyl acetate, TLC:petroleum ether/ethyl acetate=0/1, Rf=0.1) to afford the crude product which was further purified by reverse phase HPLC (NH₄HCO₃/H₂O/methanol) to afford 4-[3-amino-6-[2-methyl-3-(trifluoromethyl)-1H-pyrrolo[2,3-b]pyridin-5-yl]-2-pyridyl]morpholin-3-one (3 mg, 6.5% yield) as a white solid. LCMS (ESI): R_T (min)=1.464, [M+H]⁺=392.1, method=C; ¹H NMR (400 MHz, DMSO-d₆): δ 8.84 (s, 1H), δ 8.30 (s, 1H), 7.79 (d, J=4.4 Hz, 1H), 7.23 (d, J=4.4 Hz, 1H), 5.37 (s, 2H), 4.25 (s, 2H), 4.05 (t, J=4.0 Hz, 2H), 3.73 (t, J=4.0 Hz, 2H), 2.54 (s, 3H).

Example 12: Compound 1-12

(2-(3-amino-5-(2-methyl-3-(trifluoromethyl)-1H-pyrrolo[2,3-b]pyridin-5-yl)phenyl)pyridin-3-yl)methanol

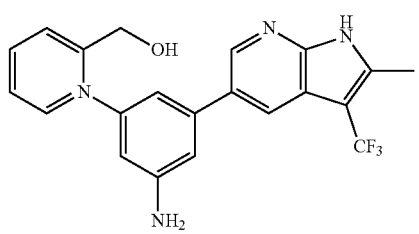

A mixture of [2-[3-amino-5-(4,4,5,5-tetramethyl-1,3,2-dioxaborolan-2-yl)phenyl]-3-pyridyl]methanol (130 mg, 0.4 mmol), 5-bromo-2-methyl-3-(trifluoromethyl)-1H-pyrrolo[2,3-b]pyridine (100 mg, 0.36 mmol), XPhos Pd G2 (30 mg, 0.04 mmol), XPhos (35 mg, 0.07 mmol), potassium acetate (120 mg, 1.22 mmol) in 1,4-dioxane (6 mL) and water (1 mL) was stirred under argon in sealed microwave vessel at 100° C. for 3 h. The reaction mixture was concentrated and purified by silica flash chromatography (petroleum ether/ethyl acetate=1/1 to 0/1, Rf=0.2 at ethyl acetate 100%) to afford [2-[3-amino-5-[2-methyl-3-(trifluoromethyl)-1H-pyrrolo[2,3-b]pyridin-5-yl]phenyl]-3-pyridyl]methanol (66.6 mg, 47% yield) as a yellow solid. LCMS (ESI): R_T (min)= 1.257, [M+H]⁺=399.1, method=C. ¹H NMR (400 MHz, CD₃OD): δ 8.50-8.49 (m, 2H), 8.16 (s, 1H), 8.01 (d, J=7.6 Hz, 1H), 7.48-7.45 (m, 1H), 7.09-7.08 (m, 1H), 7.05 (s, 1H), 6.84 (t, J=1.6 Hz, 1H), 4.66 (s, 2H), 2.59 (d, J=1.2 Hz, 3H).

Example 13: Compound 1-13

4-(3-(2-(hydroxymethyl)-3-(trifluoromethyl)-1H-pyrrolo[2,3-b]pyridin-5-yl)phenyl)morpholin-3-one

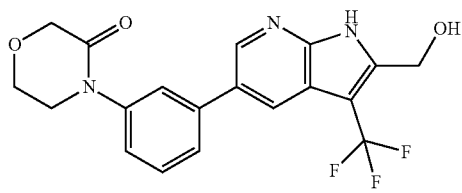 [SMILES: O=C1COCCN1c1cccc(-c2cnc3[nH]c(CO)c(C(F)(F)F)c3c2)c1]

Step 1: 5-bromo-1-(p-tolylsulfonyl)pyrrolo[2,3-b]pyridine

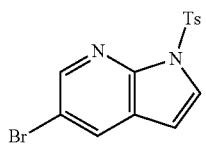 [SMILES: Cc1ccc(S(=O)(=O)n2ccc3cc(Br)cnc32)cc1]

To a solution of 5-bromo-1H-pyrrolo[2,3-b]pyridine (2.0 g, 10.15 mmol) in tetrahydrofuran (50 mL) was added NaH (0.61 g, 15.2 mmol), the mixture was stirred at 25° C. for 0.5 h. p-Tolunesulfonyl chloride (2.32 g, 12.2 mmol) was added to the mixture and stirred for an additional 2 h. The mixture was diluted with saturated NaHCO$_3$(300 mL) and extracted with ethyl acetate (250 mL×3), dried over Na$_2$SO$_4$, filtered, concentrated and purified by column chromatography eluting with ethyl acetate/hexane=1:8 to afford 5-bromo-1-(p-tolylsulfonyl)pyrrolo[2,3-b]pyridine (3.3 g, 9.40 mmol, 93% yield) as a white solid. LCMS (ESI) [M+H]$^+$=351.0

Step 2: [5-bromo-1-(p-tolylsulfonyl)pyrrolo[2,3-b]pyridin-2-yl]methanol

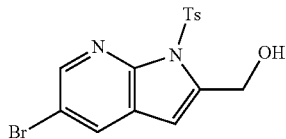 [SMILES: Cc1ccc(S(=O)(=O)n2c(CO)cc3cc(Br)cnc32)cc1]

To a solution of 5-bromo-1-(p-tolylsulfonyl)pyrrolo[2,3-b]pyridine (3.0 g, 8.5 mmol) in tetrahydrofuran (60 mL) at −78° C. was added lithium diisopropylamide (2.5 M in tetrahydrofuran, 6.4 mL, 12.81 mmol). The mixture was stirred at −78° C. for 1 h. Paraformaldehyde (0.77 g, 25.6 mmol) was added and the reaction was allowed to warm to room temperature and stirred for 2 h. The reaction mixture was quenched by adding saturated aqueous NaHCO$_3$(50 mL) and extracted with ethyl acetate (3×250 mL). The combined organic extracts were washed with brine (100 mL), dried with Na$_2$SO$_4$, filtered and evaporated under reduced pressure. The residue was purified by column chromatography eluting with ethyl acetate/hexane=1:2 to afford [5-bromo-1-(p-tolylsulfonyl)pyrrolo[2,3-b]pyridin-2-yl]methanol (1.3 g, 39% yield) as a white solid. LCMS (ESI) [M+H]$^+$=381.0.

Step 3: [5-bromo-3-iodo-1-(p-tolylsulfonyl)pyrrolo[2,3-b]pyridin-2-yl]methanol

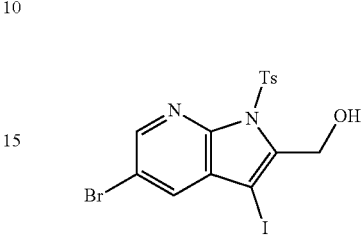

To a solution of [5-bromo-1-(p-tolylsulfonyl)pyrrolo[2,3-b]pyridin-2-yl]methanol (1.1 g, 2.89 mmol) and potassium acetate (14.14 g, 144.3 mmol) in acetic acid (50 mL) was added N-iodosuccinimide (0.71 g, 3.2 mmol). The mixture was stirred at 25° C. for 3 h. The reaction mixture was neutralized with saturated NaHCO$_3$(aq.) to pH 7-8. The mixture was extracted with ethyl acetate (3×150 mL). The combined organic layers were washed with brine (100 ml), dried over Na$_2$SO$_4$, concentrated and purified by column chromatography eluting with ethyl acetate/hexane=1:3 to afford [5-bromo-3-iodo-1-(p-tolylsulfonyl)pyrrolo[2,3-b]pyridin-2-yl]methanol (240 mg, 0.40 mmol, 14% yield) as a white solid. LCMS (ESI) [M+H]$^+$=506.9.

Step 4: [5-bromo-1-(p-tolylsulfonyl)-3-(trifluoromethyl)pyrrolo[2,3-b]pyridin-2-yl]methanol

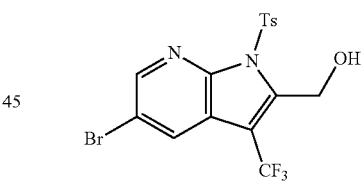

To a solution of diphenyl(trifluoromethyl)sulfonium trifluoromethanesulfonate (382 mg, 0.95 mmol) and [5-bromo-3-iodo-1-(p-tolylsulfonyl)pyrrolo[2,3-b]pyridin-2-yl]methanol (240 mg, 0.47 mmol) in N,N-dimethylformamide (8 mL) was added copper powder (91 mg, 1.42 mmol) at room temperature. The resulting mixture was heated to 60° C. and stirred overnight. Ethyl acetate (200 mL) was added to the mixture and the layers were separated. The organic layer was washed with brine (3×30 mL), dried with Na$_2$SO$_4$, filtered and evaporated under reduced pressure. The residue was purified by column chromatography eluting with ethyl acetate/hexane=1:8 to afford [5-bromo-1-(p-tolylsulfonyl)-3-(trifluoromethyl)pyrrolo[2,3-b]pyridin-2-yl]methanol (106 mg, 50% yield) as a white solid. LCMS (ESI) [M+H]$^+$=449.0.

Step 5: 4-[3-[2-(hydroxymethyl)-1-(p-tolylsulfonyl)-3-(trifluoromethyl)pyrrolo[2,3-b]pyridin-5-yl]phenyl]morpholin-3-one

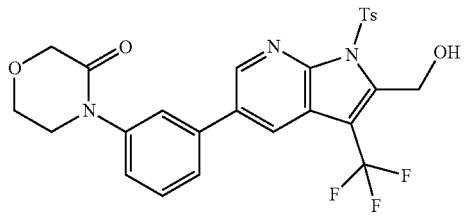 [SMILES: Cc1ccc(S(=O)(=O)n2c(CO)c(C(F)(F)F)c3cc(-c4cccc(N5CCOCC5=O)c4)cnc32)cc1]

A mixture of [5-bromo-1-(p-tolylsulfonyl)-3-(trifluoromethyl)pyrrolo[2,3-b]pyridin-2-yl]methanol (50 mg, 0.11 mmol), 4-[3-(4,4,5,5-tetramethyl-1,3,2-dioxaborolan-2-yl)phenyl]morpholin-3-one (67 mg, 0.22 mmol), Pd(dppf)Cl$_2$ (8 mg, 0.01 mmol) and potassium acetate (22 mg, 0.22 mmol) in 1,4-dioxane (3 mL) and water (0.3 mL) was stirred overnight under argon at 80° C. The reaction was then diluted with ethyl acetate (150 mL). The mixture was washed with H$_2$O (20 mL), brine (20 mL), dried with Na$_2$SO$_4$, filtered and concentrated under reduced pressure. The residue was purified by preparative TLC eluting with ethyl acetate/hexane=3:1 to afford 4-[3-[2-(hydroxymethyl)-1-(p-tolylsulfonyl)-3-(trifluoromethyl)pyrrolo[2,3-b]pyridin-5-yl]phenyl]morpholin-3-one (64 mg, 80% yield) as a white solid. LCMS (ESI) [M+H]$^+$=546.1.

Step 6: 4-[3-[2-(hydroxymethyl)-3-(trifluoromethyl)-1H-pyrrolo[2,3-b]pyridin-5-yl]phenyl]morpholin-3-one

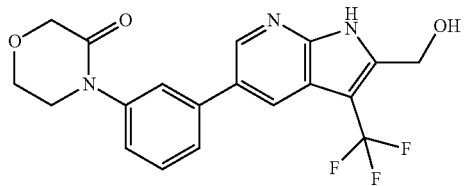 [SMILES: O=C1COCCN1c1cccc(-c2cnc3[nH]c(CO)c(C(F)(F)F)c3c2)c1]

A mixture of 4-[3-[2-(hydroxymethyl)-1-(p-tolylsulfonyl)-3-(trifluoromethyl)pyrrolo[2,3-b]pyridin-5-yl]phenyl]morpholin-3-one (64 mg, 0.09 mmol) and tetrabutylammonium fluoride (70 mg, 0.27 mmol) in tetrahydrofuran (5 mL) was stirred at 25° C. for 2 h. The reaction was then diluted with water (20 mL). The mixture was extracted with ethyl acetate (3×50 mL). The combined extracts were washed with brine (20 mL), dried with Na$_2$SO$_4$, filtered and concentrated under reduced pressure. The residue was purified by preparative reverse phase (C-18) HPLC, eluting with acetonitrile/water+0.05% HCOOH, to give 4-[3-[2-(hydroxymethyl)-3-(trifluoromethyl)-1H-pyrrolo[2,3-b]pyridin-5-yl]phenyl]morpholin-3-one (14 mg, 40% yield) as a white solid. LCMS (ESI): R$_T$(min)=1.693, [M+H]$^+$=392.1, method=C; $^1$H NMR (400 MHz, DMSO-d$_6$) δ 12.74 (s, 1H), 8.64 (d, J=2.0 Hz, 1H), 8.14 (s, 1H), 7.78 (s, 1H), 7.66 (d, J=8.0 Hz, 1H), 7.54 (t, J=7.8 Hz, 1H), 7.41 (d, J=8.0 Hz, 1H), 5.82 (s, 1H), 4.78 (s, 2H), 4.24 (s, 2H), 4.01 (t, J=5.0 Hz, 2H), 3.84 (t, J=4.8 Hz, 2H).

Example 14: Compound 1-14

4-(3-(2-chloro-3-(2-fluoroethyl)-1H-pyrrolo[2,3-b]pyridin-5-yl)phenyl) morpholin-3-one

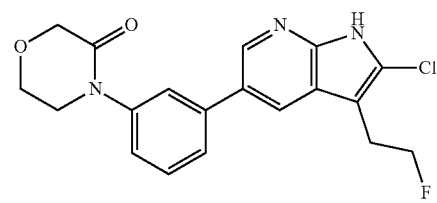 [SMILES: O=C1COCCN1c1cccc(-c2cnc3[nH]c(Cl)c(CCF)c3c2)c1]

Step 1: 5-bromo-3-(2-fluoroethyl)-1-(p-tolylsulfonyl)pyrrolo[2,3-b]pyridine

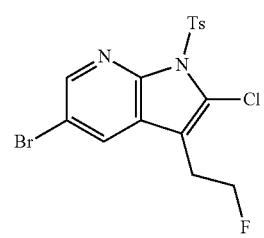 [SMILES: Cc1ccc(S(=O)(=O)n2c(Cl)c(CCF)c3cc(Br)cnc32)cc1]

To a cooled (0° C.) solution of 2-[5-bromo-1-(p-tolylsulfonyl)pyrrolo[2,3-b]pyridin-3-yl]ethanol (2.1 g, 5.31 mmol) in dichloromethane (100 mL) was added DAST (1.28 g, 7.97 mmol). The mixture was stirred at room temperature for 2 h. The reaction mixture was neutralized with sat NaHCO$_3$(aq.) to pH 7-8. The mixture was extracted with dichloromethane (3×150 mL). The combined organic layers were washed with brine (100 ml), dried over Na$_2$SO$_4$, concentrated and purified by column chromatography eluting with ethyl acetate/hexane=1:9 to afford 5-bromo-3-(2-fluoroethyl)-1-(p-tolylsulfonyl)pyrrolo[2,3-b]pyridine (660 mg, 1.66 mmol, 31% yield) as a white solid. LCMS (ESI) [M+H]$^+$=399.0.

Step 2: 5-bromo-2-chloro-3-(2-fluoroethyl)-1-(p-tolylsulfonyl)pyrrolo[2,3-b]pyridine To a solution of 5-bromo-3-(2-fluoroethyl)-1-(p-tolylsulfonyl)pyrrolo[2,3-b]pyridine (100 mg, 0.25 mmol) in tetrahydrofuran (2.5 mL) at −78° C. was added LDA (2.5 M in tetrahydrofuran, 0.2 mL, 0.38 mmol) and the resulting mixture was stirred at −78° C. for 1 h. Benzenesulfonyl chloride (0.05 mL, 0.38 mmol) in tetrahydrofuran (1 mL)

was then added and the reaction mixture was stirred at room temperature for 3 h. The reaction mixture was then quenched with a saturated solution of NaHCO₃ to pH 7-8. The mixture was extracted with dichloromethane (3×100 mL). The combined organic layers were washed with brine (100 ml), dried over Na₂SO₄ and concentrated to give crude 5-bromo-2-chloro-3-(2-fluoroethyl)-1-(p-tolylsulfonyl)pyrrolo[2,3-b]pyridine (103 mg, 0.16 mmol, 63% yield) as a white solid. LCMS (ESI) [M+H]⁺=430.9.

Step 3: 4-[3-[2-chloro-3-(2-fluoroethyl)-1-(p-tolylsulfonyl)pyrrolo[2,3-b]pyridin-5-yl]phenyl]morpholin-3-one

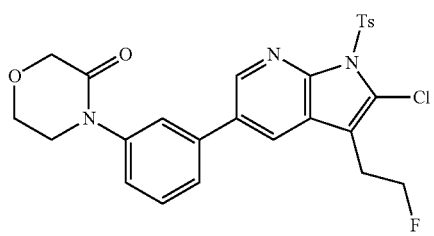 [SMILES: Cc1ccc(S(=O)(=O)n2c(Cl)c(CCF)c3cc(-c4cccc(N5CCOCC5=O)c4)cnc32)cc1]

A mixture of 5-bromo-2-chloro-3-(2-fluoroethyl)-1-(p-tolylsulfonyl)pyrrolo[2,3-b]pyridine (90 mg, 0.21 mmol), 4-[3-(4,4,5,5-tetramethyl-1,3,2-dioxaborolan-2-yl)phenyl]morpholin-3-one (126 mg, 0.42 mmol), Pd(dppf)Cl₂ (15 mg, 0.02 mmol) and potassium acetate (41 mg, 0.42 mmol) in 1,4-dioxane (5 mL) and water (0.5 mL) was stirred overnight under argon at 80° C. The mixture was concentrated and purified by preparative reverse phase (C-18) HPLC, eluting with acetonitrile/water+0.05% NH₄HCO₃, to give 4-[3-[2-chloro-3-(2-fluoroethyl)-1-(p-tolylsulfonyl)pyrrolo[2,3-b]pyridin-5-yl]phenyl]morpholin-3-one (93 mg, 56% yield) as a white solid. LCMS (ESI) [M+H]⁺=528.0.

Step 4: 4-[3-[2-chloro-3-(2-fluoroethyl)-1H-pyrrolo[2,3-b]pyridin-5-yl]phenyl]morpholin-3-one

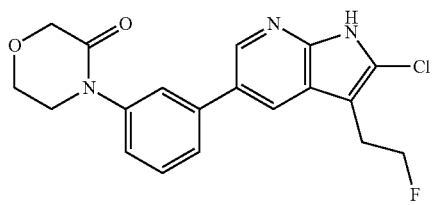 [SMILES: O=C1COCCN1c1cccc(-c2cnc3[nH]c(Cl)c(CCF)c3c2)c1]

A mixture of 4-[3-[2-chloro-3-(2-fluoroethyl)-1-(p-tolylsulfonyl)pyrrolo[2,3-b]pyridin-5-yl]phenyl]morpholin-3-one (93 mg, 0.12 mmol) and tetrabutylammonium fluoride (91 mg, 0.35 mmol) in tetrahydrofuran (5 mL) was stirred at 25° C. for 2 h. The reaction was then diluted with water (20 mL) and extracted with ethyl acetate (3×20 mL). The combined extracts were washed with brine (20 mL), dried with Na₂SO₄, filtered and concentrated under reduced pressure. The residue was purified by preparative reverse phase (C-18) HPLC, eluting with acetonitrile/water+0.05% NH₄HCO₃, to give 4-[3-[2-chloro-3-(2-fluoroethyl)-1H-pyrrolo[2,3-b]pyridin-5-yl]phenyl]morpholin-3-one (16 mg, 37% yield) as a white solid. LCMS (ESI): R$_T$ (min)=1.762, [M+H]⁺=374.1, method=C; ¹H NMR (400 MHz, DMSO-d₆) δ 12.51 (s, 1H), 8.54 (d, J=2.0 Hz, 1H), 8.27 (d, J=2.0 Hz, 1H), 7.76 (s, 1H), 7.66 (d, J=8.0 Hz, 1H), 7.52 (t, J=8.0 Hz, 1H), 7.39 (d, J=8.0 Hz, 1H), 4.71 (t, J=6.4 Hz, 1H), 4.60 (t, J=6.6 Hz, 1H), 4.24 (s, 2H), 4.01 (t, J=5.0 Hz, 2H), 3.83 (t, J=5.0 Hz, 2H), 3.17 (t, J=6.4 Hz, 1H), 3.11 (t, J=6.4 Hz, 1H).

Example 15: Compound 1-15

(4-(6-(2-methyl-3-(trifluoromethyl)-1H-pyrrolo[2,3-b]pyridin-5-yl)pyridin-2-yl)morpholin-3-yl)methanol

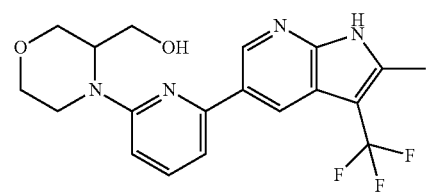 [SMILES: Cc1[nH]c2ncc(-c3cccc(N4CCOCC4CO)n3)cc2c1C(F)(F)F]

Step 1: 3-((tert-butyldiphenylsilyloxy)methyl)morpholine

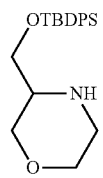

To a solution of morpholin-3-ylmethanol (0.9 g, 7.68 mmol), diisopropylethylamine (1.86 g, 15.37 mmol) in dichloromethane (25 mL) was added tert-butylchlorodiphenylsilane (2.4 mL, 9.22 mmol) dropwise at 20° C. The solution was stirred at 20° C. for 2 h. The mixture was concentrated and the residue was purified by silica gel flash chromatography (0-100% ethyl acetate in petroleum ether) to give the desired product 3-((tert-butyldiphenylsilyloxy)methyl)morpholine (0.7 g, 1.97 mmol, 26% yield) as a colorless oil. LCMS (ESI): [M+H]⁺=356.7

Step 2: (4-(6-bromopyridin-2-yl)morpholin-3-yl)methanol

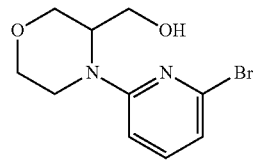 [SMILES: OCC1COCCN1c1cccc(Br)n1]

A mixture of 2-bromo-6-fluoropyridine (343 mg, 1.95 mmol), 3-((tert-butyldiphenylsilyloxy)methyl)morpholine (660 mg, 1.86 mmol), and Cs₂CO₃ (1.2 g, 3.71 mmol) in acetonitrile (20 mL) was stirred at 100° C. for 16 h. The mixture was filtered and the residue was purified by silica gel flash chromatography (0-10% methanol in dichlo- Step 3: (4-(6-(2-methyl-3-(trifluoromethyl)-1H-pyrrolo[2,3-b]pyridin-5-yl)pyridin-2-yl)morpholin-3-yl)methanol

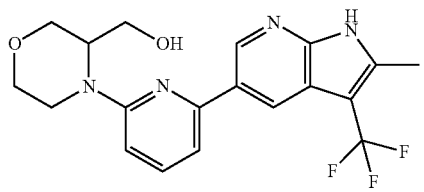

A mixture of 2-methyl-5-(4,4,5,5-tetramethyl-1,3,2-dioxaborolan-2-yl)-3-(trifluoromethyl)-1H-pyrrolo[2,3-b]pyridine (119 mg, 0.37 mmol), [4-(6-bromo-2-pyridyl)morpholin-3-yl]methanol (100 mg, 0.37 mmol), potassium acetate (72 mg, 0.73 mmol), Xphos (34 mg, 0.07 mmol), Xphos-Pd-G2 (28 mg, 0.04 mmol), water (1 mL), and 1,4-dioxane (10 mL) was stirred under $N_2$ at 100° C. for 4 h. The mixture was filtered, concentrated and the resulting residue was purified by reverse phase chromatography (acetonitrile:0.1% HCOOH in water 0-60%) to afford [4-[6-[2-methyl-3-(trifluoromethyl)-1H-pyrrolo [2,3-b]pyridin-5-yl]-2-pyridyl]morpholin-3-yl]methanol (18 mg, 12% yield) as a white solid. LCMS (ESI): $R_T$ (min)=1.30, [M+H]$^+$=393.7 method=C, $^1$H NMR (400 MHz, CD$_3$OD): δ 8.94 (d, J=1.6 Hz, 1H), 8.57 (d, J=1.6 Hz, 1H), 7.83 (dd, J=7.6, 8.4 Hz, 1H), 7.60 (d, J=7.6 Hz, 1H), 6.88 (d, J=8.4 Hz, 1H), 4.67-4.52 (m, 2H), 4.16-3.98 (m, 2H), 3.77-3.70 (m, 3H), 3.25-3.21 (m, 2H), 2.62 (s, 3H).

Example 16: Compound 1-16

1-(6-(2-methyl-3-(trifluoromethyl)-1H-pyrrolo[2,3-b]pyridin-5-yl)pyridin-2-yl)tetrahydropyrimidin-2(1H)-one

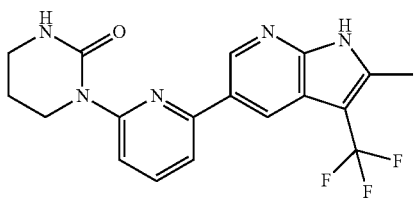 [SMILES: Cc1[nH]c2ncc(-c3cccc(N4CCCNC4=O)n3)cc2c1C(F)(F)F]

Step 1: 1-(6-bromopyridin-2-yl)tetrahydropyrimidin-2(1H)-one

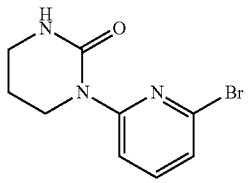 [SMILES: O=C1NCCCN1c1cccc(Br)n1]

Tetrahydro-2(1H)-pyrimidinone (1.7 g, 16.9 mmol), Pd$_2$(dba)$_3$ (386 mg, 0.42 mmol), Xantphos (367 mg, 0.63 mmol) and Cs$_2$CO$_3$ (1.93 g, 5.9 mmol) were added sequentially to a solution 2,6-dibromopyridine (1.0 g, 4.2 mmol) in 1,4-dioxane (300 mL). The reaction mixture was stirred at 100° C. for 2 h and then was filtered. The filtrate was partitioned between H$_2$O (35 mL) and CH$_2$Cl$_2$ (2×50 mL). The combined organic layers were dried over Na$_2$SO$_4$ and were concentrated. The residue was purified by silica gel flash chromatography (petroleum ether: ethyl acetate=9:1) to afford 1-(6-bromopyridin-2-yl)tetrahydropyrimidin-2(1H)-one (643 mg, 2.28 mmol, 54% yield) as a yellow solid. LCMS (ESI) [M+H]$^+$=256.1.

Step 2: 1-(6-(2-methyl-3-(trifluoromethyl)-1H-pyrrolo[2,3-b]pyridin-5-yl)pyridin-2-yl)tetrahydropyrimidin-2(1H)-one

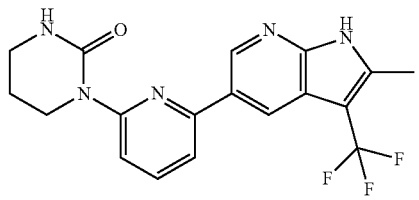 [SMILES: Cc1[nH]c2ncc(-c3cccc(N4CCCNC4=O)n3)cc2c1C(F)(F)F]

Potassium acetate (27 mg, 0.28 mmol), 2-methyl-5-(4,4,5,5-tetramethyl-1,3,2-dioxaborolan-2-yl)-3-(trifluoromethyl)-1H-pyrrolo[2,3-b]pyridine (51 mg, 0.11 mmol) and Pd(dppf)Cl$_2$ (10 mg, 0.01 mmol) were added sequentially to a solution 1-(6-bromo-2-pyridyl)hexahydropyrimidin-2-one (40 mg, 0.14 mmol) in 1,4-dioxane (3 mL) and water (0.2 mL) at room temperature. The reaction mixture was stirred at 110° C. for 2 h and then was filtered. The filtrate was partitioned between H$_2$O (10 mL) and CH$_2$Cl$_2$ (2×10 mL), and the combined organic layers were dried over Na$_2$SO$_4$ and were concentrated. The residue was purified by reverse phase HPLC (A: water (0.05% formic acid) B: acetonitrile) to afford 1-(6-(2-methyl-3-(trifluoromethyl)-1H-pyrrolo[2,3-b]pyridin-5-yl)pyridin-2-yl)tetrahydropyrimidin-2(1H)-one (6 mg, 10% yield) as a white solid. LCMS (ESI) $R_T$ (min)=1.552 [M+H]$^+$=376.1, method=C; $^1$H NMR (400 MHz, DMSO-d$_6$) δ 12.53 (s, 1H), 9.01 (d, J=1.9 Hz, 1H), 8.49 (s, 1H), 7.85 (d, J=7.8 Hz, 1H), 7.82-7.66 (m, 2H), 6.97 (s, 1H), 4.11-3.97 (m, 2H), 3.25 (d, J=3.7 Hz, 2H), 2.56 (s, 3H), 2.16-1.82 (m, 2H).

Example 17: Compound 1-17

2-amino-N,N-dimethyl-5-(2-methyl-1H-pyrrolo[2,3-b]pyridin-5-yl)benzamide

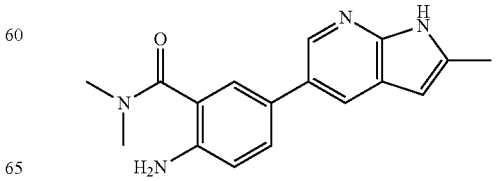

The title compound was prepared using a procedure that is analogous to that described for example 10.

Example 18: Compound 1-18

4-[3-(3-Ethyl-2-fluoro-1H-pyrrolo[2,3-b]pyridin-5-yl)phenyl]morpholin-3-one

Step 1: 5-Bromo-3-ethyl-1-(toluene-4-sulfonyl)-1H-pyrrolo[2,3-b]pyridine

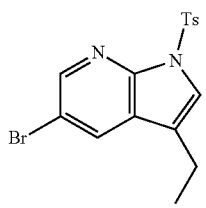 [SMILES: CCc1cn(S(=O)(=O)c2ccc(C)cc2)c2ncc(Br)cc12]

NaH (60% dispersion, 205 mg, 5.1 mmol), was added to a stirred solution of 5-bromo-3-ethyl-1H-pyrrolo[2,3-b]pyridine (0.95 g, 4.2 mmol) and p-toluenesulfonyl chloride (880 mg, 4.6 mmol) in dry tetrahydrofuran (20 mL) at 0° C. under $N_2$. After 1 hour at 0° C., the reaction mixture was treated with saturated aq. $NaHCO_3$ and partitioned between ethyl acetate/$H_2O$. The aqueous layer was extracted with ethyl acetate (×2). The combined extracts were washed with water (×1), brine (×1), dried ($Na_2SO_4$), filtered and evaporated. The residue was treated with $Et_2O$ and the solid was collected by filtration to give 5-bromo-3-ethyl-1-(toluene-4-sulfonyl)-1H-pyrrolo[2,3-b]pyridine (1.27 g, 80% yield) as an off-white solid. $^1$H NMR (400 MHz, DMSO-$d_6$) δ 8.45 (d, J=2.0 Hz, 1H), 8.34 (d, J=2.3 Hz, 1H), 7.97-7.92 (m, 2H), 7.70 (s, 1H), 7.43-7.39 (m, 2H), 2.66 (qd, J=7.4, 1.1 Hz, 2H), 2.34 (s, 3H), 1.23 (t, J=7.4 Hz, 3H). LCMS (Method D): $R_T$ 4.31 min (ESI) [M+H]$^+$=378.9/380.9.

Step 2: 5-Bromo-3-ethyl-2-fluoro-1-(toluene-4-sulfonyl)-1H-pyrrolo[2,3-b]pyridine

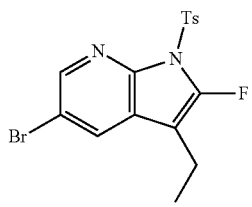 [SMILES: CCc1c(F)n(S(=O)(=O)c2ccc(C)cc2)c2ncc(Br)cc12]

A solution of lithium diisopropylamide (2.0 M in tetrahydrofuran/heptane/ethylbenzene, 1.1 mL, 2.2 mmol) was added dropwise to a stirred solution of 5-bromo-3-ethyl-1-(toluene-4-sulfonyl)-1H-pyrrolo[2,3-b]pyridine (700 mg, 1.9 mmol) in dry tetrahydrofuran (10 mL) at −78° C. under nitrogen. After 2 hours at −78° C., a solution of N-fluorobenzenesulfonimide (875 mg, 2.8 mmol) in dry tetrahydrofuran (3 mL) was added slowly. After 15 minutes, the cooling bath was removed and the reaction mixture was allowed to warm to room temperature and stirred at this temperature for 1 hour. The reaction was treated with saturated $NaHCO_3$ and partitioned between ethyl acetate/$H_2O$. The aqueous layer was extracted with ethyl acetate (×2). The combined organic extracts were washed with water, brine, dried ($Na_2SO_4$), filtered and evaporated. The residue was purified by chromatography on silica (20-100% dichloromethane/cyclohexane) to give an off-white foam (624 mg). LCMS and NMR data were consistent with a mixture of 5-bromo-3-ethyl-2-fluoro-1-(toluene-4-sulfonyl)-1H-pyrrolo[2,3-b]pyridine and 5-bromo-3-ethyl-1-(toluene-4-sulfonyl)-1H-pyrrolo[2,3-b]pyridine (~3:1 ratio). LCMS (Method D) $R_T$: 4.24 min (ESI) [M+H]$^+$=397/399 (title compound); 379/381 (starting material).

Step 3: 4-{3-[3-Ethyl-2-fluoro-1-(toluene-4-sulfonyl)-1H-pyrrolo[2,3-b]pyridin-5-yl]phenyl}morpholin-3-one

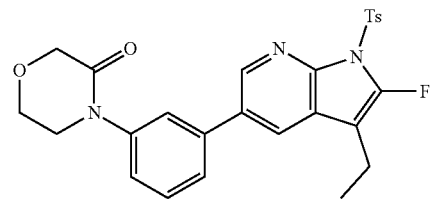 [SMILES: CCc1c(F)n(S(=O)(=O)c2ccc(C)cc2)c2ncc(-c3cccc(N4CCOCC4=O)c3)cc12]

5-Bromo-3-ethyl-2-fluoro-1-(toluene-4-sulfonyl)-1H-pyrrolo[2,3-b]pyridine (~3:1 mixture with C2-H compound, 200 mg, ~0.5 mmol), 4-[3-(4,4,5,5-tetramethyl-[1,3,2]dioxaborolan-2-yl)phenyl]morpholin-3-one (230 mg, 0.75 mmol), chloro(2-dicyclohexylphosphino-2',4',6'-triisopropyl-1,1'-biphenyl)[2-(2'-amino-1,1'-biphenyl)]palladium(II) (XPhos-Pd-G2, 39 mg, 0.05 mmol), 2-dicyclohexylphosphino-2',4',6'-triisopropylbiphenyl (XPhos, 2 mg, 0.05 mmol) and potassium acetate (98 mg, 1.0 mmol) were combined in a microwave vial. 1,4-Dioxane (3 mL) and water (0.6 mL) were added. The vial was sealed and the mixture was degased by purging with $N_2$. The reaction mixture was stirred and heated at 100° C. in the microwave for 1 hour. After cooling, the reaction mixture was treated with saturated $NaHCO_3$ and partitioned between ethyl acetate/$H_2O$. The aqueous layer was extracted with ethyl acetate (×2). The combined extracts were washed with water, brine, dried ($Na_2SO_4$), filtered and concentrated. The residue was purified by chromatography on silica (10-80% ethyl acetate/dichloromethane) to give a pale yellow solid (320 mg). LCMS (Method D) $R_T$: 3.65 min; (ESI) [M+H]$^+$= 494. LCMS also indicated presence of C2-H compound (ESI) [M+H—F]$^+$=476 as an inseparable mixture. This material was used in the following step without further purification.

Step 4: 4-[3-(3-Ethyl-2-fluoro-1H-pyrrolo[2,3-b]pyridin-5-yl)-phenyl]morpholin-3-one

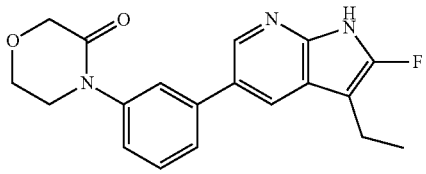 [SMILES: CCc1c(F)[nH]c2ncc(-c3cccc(N4CCOCC4=O)c3)cc12]

A solution of tetrabutylammonium fluoride (1.0M in tetrahydrofuran, 0.6 mL, 0.6 mmol) was added to a stirred solution of 4-{3-[3-ethyl-2-fluoro-1-(toluene-4-sulfonyl)-1H-pyrrolo[2,3-b]pyridin-5-yl]phenyl}morpholin-3-one (Step 3, 320 mg) in tetrahydrofuran (2 mL) at $R_T$. After 16 hours at $R_T$ the reaction mixture was treated with saturated NaHCO$_3$ and partitioned between ethyl acetate/H$_2$O. The aqueous layer was extracted with ethyl acetate (×2). The combined extracts were washed with water, brine, dried (Na$_2$SO$_4$), filtered and concentrated. The residue was taken up in methanol and loaded on to SCX-2 (5 g). The cartridge was eluted with methanol (30 mL) and the product was eluted with 2M NH$_3$-methanol (30 mL). The ammonia-methanol fraction was evaporated and the residue was further purified by chromatography on silica (20-100% ethyl acetate/dichloromethane) to give a pale yellow solid (82 mg, 0.2 mmol). $^1$H NMR (400 MHz, DMSO-d$_6$) δ 12.3 (br.s, 1H), 8.46 (d, J=2.1 Hz, 1H), 8.16 (d, J=2.2 Hz, 1H), 7.75 (t, J=1.8 Hz, 1H), 7.66-7.62 (m, 1H), 7.51 (t, J=7.9 Hz, 1H), 7.38 (ddd, J=7.9, 2.0, 1.0 Hz, 1H), 4.23 (s, 2H), 4.03-3.99 (m, 2H), 3.86-3.81 (m, 2H), 2.67 (q, J=7.4 Hz, 2H), 1.2 (t, J=7.4 Hz, 3H); LCMS (Method E: $R_T$ 3.82 min (ESI) [M+H]$^+$=340.2.

Example 19: Compound 1-19

6-Amino-3-(3-ethyl-2-fluoro-1H-pyrrolo[2,3-b]pyridin-5-yl)-2-fluoro-N,N-dimethylbenzamide

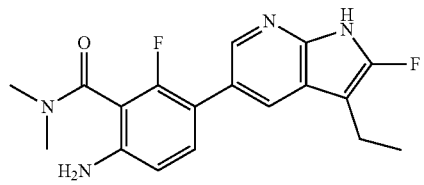 [SMILES: CCc1c(F)[nH]c2ncc(-c3ccc(N)c(C(=O)N(C)C)c3F)cc12]

Step 1: 6-Amino-3-[3-ethyl-2-fluoro-1-(toluene-4-sulfonyl)-1H-pyrrolo[2,3-b]pyridin-5-yl]-2-fluoro-N,N-dimethylbenzamide

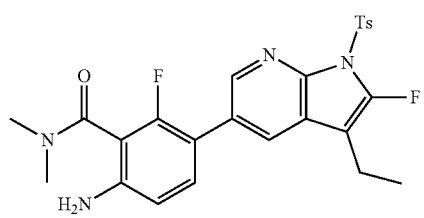 [SMILES: CCc1c(F)n(S(=O)(=O)c2ccc(C)cc2)c2ncc(-c3ccc(N)c(C(=O)N(C)C)c3F)cc12]

5-Bromo-3-ethyl-2-fluoro-1-(toluene-4-sulfonyl)-1H-pyrrolo[2,3-b]pyridine (~3:1 mixture with C2-H compound, 200 mg, ~0.5 mmol), 6-amino-2-fluoro-N,N-dimethyl-3-(4,4,5,5-tetramethyl-[1,3,2]dioxaborolan-2-yl)benzamide (230 mg, 0.75 mmol), chloro(2-dicyclohexylphosphino-2',4',6'-triisopropyl-1,1'-biphenyl)[2-(2'-amino-1,1'-biphenyl)]palladium(II) (XPhos-Pd-G2, 39 mg, 0.05 mmol), 2-dicyclohexylphosphino-2',4',6'-triisopropylbiphenyl (XPhos, 2 mg, 0.05 mmol) and potassium acetate (98 mg, 1.0 mmol) were combined in a microwave vial. 1,4-Dioxane (3 mL) and water (0.6 mL) were added. The vial was sealed and the mixture was degassed by purging with N$_2$. The reaction mixture was stirred and heated at 100° C. in the microwave for 1 hour. After cooling, the reaction mixture was treated with saturated NaHCO$_3$ and then partitioned between ethyl acetate/H$_2$O. The aqueous layer was extracted with ethyl acetate (×2). The combined extracts were washed with water, brine, dried (Na$_2$SO$_4$), filtered and concentrated. The residue was purified by chromatography on silica (10-100% ethyl acetate/dichloromethane) to give a yellow oil (376 mg). LCMS (Method D): $R_T$ 3.59 min; (ESI) [M+H]$^+$=499. LCMS also indicated presence of C2-H compound (ESI) [M+H—F]$^+$=481 as an inseparable mixture. This material was used in the following step without further purification.

Step 2: 6-Amino-3-(3-ethyl-2-fluoro-1H-pyrrolo[2,3-b]pyridin-5-yl)-2-fluoro-N,N-dimethylbenzamide

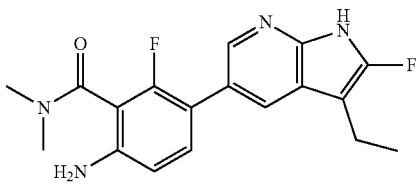 [SMILES: CCc1c(F)[nH]c2ncc(-c3ccc(N)c(C(=O)N(C)C)c3F)cc12]

A solution of tetrabutylammonium fluoride (1.0M in tetrahydrofuran, 0.6 mL, 0.6 mmol) was added to a stirred solution of 6-amino-3-[3-ethyl-2-fluoro-1-(toluene-4-sulfonyl)-1H-pyrrolo[2,3-b]pyridin-5-yl]-2-fluoro-N,N-dimethylbenzamide (Step 1, 376 mg crude, ~0.5 mmol) in tetrahydrofuran (2 mL) at room temperature. After 16 hours at room temperature the reaction mixture was treated with saturated NaHCO$_3$ and then partitioned between ethyl acetate/H$_2$O. The aqueous layer was extracted with ethyl acetate (×2). The combined extracts were washed with water, brine, dried (Na$_2$SO$_4$), filtered and concentrated. The residue was taken up in methanol and loaded onto SCX-2 (5 g). The SCX-2 cartridge was eluted with methanol (30 mL) and the product was eluted with 2M NH$_3$ in methanol (30 mL). The ammonia-methanol fraction was evaporated and the residue was further purified by chromatography on silica (20-100% ethyl acetate/dichloromethane, then 0-7% methanol/ethyl acetate) to give a cream solid (84 mg, 48%). $^1$H NMR (400 MHz, DMSO-d$_6$) δ 12.2 (br.s, 1H), 8.20 (t, J=1.9 Hz, 1H), 7.89 (t, J=1.8 Hz, 1H), 7.28 (t, J=8.8 Hz, 1H), 6.63 (d, J=8.5 Hz, 1H), 5.40 (br.s, 2H), 3.01 (s, 3H), 2.91 (s, 3H), 2.64 (q, J=7.7 Hz, 2H), 1.22 (t, J=7.6 Hz, 3H); LCMS (Method E: $R_T$ 3.65 min; (ESI) [M+H]$^+$=345.1.

Example 20: Compound 1-20

6-Amino-3-[2-chloro-3-(2-hydroxyethyl)-1-(toluene-4-sulfonyl)-1H-pyrrolo[2,3-b]pyridin-5-yl]-2-fluoro-N,N-dimethylbenzamide

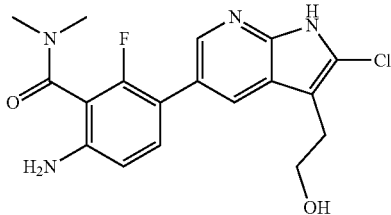 [SMILES: CN(C)C(=O)c1c(N)ccc(-c2cnc3[nH]c(Cl)c(CCO)c3c2)c1F]

Step 1: 6-Amino-3-[2-chloro-3-(2-hydroxyethyl)-1-(toluene-4-sulfonyl)-1H-pyrrolo[2,3-b]pyridin-5-yl]-2-fluoro-N,N-dimethylbenzamide

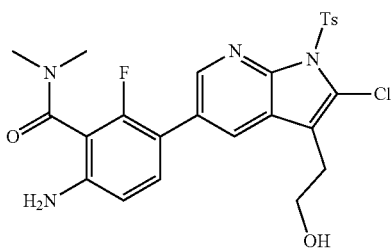 [SMILES: Cc1ccc(S(=O)(=O)n2c(Cl)c(CCO)c3cc(-c4ccc(N)c(C(=O)N(C)C)c4F)cnc32)cc1]

A mixture of 2-[5-bromo-2-chloro-1-(toluene-4-sulfonyl)-1H-pyrrolo[2,3-b]pyridin-3-yl]ethanol Intermediate 22 (103 mg, 0.240 mmol), 6-amino-2-fluoro-N,N-dimethyl-3-(4,4,5,5-tetramethyl-[1,3,2]dioxaborolan-2-yl)benzamide (111 mg, 0.360 mmol), Pd(dppf)Cl$_2$.dichloromethane (10 mol %, 20 mg) and potassium acetate (47 mg, 0.480 mmol) in dioxane/water (1.5 mL/0.3 mL) was degassed (argon) and stirred in a sealed tube at 80° C. for 2 h. The cooled mixture was diluted with water and washed with ethyl acetate (×3). The organic extracts were combined, dried (Na$_2$SO$_4$) and evaporated to give a brown solid. Purification by column chromatography (0-10% methanol/dichloromethane) gave the title compound (70 mg, 55% yield) as a brown oil. LCMS (ESI) [M+H]$^+$=531.

Step 2: 6-Amino-3-[2-chloro-3-(2-hydroxyethyl)-1H-pyrrolo[2,3-b]pyridin-5-yl]-2-fluoro-N,N-dimethylbenzamide

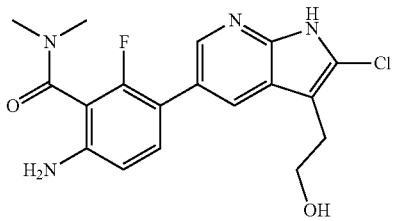 [SMILES: CN(C)C(=O)c1c(N)ccc(-c2cnc3[nH]c(Cl)c(CCO)c3c2)c1F]

A mixture of tetrabutylammonium fluoride (1M in tetrahydrofuran, 0.16 mL, 0.158 mmol) and 6-amino-3-[2-chloro-3-(2-hydroxyethyl)-1-(toluene-4-sulfonyl)-1H-pyrrolo[2,3-b]pyridin-5-yl]-2-fluoro-N,N-dimethylbenzamide (70 mg, 0.132 mmol) was stirred in anhydrous tetrahydrofuran (1.0 mL) at R$_T$ for 20 h. The mixture was diluted with water and washed with ethyl acetate (×3). The organic extracts were combined, dried (Na$_2$SO$_4$) and evaporated to give a brown solid. Purification by column chromatography (0-10% methanol/dichloromethane) gave a yellow residue, which was taken up in methanol, loaded onto a SCX-2 cartridge, washed with methanol and the product eluted with 2M NH$_3$ in methanol. Concentration of product fractions gave the title compound (17.7 mg, 36% yield) as a yellow solid. LCMS (ESI): R$_T$ (min)=2.72, [M+H]$^+$=377.1, method=D; $^1$H NMR (400 MHz, DMSO-d$_6$) δ 12.27 (br s, 1H), 8.25 (m, 1H), 7.95 (m, 1H), 7.28 (m, 1H), 6.63 (d, J=8.6 Hz, 1H), 5.42 (br s, 2H), 4.70 (t, J=5.3 Hz, 1H), 3.59 (m, 2H), 3.01 (s, 3H), 2.90 (s, 3H), 2.83 (m, 2H)

Example 21: Compound 1-21

4-{3-[2-Chloro-3-(2-hydroxyethyl)-1H-pyrrolo[2,3-b]pyridin-5-yl]phenyl}morpholin-3-one

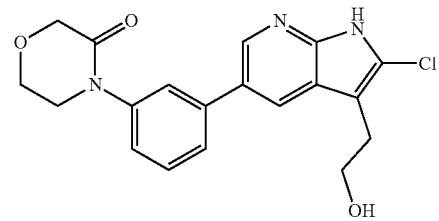 [SMILES: O=C1COCCN1c1cccc(-c2cnc3[nH]c(Cl)c(CCO)c3c2)c1]

Step 1: 4-{3-[2-Chloro-3-(2-hydroxyethyl)-1-(toluene-4-sulfonyl)-1H-pyrrolo[2,3-b]pyridin-5-yl]phenyl}morpholin-3-one

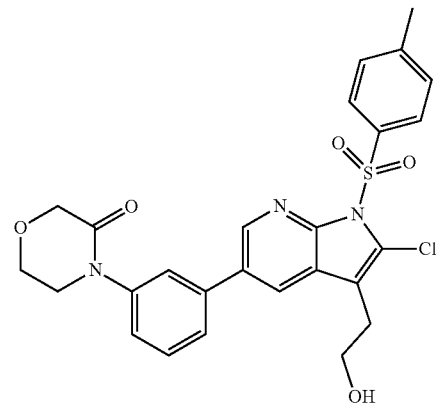 [SMILES: Cc1ccc(S(=O)(=O)n2c(Cl)c(CCO)c3cc(-c4cccc(N5CCOCC5=O)c4)cnc32)cc1]

A mixture of 2-[5-bromo-2-chloro-1-(toluene-4-sulfonyl)-1H-pyrrolo[2,3-b]pyridin-3-yl]ethanol (103 mg, 0.240 mmol), 4-[3-(4,4,5,5-tetramethyl-[1,3,2]dioxaborolan-2-yl)phenyl]morpholin-3-one (109 mg, 0.360 mmol), Pd(dppf)Cl$_2$.DCM (10 mol %, 20 mg) and potassium acetate (47 mg, 0.480 mmol) in dioxane/water (1.5 mL/0.3 mL) was degassed (argon) and stirred in a sealed tube at 80° C. for 2 h. The cooled mixture was diluted with water and extracted with ethyl acetate (×3). The organic extracts were combined, dried (Na₂SO₄) and evaporated to give a brown solid. Purification by column chromatography (0-10% methanol/dichloromethane) gave the title compound (123 mg, 97% yield) as an orange/brown oil. LCMS (ESI) [M+H]⁺=526.

Step 2: 4-{3-[2-Chloro-3-(2-hydroxyethyl)-1H-pyrrolo[2,3-b]pyridin-5-yl]phenyl}morpholin-3-one

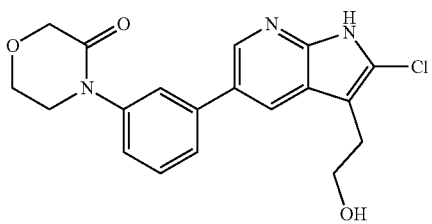 [SMILES: O=C1COCCN1c1cccc(-c2cnc3[nH]c(Cl)c(CCO)c3c2)c1]

A mixture of tetrabutylammonium fluoride (1M in tetrahydrofuran, 0.28 mL, 0.28 mmol) and 4-{3-[2-chloro-3-(2-hydroxyethyl)-1-(toluene-4-sulfonyl)-1H-pyrrolo[2,3-b]pyridin-5-yl]-phenyl}morpholin-3-one (123 mg, 0.234 mmol) was stirred in anhydrous tetrahydrofuran (1.0 mL) at R$_T$ for 18 h. The mixture was diluted with methanol, loaded onto a SCX-2 cartridge, washed with methanol and the product eluted with 2 M NH₃ in methanol. Evaporation of this gave an orange oil, which was purified by column chromatography (0-10% methanol/dichloromethane) to give a yellow residue. Further purification by column chromatography (0-20% methanol/ethyl acetate) gave the title compound (25 mg, 29%) as an off white solid. LCMS (ESI): RT (min)=2.86, [M+H]⁺=372.1, method=C; ¹H NMR (400 MHz, DMSO-d₆) δ 12.33 (br s, 1H), 8.51 (d, J=2.2 Hz, 1H), 8.20 (d, J=2.2 Hz, 1H), 7.75 (m, 1H), 7.64 (dm, J=7.7 Hz, 1H), 7.52 (m, 1H), 7.38 (dm, J=7.8 Hz, 1H), 4.70 (t, J=5.4 Hz, 1H), 4.23 (br s, 2H), 4.00 (m, 2H), 3.83 (m, 2H), 3.63 (m, 2H), 2.88 (m, 2H)

II. Evaluation of Compounds

1. Chemical

Exemplary compounds of Formulae I and Ia were prepared and characterized. The structures, names, LC/MS and ¹H NMR data are provided in Table A1.

TABLE A1

| Compound | Structure/Name | LCMS R$_T$ (min), M + H⁺, method | ¹H NMR (ppm) |
| --- | --- | --- | --- |
| 1-1 | 4-(3-(2-chloro-3-ethyl-1H-pyrrolo[2,3-b]pyridin-5-yl)phenyl)morpholin-3-one | 1.463, 356.1, C | ¹H NMR (400 MHz, CD₃OD) δ 8.44 (s, 1H), 8.10 (s, 1H), 7.70 (s, 1H), 7.65 (d, J = 7.2 Hz, 1H), 7.58 (t, J = 7.2 Hz, 1H), 7.38 (d, J = 7.2 Hz, 1H), 4.34 (s, 2H), 4.11-4.08 (m, 2H), 3.89-3.87 (m, 2H), 2.82 (q, J = 6.0 Hz, 2H), 1.29 (t, J = 6.0 Hz, 3H) |
| 1-2 | 3-amino-6-(2-chloro-3-ethyl-1H-pyrrolo[2,3-b]pyridin-5-yl)-N,N-dimethylpicolinamide | 1.378, 344.1, C | ¹H NMR (400 MHz, CD₃OD) δ 8.72 (d, J = 2.0 Hz, 1H), 8.39 (d, J = 2.0 Hz, 1H), 7.75 (d, J = 8.0 Hz, 1H), 7.32 (d, J = 8.0 Hz, 1H), 3.19 (s, 3H), 3.16 (s, 3H), 2.82 (q, J = 7.2 Hz, 2H), 1.30 (t, J = 7.2 Hz, 3H). |
| 1-3 | 2-amino-5-(2-chloro-3-ethyl-1H-pyrrolo[2,3-b]pyridin-5-yl)-N,N-dimethylbenzamide | 1.43, 343.1, A | ¹H NMR (400 MHz, CD₃OD) δ 8.35 (s, 1H), 8.04 (s, 1H), 7.50 (dd, J = 2.0, 8.0 Hz, 1H), 7.39 (d, J = 2.0 Hz, 1H), 6.93 (d, J = 8.4 Hz, 1H), 3.12 (br, 6H), 2.80 (q, J = 8.0 Hz, 2H), 1.28 (t, J = 7.6 Hz, 3H). |

TABLE A1-continued

| Compound | Structure/Name | LCMS R_T (min), M + H+, method | $^1$H NMR (ppm) |
|---|---|---|---|
| 1-4 | 2-amino-5-(3-ethyl-2-methyl-1H-pyrrolo[2,3-b]pyridin-5-yl)-N,N-dimethylbenzamide | 1.21, 323.2, A | $^1$H NMR (400 MHz, CDCl$_3$) δ 9.78 (s, 1H), 8.32 (s, 1H), 7.87 (d, J = 1.6 Hz, 1H), 7.45 (dd, J = 2.0, 8.0 Hz, 1H), 7.37 (d, J = 2.0 Hz, 1H), 6.83 (d, J = 8.0 Hz, 1H), 3.12 (s, 6H), 2.72 (q, J = 7.6 Hz, 2H), 2.45 (s, 3H), 1.24 (t, J = 7.6 Hz, 3H). |
| 1-5 | 4-(6-(2-chloro-3-ethyl-1H-pyrrolo[2,3-b]pyridin-5-yl)pyridin-2-yl)morpholin-3-one | 1.546, 357.1, C | $^1$H NMR (400 MHz, CD$_3$OD) δ 8.90 (d, J = 2.0 Hz, 1H), 8.56 (d, J = 2.0 Hz, 1H), 7.94-7.88 (m, 2H), 7.82 (dd, J = 1.6, 6.4 Hz, 1H), 4.36 (s, 2H), 4.23-4.20 (m, 2H), 4.13-4.11 (m, 2H), 2.84 (q, J = 7.6 Hz, 2H), 1.31 (t, J = 7.6 Hz, 3H). |
| 1-6 | (3-amino-6-(2-chloro-3-ethyl-1H-pyrrolo[2,3-b]pyridin-5-yl)pyridin-2-yl)(3-hydroxyazetidin-1-yl)methanone | 1.391, 372.1, C | $^1$H NMR (400 MHz, DMSO-d$_6$) δ 12.15 (brs, 1H), 8.79 (s, 1H), 8.46 (s, 1H), 8.39 (s, 1H), 7.89 (d, J = 9.2 Hz, 1H), 7.25 (d, J = 7.2 Hz, 1H), 6.86 (s, 2H), 5.73 (brs, 1H), 4.91 (q, J = 5.2 Hz, 1H), 4.51-4.46 (m, 2H), 4.27 (dd, J = 6.0, 10.4 Hz, 1H), 3.79 (dd, J = 2.8, 10.4 Hz, 1H), 2.73 (q, J = 7.2 Hz, 2H), 1.22 (t, J = 7.2 Hz, 3H). |
| 1-7 | 3-(4-(2-chloro-3-ethyl-1H-pyrrolo[2,3-b]pyridin-5-yl)pyrimidin-2-yl)oxazolidin-2-one | 1.424, 344.1, C | $^1$H NMR (400 MHz, CD$_3$OD) δ 9.07 (d, J = 2.0 Hz, 1H), 8.75 (d, J = 2.0 Hz, 1H), 8.69 (d, J = 5.2 Hz, 1H), 8.54 (s, 1H), 7.82 (d, J = 5.6 Hz, 1H), 4.59-4.55 (m, 2H), 4.46-4.42 (m, 2H), 2.86 (q, J = 7.6 Hz, 2H), 1.31 (t, J = 7.6 Hz, 3H). |
| 1-8 | 4-(6-(2-methyl-3-(trifluoromethyl)-1H-pyrrolo[2,3-b]pyridin-5-yl)pyridin-2-yl)morpholin-3-one | 1.810, 377.1, C | $^1$H NMR (400 MHz, DMSO-d$_6$) δ 12.58 (s, 1H), 9.03 (s, 1H), 8.50 (s, 1H), 7.99-7.92 (m, 3H), 4.30 (s, 2H), 4.12-4.11 (m, 2H), 4.06-4.05 (m, 2H), 2.55 (s, 3H). |

TABLE A1-continued

| Compound | Structure/Name | LCMS R$_T$ (min), M + H$^+$, method | $^1$H NMR (ppm) |
|---|---|---|---|
| 1-9 | 3-amino-N,N-dimethyl-6-(2-methyl-3-(trifluoromethyl)-1H-pyrrolo[2,3-b]pyridin-5-yl)picolinamide | 1.697, 364.2, C | $^1$H NMR (400 MHz, CD$_3$OD): δ 8.77 (d, J = 2 Hz, 1H), 8.41 (s, 1H), 7.73 (d, J = 8.8 Hz, 1H), 7.30 (d, J = 8.4 Hz, 1H), 3.18 (s, 3H), 3.15 (s, 3H), 2.59 (d, J = 1.2 Hz, 3H). |
| 1-10 | 2-amino-N,N-dimethyl-5-(2-methyl-3-(trifluoromethyl)-1H-pyrrolo[2,3-b]pyridin-5-yl)benzamide | 1.725, 363.1, C | $^1$H NMR (400MHz, CD$_3$OD): δ 8.59 (s, 1H), 8.36 (s, 1H), 7.85 (d, J = 8.4 Hz, 1H), 7.82 (s, 1H), 7.48 (d, J = 8.4 Hz, 1H), 3.18 (s, 3H), 3.12 (s, 3H), 2.64 (d, J = 0.8 Hz, 3H). |
| 1-11 | 4-(3-amino-6-(2-methyl-3-(trifluromethyl)-1H-pyrrolo[2,3-b]pyridin-5-yl)pyridin-2-yl)morpholin-3-one | 1.464, 392.1, C | $^1$H NMR (400 MHz, DMSO-d$_6$): δ 8.84 (s, 1H), δ 8.30 (s, 1H), 7.79 (d, J = 4.4 Hz, 1H), 7.23 (d, J = 4.4 Hz, 1H), 5.37 (s, 2H), 4.25 (s, 2H), 4.05 (t, J = 4.0 Hz, 2H), 3.73 (t, J = 4.0 Hz, 2H), 2.54 (s, 3H). |
| 1-12 | (2-(3-amino-5-(2-methyl-3-(trifluoromethyl)-1H-pyrrlol[2,3-b]pyridin-5-yl)phenyl)pyridin-3-yl)methanol | 1.257, 399.1, C | $^1$H NMR (400 MHz, CD$_3$OD): δ 8.50-8.49 (m, 2H), 8.16 (s, 1H), 8.01 (d, J = 7.6 Hz, 1H), 7.48-7.45 (m, 1H), 7.09-7.08 (m, 1H), 7.05 (s, 1H), 6.84 (t, J = 1.6 Hz, 1H), 4.66 (s, 2H), 2.59 (d, J = 1.2 Hz, 3H). |
| 1-13 | 4-(3-(2-(hydroxymethyl)-3-(trifluoromethyl)-1H-pyrrolo[2,3-b]pyridin-5-yl)phenyl)morpholin-3-one | 1.693, 392.1, C | $^1$H NMR (400 MHz, DMSO-d$_6$) δ 12.74 (s, 1H), 8.64 (d, J = 2.0 Hz, 1H), 8.14 (s, 1H), 7.78 (s, 1H), 7.66 (d, J = 8.0 Hz, 1H), 7.54 (t, J = 7.8 Hz, 1H), 7.41 (d, J = 8.0 Hz, 1H), 5.82 (s, 1H), 4.78 (s, 2H), 4.24 (s, 2H), 4.01 (t, J = 5.0 Hz, 2H), 3.84 (t, J = 4.8 Hz, 2H). |

TABLE A1-continued

| Compound | Structure/Name | LCMS R_T (min), M + H+, method | ¹H NMR (ppm) |
|---|---|---|---|
| 1-14 | 4-(3-(2-chloro-3-(2-fluoroethyl)-1H-pyrrolo[2,3-b]pyridin-5-yl)phenyl)morpholin-3-one | 1.762, 374.1, C | ¹H NMR (400 MHz, DMSO-d₆) δ 12.51 (s, 1H), 8.54 (d, J = 2.0 Hz, 1H), 8.27 (d, J = 2.0 Hz, 1H), 7.76 (s, 1H), 7.66 (d, J = 8.0 Hz, 1H), 7.52 (t, J = 8.0 Hz, 1H), 7.39 (d, J = 8.0 Hz, 1H), 4.71 (t, J = 6.4 Hz, 1H), 4.60 (t, J = 6.6 Hz, 1H), 4.24 (s, 2H), 4.01 (t, J = 5.0 Hz, 2H), 3.83 (t, J = 5.0 Hz, 2H), 3.17 (t, J = 6.4 Hz, 1H), 3.11 (t, J = 6.4 Hz, 1H). |
| 1-15 | (4-(6-(2-methyl-3-(trifluoromethyl)-1H-pyrrolo[2,3-b]pyridin-5-yl)pyridin-2-yl)morpholin-3-yl)methanol | 1.30, 393.7, C | ¹H NMR (400 MHz, CD₃OD): δ 8.94 (d, J = 1.6 Hz, 1H), 8.57 (d, J = 1.6 Hz, 1H), 7.83 (dd, J = 7.6, 8.4 Hz, 1H), 7.60 (d, J = 7.6 Hz, 1H), 6.88 (d, J = 8.4 Hz, 1H), 4.67-4.52 (m, 2H), 4.16-3.98 (m, 2H), 3.77-3.70 (m, 3H), 3.25-3.21 (m, 2H), 2.62 (s, 3H). |
| 1-16 | 1-(6-(2-methyl-3-(trifluoromethyl)-1H-pyrrolo[2,3-b]pyridin-5-yl)pyridin-2-yl)tetrahydropyrimidin-2(1H)-one | 1.552, 376.1, C | ¹H NMR (400 MHz, DMSO-d₆) δ 12.53 (s, 1H), 9.01 (d, J = 1.9 Hz, 1H), 8.49 (s, 1H), 7.85 (d, J = 7.8 Hz, 1H), 7.82-7.66 (m, 2H), 6.97 (s, 1H), 4.11-3.97 (m, 2H), 3.25 (d, J = 3.7 Hz, 2H), 2.56 (s, 3H), 2.16-1.82 (m, 2H). |
| 1-17 | 2-amino-N,N-dimethyl-5-(2-methyl-1H-pyrrolo[2,3-b]pyridin-5-yl)benzamide | 1.08, 295.1, C | ¹H NMR (400 MHz, , CD₃OD) δ 8.24 (s, 1H), 7.95 (d, 1H), 7.46 (m, 1H), 7.36 (d, 1H), 6.91 (d, 1H), 6.20 (s, 1H), 3.11 (s, 6H), 2.47 (s, 3H) |
| 1-18 | 4-[3-(3-Ethyl-2-fluoro-1H-pyrrolo[2,3-b]pyridin-5-yl)phenyl]morpholin-3-one | 3.82 340.2 E | ¹H NMR (400 MHz, DMSO-d₆) δ 12.3 (br.s, 1H), 8.46 (d, J = 2.1 Hz, 1H), 8.16 (d, J = 2.2 Hz, 1H), 7.75 (t, J = 1.8 Hz, 1H), 7.66-7.62 (m, 1H), 7.51 (t, J = 7.9 Hz, 1H), 7.38 (ddd, J = 7.9, 2.0, 1.0 Hz, 1H), 4.23 (s, 2H), 4.03-3.99 (m, 2H), 3.86-3.81 (m, 2H), 2.67 (q, J = 7.4 Hz, 2H), 1.2 (t, J = 7.4 Hz, 3H); |

TABLE A1-continued

| Compound | Structure/Name | LCMS R$_T$ (min), M + H$^+$, method | $^1$H NMR (ppm) |
|---|---|---|---|
| 1-19 | 6-Amino-3-(3-ethyl-2-fluoro-1H-pyrrolo[2,3-b]pyridin-5-yl)-2-fluoro-N,N-dimethylbenzamide | 3.65 345.1 E | $^1$H NMR (400 MHz, DMSO-d$_6$) δ 12.2 (br.s, 1H), 8.20 (t, J = 1.9 Hz, 1H), 7.89 (t, J = 1.8 Hz, 1H), 7.28 (t, J = 8.8 Hz, 1H), 6.63 (d, J = 8.5 Hz, 1H), 5.40 (br.s, 2H), 3.01 (s, 3H), 2.91 (s, 3H), 2.64 (q, J = 7.7 Hz, 2H), 1.22 (t, J = 7.6 Hz, 3H); |
| 1-20 | 6-Amino-3-[2-chloro-3-(2-hydroxyethyl)-1-(toluene-4-sulfonyl)-1H-pyrrolo[2,3-b]pyridin-5-yl]-2-fluoro-N,N-dimethylbenzamide | 2.72 377.1 D | $^1$H NMR (400 MHz, DMSO-d$_6$) δ 12.27 (br s, 1H), 8.25 (m, 1H), 7.95 (m, 1H), 7.28 (m, 1H), 6.63 (d, J = 8.6 Hz, 1H), 5.42 (br s, 2H), 4.70 (t, J = 5.3 Hz, 1H), 3.59 (m, 2H), 3.01 (s, 3H), 2.90 (s, 3H), 2.83 (m, 2H) |
| 1-21 | 4-{3-[2-Chloro-3-(2-hydroxyethyl)-1-(toluene-4-sulfonyl)-1H-pyrrolo[2,3-b]pyridin-5-yl]phenyl}morpholin-3-one | 2.86 372.1 C | $^1$H NMR (400 MHz, DMSO-d$_6$) δ 12.33 (br s, 1H), 8.51 (d, J = 2.2 Hz, 1H), 8.20 (d, J = 2.2 Hz, 1H), 7.75 (m, 1H), 7.64 (dm, J = 7.7 Hz, 1H), 7.52 (m, 1H), 7.38 (dm, J = 7.8 Hz, 1H), 4.70 (t, J = 5.4 Hz, 1H), 4.23 (br s, 2H), 4.00 (m, 2H), 3.83 (m, 2H), 3.63 (m, 2H), 2.88 (m, 2H) |

Additional compounds of Formulae I and Ia were prepared using methods described herein and known in the art. The structures, names and LC/MS data are provided in Table A2.

TABLE A2

| Compound | Structure | Name | LCMS R$_T$ (min), M + H$^+$, method |
|---|---|---|---|
| 1-22 | 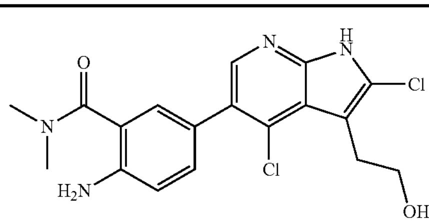 | 2-amino-5-(2,4-dichloro-3-(2-hydroxyethyl)-1H-pyrrolo[2,3-b]pyridin-5-yl)-N,N-dimethylbenzamide | 2.93 393.1 E |

TABLE A2-continued

| Compound | Structure | Name | LCMS R_T (min), M + H+, method |
|---|---|---|---|
| 1-23 | 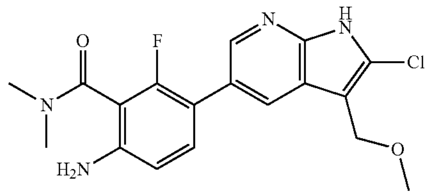 [SMILES: COCc1c(Cl)[nH]c2ncc(-c3ccc(N)c(C(=O)N(C)C)c3F)cc12] | 6-amino-3-(2-chloro-3-(methoxymethyl)-1H-pyrrolo[2,3-b]pyridin-5-yl)-2-fluoro-N,N-dimethylbenzamide | n/a |
| 1-24 | 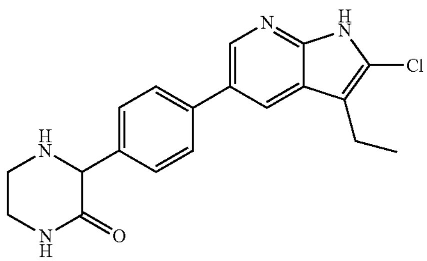 [SMILES: CCc1c(Cl)[nH]c2ncc(-c3ccc(C4NCCNC4=O)cc3)cc12] | 3-(4-(2-chloro-3-ethyl-1H-pyrrolo[2,3-b]pyridin-5-yl)phenyl)piperazin-2-one | 2.65 355.1 E |
| 1-25 | 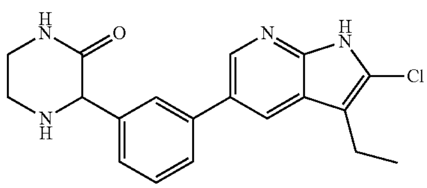 [SMILES: CCc1c(Cl)[nH]c2ncc(-c3cccc(C4NCCNC4=O)c3)cc12] | 3-(3-(2-chloro-3-ethyl-1H-pyrrolo[2,3-b]pyridin-5-yl)phenyl)piperazin-2-one | 2.72 355.1 E |
| 1-26 | 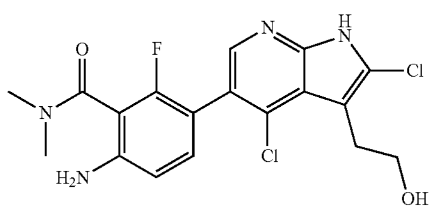 [SMILES: CN(C)C(=O)c1c(N)ccc(-c2cnc3[nH]c(Cl)c(CCO)c3c2Cl)c1F] | 6-amino-3-(2,4-dichloro-3-(2-hydroxyethyl)-1H-pyrrolo[2,3-b]pyridin-5-yl)-2-fluoro-N,N-dimethylbenzamide | 3.02 411.0 E |
| 1-27 | 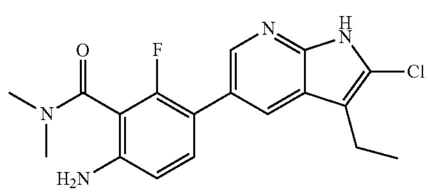 [SMILES: CCc1c(Cl)[nH]c2ncc(-c3ccc(N)c(C(=O)N(C)C)c3F)cc12] | 6-amino-3-(2-chloro-3-ethyl-1H-pyrrolo[2,3-b]pyridin-5-yl)-2-fluoro-N,N-dimethylbenzamide | 3.90 361.1 E |

2. Biological

Exemplary compounds of Formulae I and Ia were tested to assess compound inhibition of HPK-1. The $K_i$ for each exemplary compound was determined (Table B1).

TABLE B1

| Compound | HPK1 $K_i$ (µM) |
|---|---|
| 1-1 | 0.002 |
| 1-2 | 0.003 |
| 1-3 | 0.0009 |
| 1-4 | 0.015 |
| 1-5 | 0.002 |
| 1-6 | 0.015 |
| 1-7 | 0.033 |
| 1-8 | 0.068 |
| 1-9 | 0.076 |
| 1-10 | 0.032 |

TABLE B1-continued

| Compound | HPK1 $K_i$ (µM) |
|---|---|
| 1-11 | 0.013 |
| 1-12 | 0.024 |
| 1-13 | 1.7 |
| 1-14 | 0.017 |
| 1-15 | 0.075 |
| 1-16 | 0.082 |
| 1-17 | 1.3 |
| 1-18 | 0.004 |
| 1-19 | 0.001 |
| 1-20 | 0.017 |
| 1-21 | 0.089 |
| 1-22 | 0.0094 |
| 1-23 | 0.160 |
| 1-24 | 0.032 |
| 1-25 | 0.031 |

TABLE B1-continued

| Compound | HPK1 $K_i$ (μM) |
|---|---|
| 1-26 | 0.012 |
| 1-27 | 0.0027 |

Further Embodiments

1. A compound of Formula I:

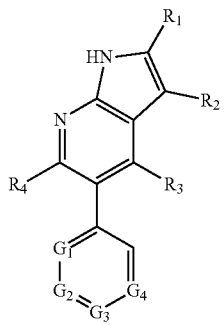

(I)

or a pharmaceutically acceptable salt thereof, wherein,
$G_1$ is N or C—$R_{x1}$;
$G_2$ is N or C—$R_{x2}$;
$G_3$ is N or C—$R_{x3}$;
$G_4$ is N or C—$R_{x4}$;
wherein, 0, 1 or 2 of $G_1$, $G_2$, $G_3$, and $G_4$ is N;
$R_{x1}$, $R_{x2}$, $R_{x3}$ and $R_{x4}$, if present, in each instance, is independently selected from the group consisting of hydrogen, halo, $C_6$-$C_{20}$ aryl optionally substituted with one or two $R_{1a}$, $C_1$-$C_{20}$ heteroaryl optionally substituted with one or two $R_{1a}$, —CONR$_6$R$_7$, —NR$_6$R$_7$, and —N(R$_8$)—CO(R$_9$), provided that at least one of $R_{x1}$, $R_{x2}$, $R_{x3}$ and $R_{x4}$ is other than hydrogen;
wherein, $R_6$ and $R_7$ taken together with the N to which each is bound form a 4-, 5-, 6- or 7-member cyclic or heterocyclic ring, wherein said heterocyclic ring may contain one or two additional heteroatoms selected from the group consisting of N, S and O, said ring may be optionally substituted with one or two $R_{1a}$; or
$R_6$ and $R_7$ are independently hydrogen or alkyl;
wherein, $R_8$ and $R_9$ taken together with the N or the carbonyl to which each is bound form a 4-, 5-, 6- or 7-member cyclic or heterocyclic ring, wherein said heterocyclic ring may contain one or two additional heteroatoms selected from the group consisting of N, S and O, said ring may be optionally substituted with one or two $R_{1a}$; or
$R_8$ and $R_9$ are independently hydrogen or alkyl;
wherein, in each instance, $R_{1a}$ is independently taken together with the carbon to which it is bound to form a carbonyl; or $R_{1a}$ is hydrogen, alkyl, hydroxyl, hydroxyalkyl, halo or haloalkyl;
$R_1$ is hydrogen, alkyl, hydroxyl, hydroxyalkyl, halo or haloalkyl;
$R_2$, $R_3$, and $R_4$, in each instance, is independently hydrogen, alkyl, alkoxy, halo, —CF$_3$, —O—CF$_3$; —CF$_2$R$_5$; haloalkyl-, haloalkoxy-, —SO$_2$R$_5$, —SOR$_5$, or cycloalkyl;
wherein $R_5$, in each instance, is independently an unsubstituted alkyl;
provided that $R_1$ and $R_4$ are not both hydrogen.

2. The compound of embodiment 1, wherein one or both of $G_1$ and $G_3$ are N; $G_2$ is C—$R_{x2}$; and $G_4$ is C—$R_{x4}$.

3. The compound of embodiment 2, wherein $G_1$ is N and $G_3$ is C—$R_{x3}$.

4. The compound of embodiment 2 or 3, wherein $R_1$ and $R_2$, in each instance, is independently alkyl, haloalkyl, hydroxyalkyl, —CF$_3$ or halo.

5. The compound of embodiment 4, wherein $R_1$ and $R_2$, in each instance, is independently halo or alkyl.

6. The compound of embodiment 1, wherein $G_1$ is C—$R_{x1}$; $G_2$ is C—$R_{x2}$; $G_3$ is C—$R_{x3}$; and $G_4$ is C—$R_{x4}$.

7. The compound of embodiment 6, wherein $R_1$ and $R_2$, in each instance, is independently alkyl, haloalkyl, hydroxyalkyl, —CF$_3$ or halo.

8. The compound of embodiment 7, wherein $R_1$ and $R_2$, in each instance, is independently halo or alkyl.

9. The compound of embodiment 8, wherein two of $R_{x1}$, $R_{x2}$, $R_{x3}$ and $R_{x4}$ are hydrogen.

10. The compound of embodiment 2, 3 or 9, wherein $R_{x2}$ is selected from:

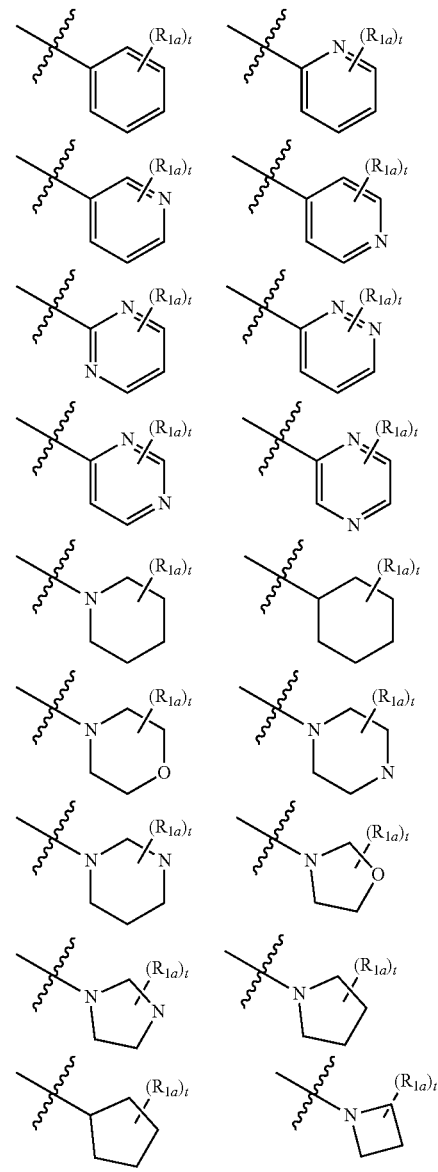

-continued

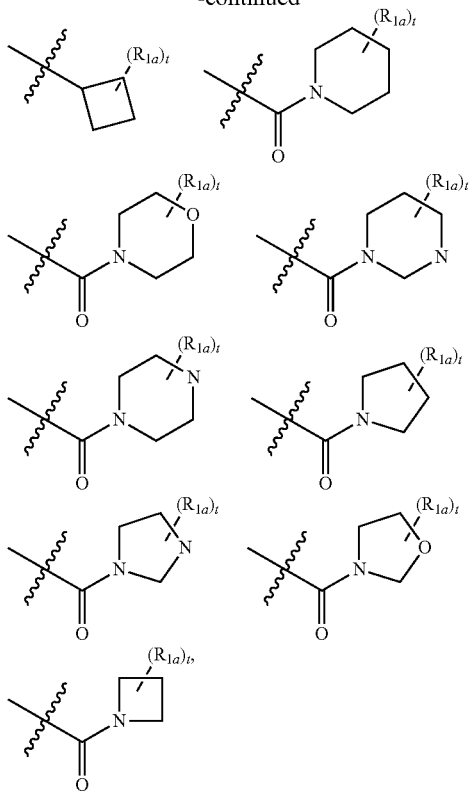

wherein, t is 1 or 2.

11. The compound of embodiment 10, wherein $R_{x1}$ is hydrogen or halo; $R_{x3}$ is hydrogen or —$NH_2$; $R_{x4}$ is hydrogen or —$NH_2$, wherein at least one of $R_{x1}$, $R_{x2}$ and $R_{x3}$ is hydrogen.

12. The compound of embodiment 1, having Formula Ia:

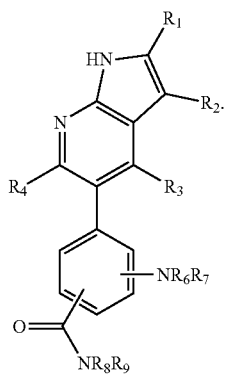

(Ia)

13. The compound of embodiment 12, wherein $R_8$ and $R_9$, in each instance, is independently a $C_{1-4}$ alkyl; and $R_6$ and $R_7$ are both hydrogen.

14. The compound of embodiment 13, wherein $R_8$ and $R_9$ are both methyl.

15. The compound of embodiment 12, 13, or 14, wherein $R_1$ is alkyl, hydroxyl, hydroxyalkyl, halo or haloalkyl; and $R_3$ and $R_4$ are each hydrogen.

16. The compound of embodiment 15, wherein $R_1$ is alkyl, halo or haloalkyl; $R_2$ is hydrogen, alkyl, alkoxy, halo, haloalkyl or —$CF_3$.

17. The compound of embodiment 16, wherein $R_1$ is $C_{1-4}$ alkyl.

18. The compound of embodiment 16, wherein $R_1$ is chloro.

19. The compound of embodiment 16, wherein $R_2$ is hydrogen, $C_{1-4}$ alkyl or —$CF_3$.

20. The compound of embodiment 1, having a structure selected from the group consisting of:

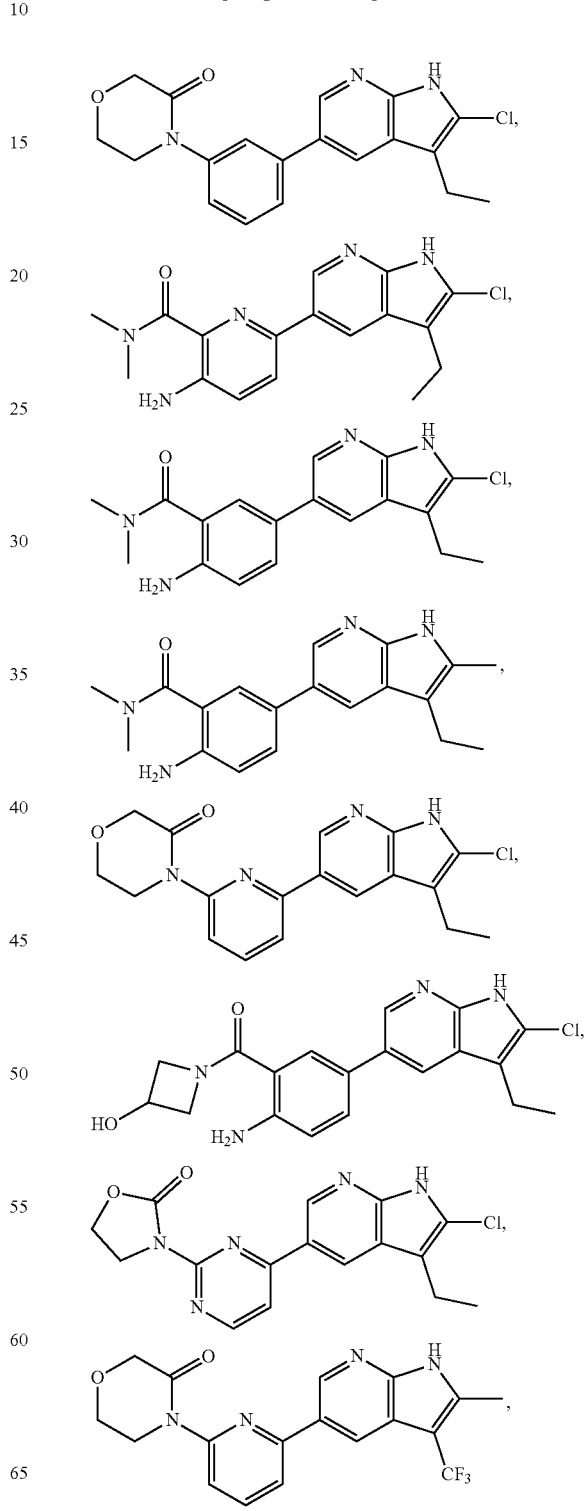

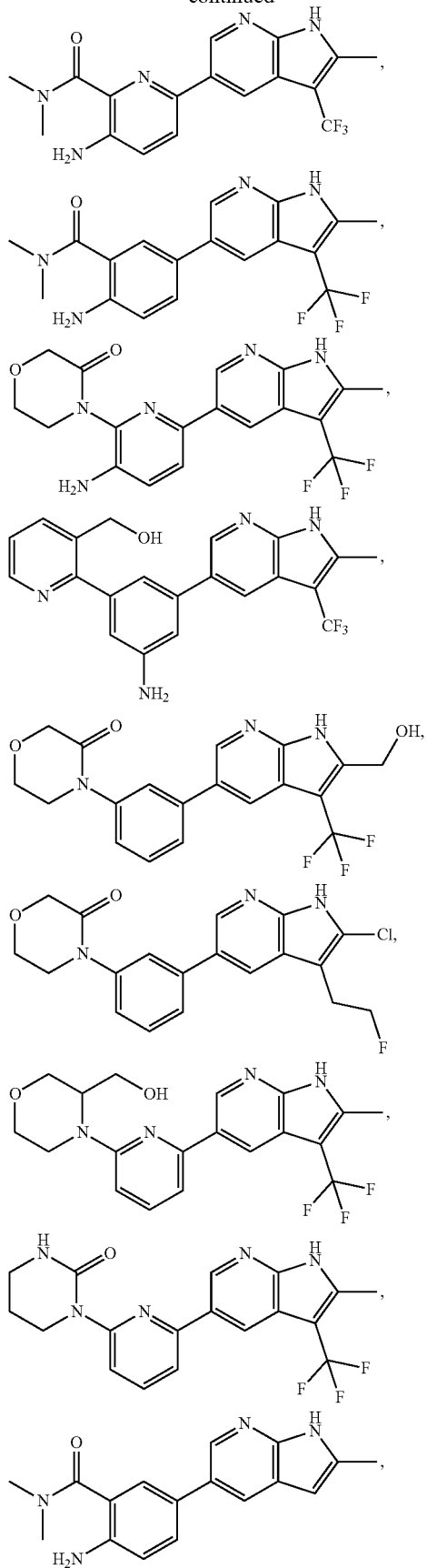

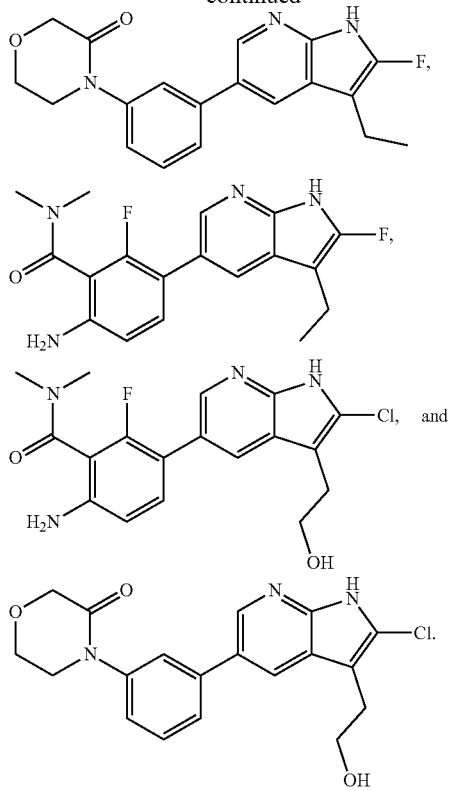

21. A pharmaceutical composition comprising a compound of any one of embodiments 1-20 and a pharmaceutically acceptable carrier.

22. The pharmaceutical composition of embodiment 21, wherein said composition further comprises a chemotherapeutic agent.

23. The pharmaceutical composition of embodiment 22, wherein said chemotherapeutic agent is an immunotherapeutic agent.

24. A method for inhibiting HPK1, said method comprising contacting HPK1 with an effective amount of a compound of any one of embodiments 1-20 or a pharmaceutical composition of any one of embodiments 21-23.

25. A method for enhancing an immune response in a subject in need thereof, wherein the method comprises administering to said subject an effective amount of a compound of any one of embodiments 1-20 or a pharmaceutical composition of any one of embodiments 21-23.

26. The method of embodiment 25, wherein T cells in the subject have at least one of enhanced priming, enhanced activation, enhanced migration, enhanced proliferation, enhanced survival, and enhanced cytolytic activity relative to prior to the administration of the compound or pharmaceutical composition.

27. The method of embodiment 26, wherein the T cell activation is characterized by an elevated frequency of γ-IFN+ CD8 T cells or enhanced levels of IL-2 or granzyme B production by T cells relative to prior to administration of the compound or pharmaceutical composition.

28. The method of embodiment 27, wherein the number of T cells is elevated relative to prior to administration of the compound or pharmaceutical composition.

29. The method of any one of embodiments 26-28, wherein the T cell is an antigen-specific CD8 T cell.

30. The method of embodiment 25, wherein the antigen presenting cells in the subject have enhanced maturation and activation relative to prior to the administration of the compound or pharmaceutical composition.

31. The method of embodiment 30, wherein the antigen presenting cells are dendritic cells.

32. The method of embodiment 30, wherein the maturation of the antigen presenting cells is characterized by increased frequency of CD83[+] dendritic cells.

33. The method of embodiment 30, wherein the activation of the antigen presenting cells is characterized by elevated expression of CD80 and CD86 on dendritic cells.

34. The method of any one of embodiments 24-33, wherein said subject has cancer.

35. A method for treating a HPK1-dependent disorder, said method comprising administering to a subject in need thereof an effective amount of a compound of any one of embodiments 1-20 or a pharmaceutical composition of any one of embodiments 21-23.

36. The method of embodiment 35, wherein said HPK1-dependent disorder is a cancer.

37. The method of embodiment 34 or 36, wherein the cancer comprises at least one cancer selected from the group consisting of colorectal cancer, melanoma, non-small cell lung cancer, ovarian cancer, breast cancer, pancreatic cancer, a hematological malignancy, and a renal cell carcinoma.

38. The method of any one of embodiments 34, 36, or 37, wherein the cancer has elevated levels of T-cell infiltration.

39. The method of any one of embodiments 34, 36, 37, or 38, wherein the cancer cells in the subject selectively have elevated expression of MHC class I antigen expression relative to prior to the administration of the compound or composition.

40. The method of any one of embodiments 34, 36, 37, 38, or 39, wherein said method further comprises administering an additional chemotherapeutic agent to said subject.

41. The method of embodiment 40, wherein said chemotherapeutic agent is administered to said subject simultaneously with said compound or said composition.

42. The method of embodiment 40, wherein said chemotherapeutic agent is administered to said subject prior to administration of said compound or said composition.

43. The method of embodiment 40, wherein said chemotherapeutic agent is administered to said subject after administration of said compound or said composition.

We claim:
1. A compound of Formula I:

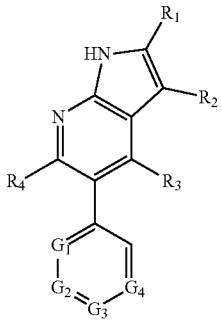

or a pharmaceutically acceptable salt thereof, wherein,
$G_1$ is N or C—$R_{x1}$;
$G_2$ is N or C—$R_{x2}$;
$G_3$ is N or C—$R_{x3}$;
$G_4$ is N or C—$R_{x4}$;
  wherein, 0, 1 or 2 of $G_1$, $G_2$, $G_3$, and $G_4$ is N;
  $R_{x1}$, $R_{x2}$, $R_{x3}$ and $R_{x4}$, if present, in each instance, is independently selected from the group consisting of hydrogen, halo, $C_6$-$C_{20}$ aryl optionally substituted with one or two $R_{1a}$, $C_1$-$C_{20}$ heteroaryl optionally substituted with one or two $R_{1a}$, —CONR$_6$R$_7$, —NR$_6$R$_7$, and —N(R$_8$)—CO(R$_9$), provided that at least one of $R_{x1}$, $R_{x2}$, $R_{x3}$ and $R_{x4}$ is other than hydrogen;
    wherein, $R_6$ and $R_7$ taken together with the N to which each is bound form a 4-, 5-, 6- or 7-member cyclic or heterocyclic ring, wherein said heterocyclic ring may contain one or two additional heteroatoms selected from the group consisting of N, S and O, said ring may be optionally substituted with one or two $R_{1a}$; or $R_6$ and $R_7$ are independently hydrogen or alkyl;
    wherein, $R_8$ and $R_9$ taken together with the N or the carbonyl to which each is bound form a 4-, 5-, 6- or 7-member cyclic or heterocyclic ring, wherein said heterocyclic ring may contain one or two additional heteroatoms selected from the group consisting of N, S and O, said ring may be optionally substituted with one or two $R_{1a}$; or $R_8$ and $R_9$ are independently hydrogen or alkyl;
    wherein, in each instance, $R_{1a}$ is independently taken together with the carbon to which it is bound to form a carbonyl; or $R_{1a}$ is hydrogen, alkyl, hydroxyl, hydroxyalkyl, halo or haloalkyl;
$R_1$ is hydrogen, alkyl, hydroxyl, hydroxyalkyl, halo or haloalkyl;
$R_2$ is alkyl, alkoxy, halo, haloalkyl-, haloalkoxy-, —R$_5$—O—R$_5$, —SO$_2$R$_5$, —SOR$_5$, or cycloalkyl; and
$R_3$ and $R_4$, in each instance, is independently hydrogen, alkyl, alkoxy, halo, haloalkyl-, haloalkoxy-, —R$_5$—O—R$_5$, —SO$_2$R$_5$, —SO$_2$R$_5$, or cycloalkyl;
    wherein $R_5$, in each instance, is independently an unsubstituted alkyl;
provided that $R_1$ and $R_4$ are not both hydrogen.

2. The compound of claim 1, wherein one or both of $G_1$ and $G_3$ are N; $G_2$ is C—$R_{x2}$; and $G_4$ is C—$R_{x4}$.

3. The compound of claim 1, wherein $G_1$ is N and $G_3$ is C—$R_3$.

4. The compound of claim 1, wherein $R_1$ and $R_2$, in each instance, is independently alkyl, haloalkyl or halo.

5. The compound of claim 4, wherein the haloalkyl is —CF$_3$ or —CF$_2$R$_5$.

6. The compound of claim 4, wherein $R_1$ and $R_2$, in each instance, is independently halo or alkyl.

7. The compound of claim 1, wherein $G_1$ is C—$R_{x1}$; $G_2$ is C—$R_{x2}$; $G_3$ is C—$R_{x3}$; and $G_4$ is C—$R_{x4}$.

8. The compound of claim 7, wherein $R_1$ and $R_2$, in each instance, is independently alkyl, haloalkyl or halo.

9. The compound of claim 7, wherein the haloalkyl is —CF$_3$.

10. The compound of claim 8, wherein $R_1$ and $R_2$, in each instance, is independently halo or alkyl.

11. The compound of claim 1, wherein two of $R_{x1}$, $R_{x2}$, $R_{x3}$ and $R_{x4}$ are hydrogen.

12. The compound of claim 1, wherein $R_{x2}$ is selected from:

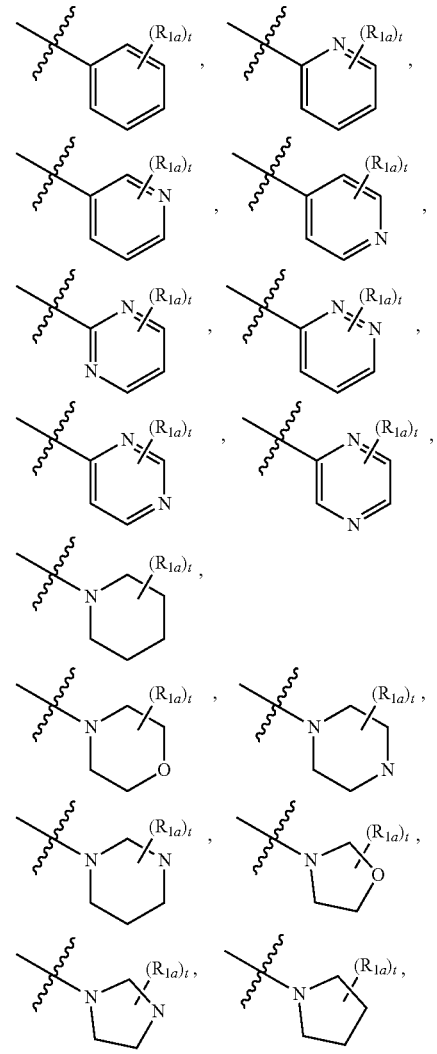

-continued

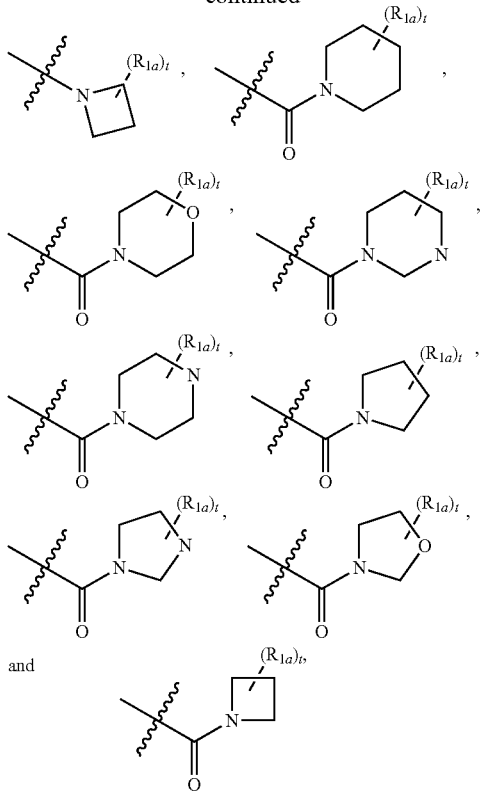

wherein, t is 1 or 2.

13. The compound of claim 12, wherein $R_{x1}$ is hydrogen or halo; $R_{x3}$ is hydrogen or —NH$_2$; $R_{x4}$ is hydrogen or —NH$_2$, wherein at least one of $R_{x1}$, $R_{x3}$ and $R_{x4}$ is hydrogen.

14. The compound of claim 1, having Formula Ia:

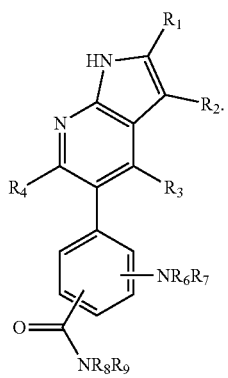

(Ia)

15. The compound of claim 14, wherein $R_8$ and $R_9$, in each instance, is independently a C$_{1-4}$ alkyl; and $R_6$ and $R_7$ are both hydrogen.

16. The compound of claim 15, wherein $R_8$ and $R_9$ are both methyl.

17. The compound of claim 1, wherein $R_1$ is alkyl, hydroxyl, hydroxyalkyl, halo or haloalkyl; and $R_3$ and $R_4$ are each hydrogen.

18. The compound of claim 17, wherein $R_1$ is alkyl, halo or haloalkyl; $R_2$ is hydrogen, alkyl, alkoxy, halo or haloalkyl.

19. The compound of claim 17, wherein $R_1$ is alkyl, halo or haloalkyl; $R_2$ is hydrogen, alkyl, alkoxy, halo or —CF$_3$.

20. The compound of claim 14, wherein $R_1$ is C$_{1-4}$ alkyl.

21. The compound of claim 14, wherein $R_1$ is chloro.

22. The compound of claim 14, wherein $R_2$ is hydrogen, C$_{1-4}$ alkyl or —CF$_3$.

23. A compound selected from the group consisting of:

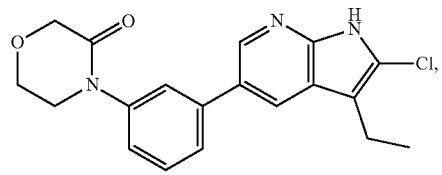

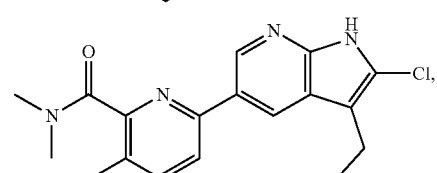

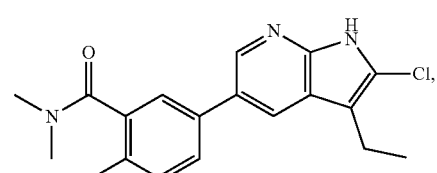

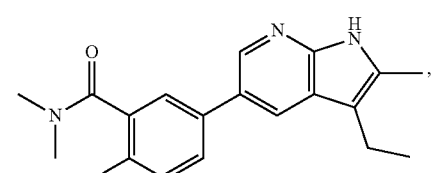

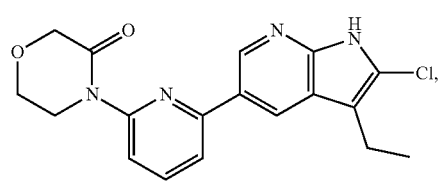

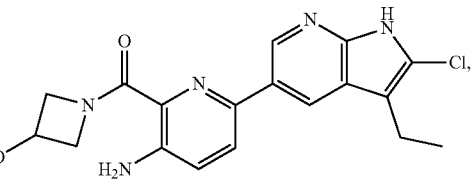

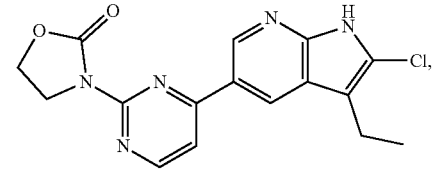

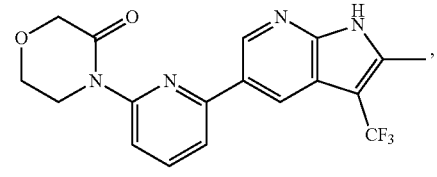

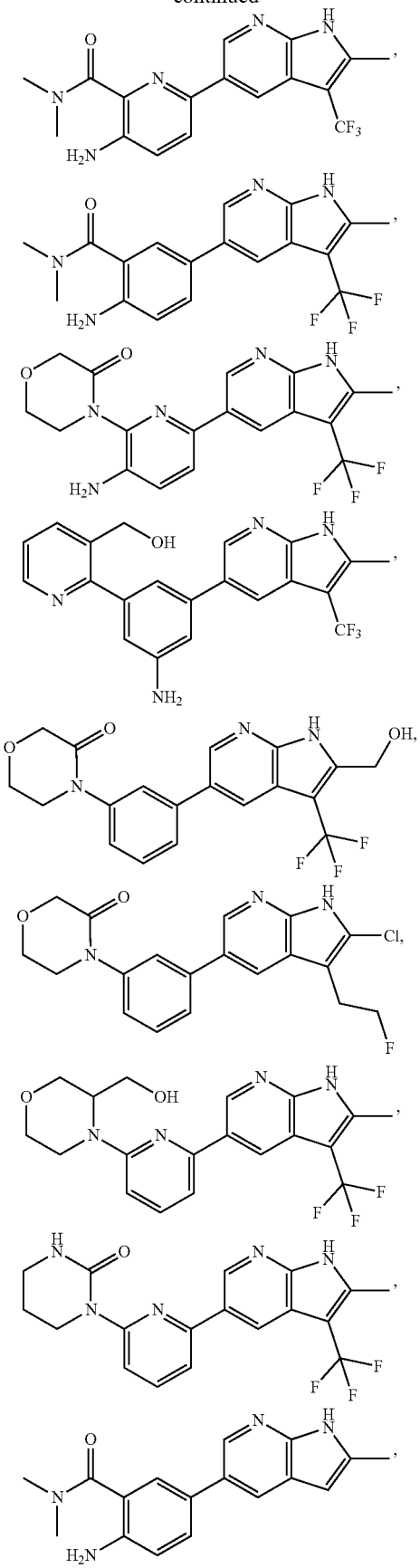
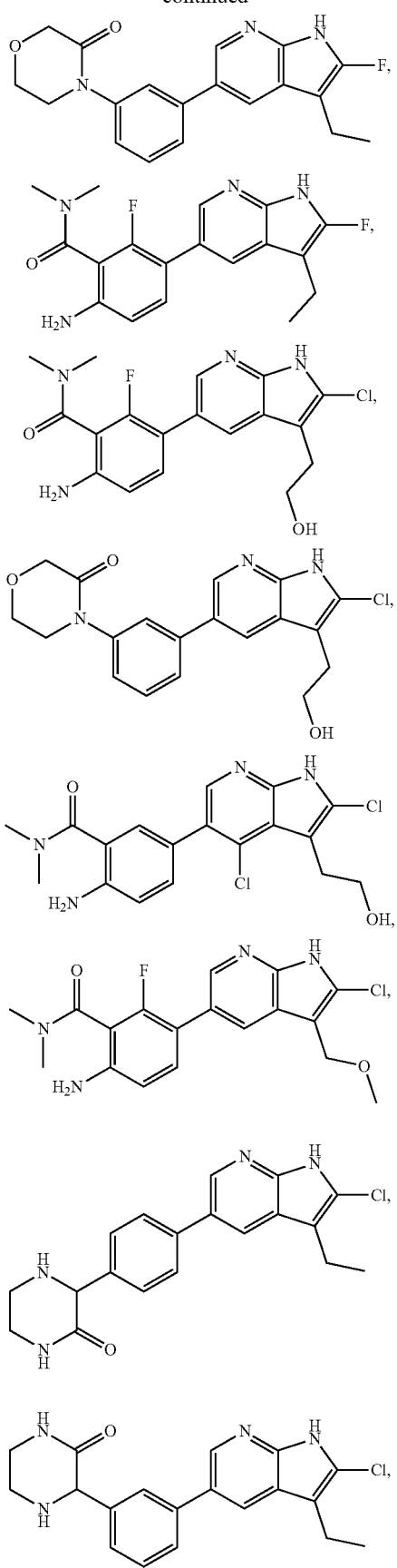

-continued

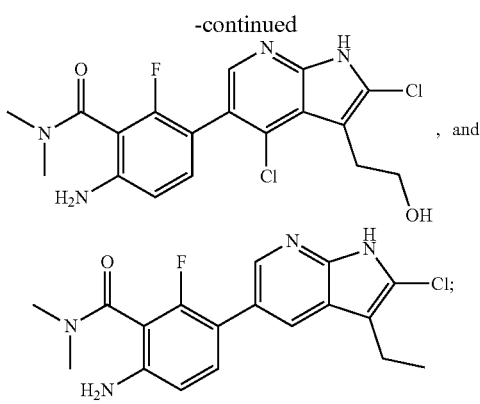

, and

or a pharmaceutically acceptable salt thereof.

24. A pharmaceutical composition comprising a compound of claim 1, or a pharmaceutically acceptable salt thereof, and a pharmaceutically acceptable carrier.

25. The pharmaceutical composition of claim 24, wherein said composition further comprises a chemotherapeutic agent.

26. The pharmaceutical composition of claim 25, wherein said chemotherapeutic agent is an immunotherapeutic agent.

27. The compound of claim 23, which is

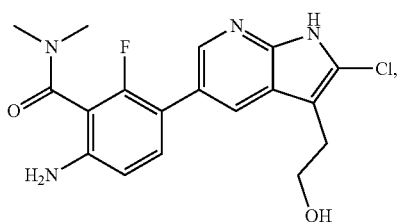 [SMILES: CN(C)C(=O)c1c(N)ccc(-c2cnc3[nH]c(Cl)c(CCO)c3c2)c1F]

or a pharmaceutically acceptable salt thereof.

28. The compound of claim 23, which is

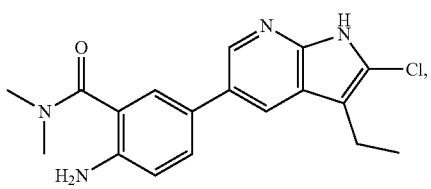 [SMILES: CCc1c(Cl)[nH]c2ncc(-c3ccc(N)c(C(=O)N(C)C)c3)cc12]

or a pharmaceutically acceptable salt thereof.

29. The compound of claim 23, which is

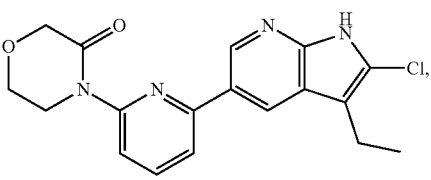 [SMILES: CCc1c(Cl)[nH]c2ncc(-c3cccc(N4CCOCC4=O)n3)cc12]

or a pharmaceutically acceptable salt thereof.

30. The compound of claim 23, which is

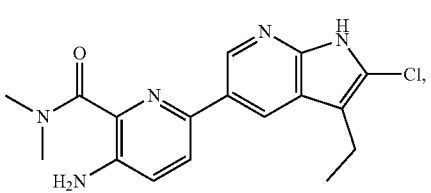 [SMILES: CCc1c(Cl)[nH]c2ncc(-c3ccc(N)c(C(=O)N(C)C)n3)cc12]

or a pharmaceutically acceptable salt thereof.

31. The compound of claim 23, which is

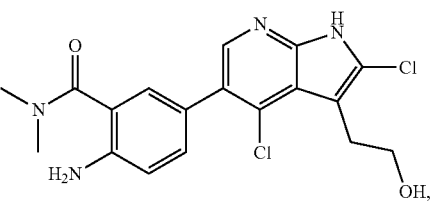

or a pharmaceutically acceptable salt thereof.

32. The compound of claim 23, which is

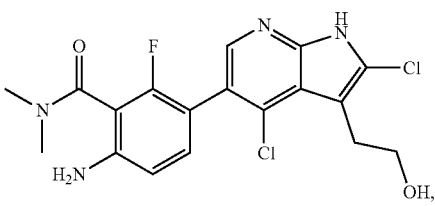 [SMILES: CN(C)C(=O)c1c(N)ccc(-c2cnc3[nH]c(Cl)c(CCO)c3c2Cl)c1F]

or a pharmaceutically acceptable salt thereof.

* * * * *